US008774907B2

(12) United States Patent
Rothenberg

(10) Patent No.: US 8,774,907 B2
(45) Date of Patent: *Jul. 8, 2014

(54) METHOD OF LOCATING THE TIP OF A CENTRAL VENOUS CATHETER

(71) Applicant: Bard Access Systems, Inc., Salt Lake City, UT (US)

(72) Inventor: Peter M. Rothenberg, Laguna Niguel, CA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 23 days.

This patent is subject to a terminal disclaimer.

(21) Appl. No.: 13/737,806

(22) Filed: Jan. 9, 2013

(65) Prior Publication Data

US 2013/0123597 A1    May 16, 2013

Related U.S. Application Data

(60) Division of application No. 12/427,244, filed on Apr. 21, 2009, now Pat. No. 8,388,546, which is a continuation-in-part of application No. 11/552,094, filed on Oct. 23, 2006, now Pat. No. 7,794,407, and a continuation of application No. PCT/US2009/033116, filed on Feb. 4, 2009.

(60) Provisional application No. 61/026,372, filed on Feb. 5, 2008.

(51) Int. Cl.
*A61B 5/04* (2006.01)
*A61N 1/00* (2006.01)

(52) U.S. Cl.
USPC .............. 600/509; 600/508; 600/510; 607/28; 607/122

(58) Field of Classification Search
USPC ............................ 600/508–510; 607/28, 122
See application file for complete search history.

(56) References Cited

U.S. PATENT DOCUMENTS 3,133,244 A     5/1964   Wojtulewicz
3,297,020 A     1/1967   Mathiesen
(Continued)

FOREIGN PATENT DOCUMENTS

AU          642647      11/1990
AU       1860597 B2      6/1999
(Continued)

OTHER PUBLICATIONS

U.S. Appl. No. 11/466,602, filed Aug. 23, 2006 Final Office Action dated Jan. 30, 2009.

(Continued)

*Primary Examiner* — Niketa Patel
*Assistant Examiner* — William Levicky
(74) *Attorney, Agent, or Firm* — Rutan & Tucker, LLP

(57) ABSTRACT

Methods of locating a tip of a central venous catheter ("CVC") relative to the superior vena cava, sino-atrial node, right atrium, and/or right ventricle using electrocardiogram data. The CVC includes at least one electrode. In particular embodiments, the CVC includes two or three pairs of electrodes. Further, depending upon the embodiment implemented, one or more electrodes may be attached to the patient's skin. The voltage across the electrodes is used to generate a P wave. A reference deflection value is determined for the P wave detected when the tip is within the proximal superior vena cava. Then, the tip is advanced and a new deflection value determined. A ratio of the new and reference deflection values is used to determine a tip location. The ratio may be used to instruct a user to advance or withdraw the tip.

1 Claim, 15 Drawing Sheets

(56) References Cited

U.S. PATENT DOCUMENTS

| | | |
|---|---|---|
| 3,625,200 A | 12/1971 | Muller |
| 3,674,014 A | 7/1972 | Tillander et al. |
| 3,817,241 A | 6/1974 | Grausz |
| 3,847,157 A | 11/1974 | Caillouette et al. |
| 3,868,565 A | 2/1975 | Kuipers |
| 3,902,501 A | 9/1975 | Citron et al. |
| 3,995,623 A | 12/1976 | Blake et al. |
| 4,003,369 A | 1/1977 | Heilman et al. |
| 4,063,561 A | 12/1977 | McKenna |
| 4,072,146 A | 2/1978 | Howes |
| 4,114,601 A | 9/1978 | Abels |
| 4,149,535 A | 4/1979 | Volder |
| 4,173,228 A | 11/1979 | Steenwyk et al. |
| 4,175,566 A | 11/1979 | Millar |
| 4,181,120 A | 1/1980 | Kunii et al. |
| 4,224,949 A | 9/1980 | Scott et al. |
| 4,244,362 A | 1/1981 | Anderson |
| 4,289,139 A | 9/1981 | Enjoji et al. |
| 4,317,078 A | 2/1982 | Weed et al. |
| 4,327,722 A | 5/1982 | Groshong et al. |
| 4,362,166 A | 12/1982 | Furler et al. |
| 4,365,639 A | 12/1982 | Goldreyer |
| 4,380,237 A | 4/1983 | Newbower |
| 4,407,294 A | 10/1983 | Vilkomerson |
| 4,429,693 A | 2/1984 | Blake et al. |
| 4,431,005 A | 2/1984 | McCormick |
| 4,431,214 A | 2/1984 | Buffington |
| 4,445,501 A | 5/1984 | Bresler |
| 4,459,854 A | 7/1984 | Richardson et al. |
| 4,469,106 A | 9/1984 | Harui |
| 4,483,343 A | 11/1984 | Beyer et al. |
| 4,491,137 A | 1/1985 | Jingu |
| 4,565,201 A | 1/1986 | Lass |
| 4,572,198 A | 2/1986 | Codrington |
| 4,577,634 A | 3/1986 | Gessman |
| 4,582,067 A | 4/1986 | Silverstein et al. |
| 4,588,394 A | 5/1986 | Schulte et al. |
| 4,593,687 A | 6/1986 | Gray |
| 4,595,012 A | 6/1986 | Webler et al. |
| 4,601,706 A | 7/1986 | Aillon |
| 4,608,989 A | 9/1986 | Drue |
| 4,608,992 A | 9/1986 | Hakim et al. |
| 4,619,247 A | 10/1986 | Inoue et al. |
| 4,622,644 A | 11/1986 | Hansen |
| 4,644,960 A | 2/1987 | Johans |
| 4,652,820 A | 3/1987 | Maresca |
| 4,665,925 A | 5/1987 | Millar |
| 4,667,230 A | 5/1987 | Arakawa et al. |
| 4,674,518 A | 6/1987 | Salo |
| 4,676,249 A | 6/1987 | Arenas et al. |
| 4,681,106 A | 7/1987 | Kensey et al. |
| 4,681,117 A | 7/1987 | Brodman et al. |
| 4,688,578 A | 8/1987 | Takano et al. |
| 4,692,148 A | 9/1987 | Kantrowitz et al. |
| 4,697,595 A | 10/1987 | Breyer et al. |
| 4,700,997 A | 10/1987 | Strand |
| 4,706,681 A | 11/1987 | Breyer et al. |
| 4,710,708 A | 12/1987 | Rorden et al. |
| 4,733,669 A | 3/1988 | Segal |
| 4,737,794 A | 4/1988 | Jones |
| 4,741,356 A | 5/1988 | Letzo et al. |
| 4,742,356 A | 5/1988 | Kuipers |
| 4,753,247 A | 6/1988 | Kirsner et al. |
| 4,770,185 A | 9/1988 | Silverstein et al. |
| 4,771,788 A | 9/1988 | Millar |
| 4,781,685 A | 11/1988 | Lehmann et al. |
| 4,784,646 A | 11/1988 | Feingold |
| 4,787,070 A | 11/1988 | Suzuki et al. |
| 4,787,396 A | 11/1988 | Pidorenko |
| 4,793,361 A | 12/1988 | DuFault |
| 4,794,930 A | 1/1989 | Machida et al. |
| 4,796,632 A | 1/1989 | Boyd et al. |
| 4,798,588 A | 1/1989 | Aillon |
| 4,798,598 A | 1/1989 | Bonello et al. |
| 4,809,681 A | 3/1989 | Kantrowitz et al. |
| 4,809,713 A | 3/1989 | Grayzel |
| 4,813,729 A | 3/1989 | Speckhart |
| 4,821,731 A | 4/1989 | Martinelli et al. |
| 4,836,214 A | 6/1989 | Sramek |
| 4,840,622 A | 6/1989 | Hardy |
| 4,849,692 A | 7/1989 | Blood |
| 4,850,358 A | 7/1989 | Millar |
| 4,852,580 A | 8/1989 | Wood |
| 4,856,317 A | 8/1989 | Pidorenko et al. |
| 4,856,529 A | 8/1989 | Segal |
| 4,860,757 A | 8/1989 | Lynch et al. |
| 4,867,169 A | 9/1989 | Machida et al. |
| 4,869,263 A | 9/1989 | Segal et al. |
| 4,869,718 A | 9/1989 | Brader |
| 4,887,606 A | 12/1989 | Yock et al. |
| 4,887,615 A | 12/1989 | Taylor |
| 4,889,128 A | 12/1989 | Millar |
| 4,899,756 A | 2/1990 | Sonek |
| 4,901,725 A | 2/1990 | Nappholz et al. |
| 4,905,698 A | 3/1990 | Strohl, Jr. et al. |
| 4,911,173 A | 3/1990 | Terwilliger |
| 4,911,174 A | 3/1990 | Pederson et al. |
| 4,924,870 A | 5/1990 | Wlodarczyk et al. |
| 4,943,770 A | 7/1990 | Ashley-Rollman et al. |
| 4,945,305 A | 7/1990 | Blood |
| 4,947,852 A | 8/1990 | Nassi et al. |
| 4,957,111 A | 9/1990 | Millar |
| 4,961,433 A | 10/1990 | Christian |
| 4,966,148 A | 10/1990 | Millar |
| 4,967,753 A | 11/1990 | Haase et al. |
| 4,977,886 A | 12/1990 | Takehana et al. |
| 4,989,608 A | 2/1991 | Ratner |
| 4,995,396 A | 2/1991 | Inaba et al. |
| 4,998,916 A | 3/1991 | Hammerslag et al. |
| 5,005,592 A | 4/1991 | Cartmell |
| 5,016,173 A | 5/1991 | Kenet et al. |
| 5,025,799 A | 6/1991 | Wilson |
| 5,029,585 A | 7/1991 | Lieber et al. |
| 5,040,548 A | 8/1991 | Yock |
| 5,042,486 A | 8/1991 | Pfeiler et al. |
| 5,045,071 A | 9/1991 | McCormick et al. |
| 5,046,497 A | 9/1991 | Millar |
| 5,050,607 A | 9/1991 | Bradley et al. |
| 5,057,095 A | 10/1991 | Fabian |
| 5,058,595 A | 10/1991 | Kern |
| 5,067,489 A | 11/1991 | Lind |
| 5,076,278 A | 12/1991 | Vilkomerson et al. |
| 5,078,140 A | 1/1992 | Kwoh |
| 5,078,148 A | 1/1992 | Nassi et al. |
| 5,078,149 A | 1/1992 | Katsumata et al. |
| 5,078,678 A | 1/1992 | Katims |
| 5,078,714 A | 1/1992 | Katims |
| 5,084,022 A | 1/1992 | Claude |
| 5,092,341 A | 3/1992 | Kelen |
| 5,099,845 A | 3/1992 | Besz et al. |
| 5,099,850 A | 3/1992 | Matsui et al. |
| 5,100,387 A | 3/1992 | Ng |
| 5,105,829 A | 4/1992 | Fabian et al. |
| 5,109,862 A | 5/1992 | Kelen et al. |
| 5,114,401 A | 5/1992 | Stuart et al. |
| 5,121,750 A | 6/1992 | Katims |
| 5,134,370 A | 7/1992 | Jefferts et al. |
| 5,144,955 A | 9/1992 | O'Hara |
| 5,158,086 A | 10/1992 | Brown et al. |
| 5,160,342 A | 11/1992 | Reger et al. |
| 5,161,536 A | 11/1992 | Vilkomerson et al. |
| 5,174,295 A | 12/1992 | Christian et al. |
| 5,184,601 A | 2/1993 | Putman |
| 5,190,045 A | 3/1993 | Frazin |
| 5,202,985 A | 4/1993 | Goyal |
| 5,211,165 A | 5/1993 | Dumoulin et al. |
| 5,211,636 A | 5/1993 | Mische |
| 5,212,988 A | 5/1993 | White et al. |
| 5,214,615 A | 5/1993 | Bauer |
| 5,217,026 A | 6/1993 | Stoy et al. |
| 5,220,924 A | 6/1993 | Frazin |
| 5,235,987 A | 8/1993 | Wolfe |
| 5,239,464 A | 8/1993 | Blair et al. |
| 5,240,004 A | 8/1993 | Walinsky et al. |

(56) References Cited

U.S. PATENT DOCUMENTS

| | | |
|---|---|---|
| 5,243,995 A | 9/1993 | Maier |
| 5,246,007 A | 9/1993 | Frisbie et al. |
| 5,247,171 A | 9/1993 | Wlodarczyk et al. |
| 5,251,635 A | 10/1993 | Dumoulin et al. |
| 5,255,680 A | 10/1993 | Darrow et al. |
| 5,257,636 A | 11/1993 | White |
| 5,257,979 A | 11/1993 | Jagpal |
| 5,261,409 A | 11/1993 | Dardel |
| 5,265,610 A | 11/1993 | Darrow et al. |
| 5,265,614 A | 11/1993 | Hayakawa et al. |
| 5,267,569 A | 12/1993 | Lienhard |
| 5,270,810 A | 12/1993 | Nishimura |
| 5,271,404 A | 12/1993 | Corl et al. |
| 5,273,025 A | 12/1993 | Sakiyama et al. |
| 5,273,042 A | 12/1993 | Lynch et al. |
| 5,274,551 A | 12/1993 | Corby, Jr. |
| 5,275,053 A | 1/1994 | Wlodarczyk et al. |
| 5,279,129 A | 1/1994 | Ito |
| 5,279,607 A | 1/1994 | Schentag et al. |
| 5,280,786 A | 1/1994 | Wlodarczyk et al. |
| 5,287,331 A | 2/1994 | Schindel et al. |
| 5,289,373 A | 2/1994 | Zarge et al. |
| 5,292,342 A | 3/1994 | Nelson et al. |
| 5,307,072 A | 4/1994 | Jones, Jr. |
| 5,311,871 A | 5/1994 | Yock |
| 5,313,949 A | 5/1994 | Yock |
| 5,318,025 A | 6/1994 | Dumoulin et al. |
| 5,325,860 A | 7/1994 | Seward et al. |
| 5,325,873 A | 7/1994 | Hirschi et al. |
| 5,330,496 A | 7/1994 | Alferness |
| 5,331,966 A | 7/1994 | Bennett et al. |
| 5,333,614 A | 8/1994 | Feiring |
| 5,337,678 A | 8/1994 | Grout et al. |
| 5,341,807 A | 8/1994 | Nardella |
| 5,343,865 A | 9/1994 | Gardineer et al. |
| 5,345,940 A | 9/1994 | Seward et al. |
| 5,348,020 A | 9/1994 | Hutson |
| 5,350,352 A | 9/1994 | Buchholtz et al. |
| 5,357,961 A | 10/1994 | Fields et al. |
| 5,375,596 A | 12/1994 | Twiss et al. |
| 5,376,083 A | 12/1994 | Mische |
| 5,377,678 A | 1/1995 | Dumoulin et al. |
| 5,385,053 A | 1/1995 | Wlodarczyk et al. |
| 5,391,199 A | 2/1995 | Ben-Haim |
| 5,394,876 A | 3/1995 | Ma |
| 5,394,877 A | 3/1995 | Orr et al. |
| 5,395,366 A | 3/1995 | D'Andrea et al. |
| 5,398,683 A | 3/1995 | Edwards et al. |
| 5,398,691 A | 3/1995 | Martin et al. |
| 5,411,485 A | 5/1995 | Tennican et al. |
| 5,413,107 A | 5/1995 | Oakley et al. |
| 5,422,478 A | 6/1995 | Wlodarczyk et al. |
| 5,425,367 A | 6/1995 | Shapiro et al. |
| 5,425,370 A | 6/1995 | Vilkomerson |
| 5,425,382 A | 6/1995 | Golden et al. |
| 5,427,114 A | 6/1995 | Colliver et al. |
| 5,429,132 A | 7/1995 | Guy et al. |
| 5,429,617 A | 7/1995 | Hammersmark et al. |
| 5,431,641 A | 7/1995 | Grozinger et al. |
| 5,433,729 A | 7/1995 | Adams et al. |
| 5,437,276 A | 8/1995 | Takada et al. |
| 5,437,277 A | 8/1995 | Dumoulin et al. |
| 5,438,873 A | 8/1995 | Wlodarczyk et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,450,846 A | 9/1995 | Goldreyer |
| 5,453,575 A | 9/1995 | O'Donnell et al. |
| 5,456,256 A | 10/1995 | Schneider |
| 5,456,718 A | 10/1995 | Szymaitis |
| 5,464,016 A | 11/1995 | Nicholas et al. |
| 5,474,065 A | 12/1995 | Meathrel et al. |
| 5,476,090 A | 12/1995 | Kishi |
| 5,480,422 A | 1/1996 | Ben-Haim |
| 5,487,729 A | 1/1996 | Avellanet et al. |
| 5,490,522 A | 2/1996 | Dardel |
| 5,492,538 A | 2/1996 | Johlin, Jr. |
| 5,494,038 A | 2/1996 | Wang et al. |
| 5,500,012 A | 3/1996 | Brucker et al. |
| 5,505,205 A | 4/1996 | Solomon et al. |
| 5,509,822 A | 4/1996 | Negus et al. |
| 5,513,637 A | 5/1996 | Twiss et al. |
| 5,515,853 A | 5/1996 | Smith et al. |
| 5,522,878 A | 6/1996 | Montecalvo et al. |
| 5,526,812 A | 6/1996 | Dumoulin et al. |
| 5,531,664 A | 7/1996 | Adachi et al. |
| 5,540,230 A | 7/1996 | Vilkomerson |
| 5,540,681 A | 7/1996 | Strul et al. |
| 5,542,938 A | 8/1996 | Avellanet et al. |
| 5,546,949 A | 8/1996 | Frazin et al. |
| 5,546,951 A | 8/1996 | Ben-Haim |
| 5,558,091 A | 9/1996 | Acker et al. |
| 5,568,809 A | 10/1996 | Ben-haim |
| D375,450 S | 11/1996 | Bidwell et al. |
| 5,570,671 A | 11/1996 | Hickey |
| 5,575,291 A | 11/1996 | Hayakawa et al. |
| 5,588,442 A | 12/1996 | Scovil et al. |
| 5,592,939 A | 1/1997 | Martinelli |
| 5,598,846 A | 2/1997 | Peszynski |
| 5,599,299 A | 2/1997 | Weaver et al. |
| 5,600,330 A | 2/1997 | Blood |
| 5,610,967 A | 3/1997 | Moorman et al. |
| 5,617,866 A | 4/1997 | Marian, Jr. |
| 5,622,169 A | 4/1997 | Golden et al. |
| 5,622,170 A | 4/1997 | Schulz |
| 5,622,184 A | 4/1997 | Ashby et al. |
| 5,623,931 A | 4/1997 | Wung et al. |
| 5,624,430 A | 4/1997 | Eton et al. |
| 5,626,554 A | 5/1997 | Ryaby et al. |
| 5,626,870 A | 5/1997 | Monshipouri et al. |
| 5,630,419 A | 5/1997 | Ranalletta |
| 5,644,612 A | 7/1997 | Moorman et al. |
| 5,645,065 A | 7/1997 | Shapiro et al. |
| 5,651,047 A | 7/1997 | Moorman et al. |
| 5,654,864 A | 8/1997 | Ritter et al. |
| D383,968 S | 9/1997 | Bidwell et al. |
| 5,662,115 A | 9/1997 | Torp et al. |
| 5,665,477 A | 9/1997 | Meathrel et al. |
| 5,666,473 A | 9/1997 | Wallace |
| 5,666,958 A | 9/1997 | Rothenberg et al. |
| 5,669,383 A | 9/1997 | Johnson |
| 5,669,388 A | 9/1997 | Vilkomerson |
| 5,676,159 A | 10/1997 | Navis |
| 5,676,673 A | 10/1997 | Ferre et al. |
| 5,691,898 A | 11/1997 | Rosenberg et al. |
| 5,694,945 A | 12/1997 | Ben-Haim |
| 5,695,479 A | 12/1997 | Jagpal |
| 5,697,377 A | 12/1997 | Wittkampf |
| 5,699,801 A | 12/1997 | Atalar et al. |
| 5,700,889 A | 12/1997 | Blair |
| 5,713,362 A | 2/1998 | Vilkomerson |
| 5,713,363 A | 2/1998 | Seward et al. |
| 5,713,946 A | 2/1998 | Ben-Haim |
| 5,715,817 A | 2/1998 | Stevens-Wright et al. |
| 5,716,389 A | 2/1998 | Walinsky et al. |
| 5,718,241 A | 2/1998 | Ben-Haim et al. |
| D391,838 S | 3/1998 | Bidwell et al. |
| 5,722,412 A | 3/1998 | Pflugrath et al. |
| 5,727,550 A | 3/1998 | Montecalvo |
| 5,727,552 A | 3/1998 | Ryan |
| 5,727,553 A | 3/1998 | Saad |
| 5,729,055 A | 3/1998 | Manning |
| 5,729,129 A | 3/1998 | Acker |
| 5,729,584 A | 3/1998 | Moorman et al. |
| 5,730,129 A | 3/1998 | Darrow et al. |
| 5,731,996 A | 3/1998 | Gilbert |
| 5,733,323 A | 3/1998 | Buck et al. |
| 5,738,096 A | 4/1998 | Ben-Haim |
| 5,740,808 A | 4/1998 | Panescu et al. |
| 5,742,394 A | 4/1998 | Hansen |
| 5,744,953 A | 4/1998 | Hansen |
| 5,748,767 A | 5/1998 | Raab |
| 5,749,835 A | 5/1998 | Glantz |
| 5,749,938 A | 5/1998 | Coombs |

(56) References Cited

U.S. PATENT DOCUMENTS

| | | |
|---|---|---|
| 5,751,785 A | 5/1998 | Moorman et al. |
| 5,752,513 A | 5/1998 | Acker et al. |
| 5,758,650 A | 6/1998 | Miller et al. |
| 5,762,064 A | 6/1998 | Polvani |
| 5,767,669 A | 6/1998 | Hansen et al. |
| 5,767,960 A | 6/1998 | Orman et al. |
| 5,769,786 A | 6/1998 | Wiegel |
| 5,769,843 A | 6/1998 | Abela et al. |
| 5,769,881 A | 6/1998 | Schroeppel et al. |
| 5,771,896 A | 6/1998 | Sliwa, Jr. et al. |
| 5,775,322 A | 7/1998 | Silverstein et al. |
| 5,775,332 A | 7/1998 | Goldman |
| 5,779,638 A | 7/1998 | Vesely et al. |
| 5,782,767 A | 7/1998 | Pretlow, III |
| 5,785,657 A | 7/1998 | Breyer et al. |
| 5,792,055 A | 8/1998 | McKinnon et al. |
| 5,795,297 A | 8/1998 | Daigle |
| 5,795,298 A | 8/1998 | Vesely et al. |
| 5,795,632 A | 8/1998 | Buchalter |
| 5,797,849 A | 8/1998 | Vesely et al. |
| 5,800,352 A | 9/1998 | Ferre et al. |
| 5,800,410 A | 9/1998 | Gawreluk |
| 5,800,497 A | 9/1998 | Bakels et al. |
| 5,803,089 A | 9/1998 | Ferre et al. |
| 5,810,733 A | 9/1998 | Van Creveld et al. |
| 5,817,022 A | 10/1998 | Vesely |
| 5,817,024 A | 10/1998 | Ogle et al. |
| 5,820,549 A | 10/1998 | Marian, Jr. |
| 5,824,031 A | 10/1998 | Cookston et al. |
| 5,829,444 A | 11/1998 | Ferre et al. |
| 5,830,145 A | 11/1998 | Tenhoff |
| 5,831,260 A | 11/1998 | Hansen |
| 5,833,608 A | 11/1998 | Acker |
| 5,833,622 A | 11/1998 | Meathrel et al. |
| 5,835,561 A | 11/1998 | Moorman et al. |
| 5,836,882 A | 11/1998 | Frazin |
| 5,836,990 A | 11/1998 | Li |
| 5,840,024 A | 11/1998 | Taniguchi et al. |
| 5,840,025 A | 11/1998 | Ben-Haim |
| 5,840,030 A | 11/1998 | Ferek-Petric et al. |
| 5,840,031 A | 11/1998 | Crowley |
| 5,842,986 A | 12/1998 | Avrin et al. |
| 5,843,076 A | 12/1998 | Webster, Jr. et al. |
| 5,843,153 A | 12/1998 | Johnston et al. |
| 5,844,140 A | 12/1998 | Seale |
| 5,846,198 A | 12/1998 | Killmann |
| 5,855,553 A | 1/1999 | Tajima et al. |
| 5,859,893 A | 1/1999 | Moorman et al. |
| 5,865,748 A | 2/1999 | Co et al. |
| 5,868,673 A | 2/1999 | Vesely |
| 5,873,822 A | 2/1999 | Ferre et al. |
| 5,876,328 A | 3/1999 | Fox et al. |
| 5,879,297 A | 3/1999 | Haynor et al. |
| 5,893,363 A | 4/1999 | Little et al. |
| 5,897,495 A | 4/1999 | Aida et al. |
| 5,899,860 A | 5/1999 | Pfeiffer et al. |
| 5,902,238 A | 5/1999 | Golden et al. |
| 5,907,487 A | 5/1999 | Rosenberg et al. |
| 5,908,385 A | 6/1999 | Chechelski et al. |
| 5,910,113 A | 6/1999 | Pruter |
| 5,910,120 A | 6/1999 | Kim et al. |
| 5,913,820 A | 6/1999 | Bladen et al. |
| 5,913,830 A | 6/1999 | Miles |
| 5,919,141 A | 7/1999 | Money et al. |
| 5,919,170 A | 7/1999 | Woessner |
| 5,928,145 A | 7/1999 | Ocali et al. |
| 5,929,607 A | 7/1999 | Rosenberg et al. |
| 5,931,788 A | 8/1999 | Keen et al. |
| 5,931,818 A | 8/1999 | Werp et al. |
| 5,941,858 A | 8/1999 | Johnson |
| 5,941,889 A | 8/1999 | Cermak |
| 5,941,904 A | 8/1999 | Johnston et al. |
| 5,944,022 A | 8/1999 | Nardella et al. |
| 5,944,023 A | 8/1999 | Johnson et al. |
| 5,953,683 A | 9/1999 | Hansen et al. |
| 5,957,857 A | 9/1999 | Hartley |
| 5,961,923 A | 10/1999 | Nova et al. |
| 5,967,978 A | 10/1999 | Littmann et al. |
| 5,967,980 A | 10/1999 | Ferre et al. |
| 5,967,991 A | 10/1999 | Gardineer et al. |
| 5,969,722 A | 10/1999 | Palm |
| 5,978,705 A | 11/1999 | KenKnight et al. |
| 5,983,126 A | 11/1999 | Wittkampf |
| 5,984,908 A | 11/1999 | Davis et al. |
| 5,991,693 A | 11/1999 | Zalewski |
| 5,997,473 A | 12/1999 | Taniguchi et al. |
| 5,997,481 A | 12/1999 | Adams et al. |
| 6,006,123 A | 12/1999 | Nguyen et al. |
| 6,011,988 A | 1/2000 | Lynch et al. |
| 6,014,473 A | 1/2000 | Hossack et al. |
| 6,014,580 A | 1/2000 | Blume et al. |
| 6,015,414 A | 1/2000 | Werp et al. |
| 6,017,496 A | 1/2000 | Nova et al. |
| 6,019,724 A | 2/2000 | Gronningsaeter et al. |
| 6,019,725 A | 2/2000 | Vesely et al. |
| 6,023,638 A | 2/2000 | Swanson |
| 6,026,312 A | 2/2000 | Shemwell et al. |
| 6,031,765 A | 2/2000 | Lee et al. |
| 6,032,070 A | 2/2000 | Flock et al. |
| 6,039,694 A | 3/2000 | Larson et al. |
| 6,050,718 A | 4/2000 | Schena et al. |
| 6,052,610 A | 4/2000 | Koch |
| 6,052,618 A | 4/2000 | Dahlke et al. |
| D424,693 S | 5/2000 | Pruter |
| 6,059,718 A | 5/2000 | Taniguchi et al. |
| 6,064,905 A | 5/2000 | Webster, Jr. et al. |
| 6,066,094 A | 5/2000 | Ben-Haim |
| 6,068,599 A | 5/2000 | Saito et al. |
| 6,073,043 A | 6/2000 | Schneider |
| 6,074,367 A | 6/2000 | Hubbell |
| 6,075,442 A | 6/2000 | Welch |
| 6,076,007 A | 6/2000 | England et al. |
| 6,082,366 A | 7/2000 | Andra et al. |
| 6,083,170 A | 7/2000 | Ben-Haim |
| 6,099,524 A | 8/2000 | Lipson et al. |
| 6,100,026 A | 8/2000 | Nova et al. |
| 6,102,044 A | 8/2000 | Naidyhorski |
| 6,107,699 A | 8/2000 | Swanson |
| 6,112,111 A | 8/2000 | Glantz |
| 6,113,504 A | 9/2000 | Kuesters |
| 6,115,624 A | 9/2000 | Lewis et al. |
| 6,120,445 A | 9/2000 | Grunwald |
| 6,128,174 A | 10/2000 | Ritter et al. |
| 6,129,668 A | 10/2000 | Haynor et al. |
| 6,132,378 A | 10/2000 | Marino |
| 6,132,379 A | 10/2000 | Patacsil et al. |
| 6,135,961 A | 10/2000 | Pflugrath et al. |
| 6,136,274 A | 10/2000 | Nova et al. |
| 6,138,681 A | 10/2000 | Chen et al. |
| 6,139,496 A | 10/2000 | Chen et al. |
| 6,139,502 A | 10/2000 | Fredriksen |
| 6,144,300 A | 11/2000 | Dames |
| 6,148,823 A | 11/2000 | Hastings |
| 6,152,933 A | 11/2000 | Werp et al. |
| 6,157,853 A | 12/2000 | Blume et al. |
| 6,165,144 A | 12/2000 | Talish et al. |
| 6,166,496 A | 12/2000 | Lys et al. |
| 6,166,806 A | 12/2000 | Tjin |
| 6,167,765 B1 | 1/2001 | Weitzel |
| 6,172,499 B1 | 1/2001 | Ashe |
| 6,173,199 B1 | 1/2001 | Gabriel |
| 6,173,715 B1 | 1/2001 | Sinanan et al. |
| 6,175,756 B1 | 1/2001 | Ferre et al. |
| 6,176,829 B1 | 1/2001 | Vilkomerson |
| 6,193,743 B1 | 2/2001 | Brayton et al. |
| 6,200,305 B1 | 3/2001 | Berthiaume et al. |
| 6,203,499 B1 | 3/2001 | Imling et al. |
| 6,208,884 B1 | 3/2001 | Kumar et al. |
| 6,211,626 B1 | 4/2001 | Lys et al. |
| 6,211,666 B1 | 4/2001 | Acker |
| 6,212,426 B1 | 4/2001 | Swanson |
| 6,216,027 B1 | 4/2001 | Willis et al. |
| 6,216,028 B1 | 4/2001 | Haynor et al. |
| 6,216,029 B1 | 4/2001 | Paltieli |

(56) References Cited

U.S. PATENT DOCUMENTS

| | | |
|---|---|---|
| 6,223,087 B1 | 4/2001 | Williams |
| 6,226,547 B1 | 5/2001 | Lockhart et al. |
| 6,230,046 B1 | 5/2001 | Crane et al. |
| 6,233,476 B1 | 5/2001 | Strommer et al. |
| 6,238,344 B1 | 5/2001 | Gamelsky et al. |
| 6,241,673 B1 | 6/2001 | Williams |
| 6,246,231 B1 | 6/2001 | Ashe |
| 6,246,898 B1 | 6/2001 | Vesely et al. |
| 6,248,072 B1 | 6/2001 | Murkin |
| 6,248,074 B1 | 6/2001 | Ohno et al. |
| 6,248,075 B1 | 6/2001 | McGee et al. |
| 6,253,770 B1 | 7/2001 | Acker et al. |
| 6,259,941 B1 | 7/2001 | Chia et al. |
| 6,261,231 B1 | 7/2001 | Damphousse et al. |
| 6,263,230 B1 | 7/2001 | Haynor et al. |
| 6,266,550 B1 | 7/2001 | Selmon et al. |
| 6,266,551 B1 | 7/2001 | Osadchy et al. |
| 6,266,552 B1 | 7/2001 | Slettenmark |
| 6,266,563 B1 | 7/2001 | KenKnight et al. |
| 6,271,833 B1 | 8/2001 | Rosenberg et al. |
| 6,272,371 B1 | 8/2001 | Shlomo |
| 6,272,374 B1 | 8/2001 | Flock et al. |
| 6,275,258 B1 | 8/2001 | Chim |
| 6,275,724 B1 | 8/2001 | Dickinson et al. |
| 6,277,077 B1 | 8/2001 | Brisken et al. |
| 6,284,459 B1 | 9/2001 | Nova et al. |
| 6,285,898 B1 | 9/2001 | Ben-Haim |
| 6,288,704 B1 | 9/2001 | Flack et al. |
| 6,292,678 B1 | 9/2001 | Hall et al. |
| 6,292,680 B1 | 9/2001 | Somogyi et al. |
| 6,292,901 B1 | 9/2001 | Lys et al. |
| 6,293,955 B1 | 9/2001 | Houser et al. |
| 6,296,604 B1 | 10/2001 | Garibaldi et al. |
| 6,298,261 B1 | 10/2001 | Rex |
| 6,304,768 B1 | 10/2001 | Blume et al. |
| 6,306,097 B1 | 10/2001 | Park et al. |
| 6,311,082 B1 | 10/2001 | Creighton, IV et al. |
| 6,315,709 B1 | 11/2001 | Garibaldi et al. |
| 6,315,727 B1 | 11/2001 | Coleman et al. |
| 6,319,668 B1 | 11/2001 | Nova et al. |
| 6,323,769 B1 | 11/2001 | Dames |
| 6,323,770 B1 | 11/2001 | Dames |
| 6,324,416 B1 | 11/2001 | Seibert |
| 6,325,540 B1 | 12/2001 | Lounsberry et al. |
| 6,325,762 B1 | 12/2001 | Tjin |
| 6,329,139 B1 | 12/2001 | Nova et al. |
| 6,329,916 B1 | 12/2001 | Dames |
| 6,330,467 B1 | 12/2001 | Creighton, IV et al. |
| 6,332,089 B1 | 12/2001 | Acker et al. |
| 6,332,874 B1 | 12/2001 | Eliasen et al. |
| 6,340,588 B1 | 1/2002 | Nova et al. |
| 6,340,868 B1 | 1/2002 | Lys et al. |
| 6,341,231 B1 | 1/2002 | Ferre et al. |
| 6,346,081 B1 | 2/2002 | Vilkomerson |
| 6,348,911 B1 | 2/2002 | Rosenberg et al. |
| 6,350,160 B1 | 2/2002 | Feuersanger et al. |
| 6,352,363 B1 | 3/2002 | Munger et al. |
| 6,355,026 B1 | 3/2002 | Mick |
| 6,361,499 B1 | 3/2002 | Bates et al. |
| 6,364,823 B1 | 4/2002 | Garibaldi et al. |
| 6,364,839 B1 | 4/2002 | Little et al. |
| 6,366,804 B1 | 4/2002 | Mejia |
| 6,368,285 B1 | 4/2002 | Osadchy et al. |
| 6,370,411 B1 | 4/2002 | Osadchy et al. |
| 6,373,240 B1 | 4/2002 | Govari |
| 6,373,388 B1 | 4/2002 | Dames |
| 6,374,134 B1 | 4/2002 | Bladen et al. |
| 6,374,670 B1 | 4/2002 | Spelman et al. |
| 6,375,606 B1 | 4/2002 | Garibaldi et al. |
| 6,375,639 B1 | 4/2002 | Duplessie et al. |
| 6,377,857 B1 | 4/2002 | Brayton et al. |
| 6,379,302 B1 | 4/2002 | Kessman et al. |
| 6,379,303 B1 | 4/2002 | Seitz et al. |
| 6,379,307 B1 | 4/2002 | Filly et al. |
| 6,381,485 B1 | 4/2002 | Hunter et al. |
| 6,385,472 B1 | 5/2002 | Hall et al. |
| 6,385,476 B1 | 5/2002 | Osadchy et al. |
| 6,398,736 B1 | 6/2002 | Seward |
| 6,401,723 B1 | 6/2002 | Garibaldi et al. |
| 6,406,442 B1 | 6/2002 | McFann et al. |
| 6,412,978 B1 | 7/2002 | Watanabe et al. |
| 6,412,980 B1 | 7/2002 | Lounsberry et al. |
| 6,417,839 B1 | 7/2002 | Odell |
| 6,418,332 B1 | 7/2002 | Mastrototaro et al. |
| 6,418,335 B2 | 7/2002 | Avrin et al. |
| 6,423,002 B1 | 7/2002 | Hossack |
| 6,423,050 B1 | 7/2002 | Twardowski |
| 6,427,079 B1 | 7/2002 | Schneider et al. |
| 6,428,551 B1 | 8/2002 | Hall et al. |
| 6,430,315 B1 | 8/2002 | Makram-Ebeid |
| 6,432,069 B1 | 8/2002 | Godo et al. |
| 6,438,411 B1 | 8/2002 | Guttman et al. |
| 6,442,416 B1 | 8/2002 | Schultz |
| 6,445,943 B1 | 9/2002 | Ferre et al. |
| 6,459,919 B1 | 10/2002 | Lys et al. |
| 6,463,121 B1 | 10/2002 | Milnes |
| 6,473,167 B1 | 10/2002 | Odell |
| 6,474,341 B1 | 11/2002 | Hunter et al. |
| 6,475,152 B1 | 11/2002 | Kelly, Jr. et al. |
| 6,475,223 B1 | 11/2002 | Werp et al. |
| 6,477,402 B1 | 11/2002 | Lynch et al. |
| 6,484,118 B1 | 11/2002 | Govari et al. |
| 6,487,916 B1 | 12/2002 | Gomm et al. |
| 6,491,671 B1 | 12/2002 | Larson, III et al. |
| 6,493,573 B1 | 12/2002 | Martinelli et al. |
| 6,496,715 B1 | 12/2002 | Lee et al. |
| 6,498,944 B1 | 12/2002 | Ben-Haim et al. |
| 6,500,141 B1 | 12/2002 | Irion et al. |
| 6,505,062 B1 | 1/2003 | Ritter et al. |
| 6,507,751 B2 | 1/2003 | Blume et al. |
| 6,508,802 B1 | 1/2003 | Rosengart et al. |
| 6,512,958 B1 | 1/2003 | Swoyer et al. |
| 6,514,249 B1 | 2/2003 | Maguire et al. |
| 6,515,657 B1 | 2/2003 | Zanelli |
| 6,516,212 B1 | 2/2003 | Bladen et al. |
| 6,516,231 B1 | 2/2003 | Flammang |
| 6,516,807 B1 | 2/2003 | Panescu et al. |
| 6,517,520 B2 | 2/2003 | Chang et al. |
| 6,522,906 B1 | 2/2003 | Salisbury, Jr. et al. |
| 6,522,907 B1 | 2/2003 | Bladen et al. |
| 6,522,909 B1 | 2/2003 | Garibaldi et al. |
| 6,524,303 B1 | 2/2003 | Garibaldi |
| 6,528,954 B1 | 3/2003 | Lys et al. |
| 6,528,991 B2 | 3/2003 | Ashe |
| 6,529,761 B2 | 3/2003 | Creighton, IV et al. |
| 6,534,982 B1 | 3/2003 | Jakab |
| 6,535,625 B1 | 3/2003 | Chang et al. |
| 6,537,192 B1 | 3/2003 | Elliott et al. |
| 6,537,196 B1 | 3/2003 | Creighton, IV et al. |
| 6,538,634 B1 | 3/2003 | Chui et al. |
| 6,540,699 B1 | 4/2003 | Smith |
| 6,542,766 B2 | 4/2003 | Hall et al. |
| 6,544,251 B1 | 4/2003 | Crawford |
| 6,546,270 B1 | 4/2003 | Goldin et al. |
| 6,546,279 B1 | 4/2003 | Bova et al. |
| 6,546,787 B1 | 4/2003 | Schiller et al. |
| 6,552,841 B1 | 4/2003 | Lasser et al. |
| 6,556,858 B1 | 4/2003 | Zeman |
| 6,562,019 B1 | 5/2003 | Sell |
| 6,564,087 B1 | 5/2003 | Pitris et al. |
| 6,569,101 B2 | 5/2003 | Quistgaard et al. |
| 6,571,004 B1 | 5/2003 | Florent et al. |
| 6,574,518 B1 | 6/2003 | Lounsberry et al. |
| 6,575,908 B2 | 6/2003 | Barnes et al. |
| 6,577,080 B2 | 6/2003 | Lys et al. |
| 6,577,896 B2 | 6/2003 | Werner et al. |
| 6,584,343 B1 | 6/2003 | Ransbury et al. |
| 6,593,754 B1 | 7/2003 | Steber et al. |
| 6,593,884 B1 | 7/2003 | Gilboa et al. |
| 6,597,943 B2 | 7/2003 | Taha et al. |
| 6,599,249 B1 | 7/2003 | Nordgren et al. |
| 6,607,488 B1 | 8/2003 | Jackson et al. |
| 6,610,058 B2 | 8/2003 | Flores |
| 6,611,141 B1 | 8/2003 | Schulz et al. |

(56) References Cited

U.S. PATENT DOCUMENTS

| | | |
|---|---|---|
| 6,615,071 B1 | 9/2003 | Casscells, III et al. |
| 6,615,155 B2 | 9/2003 | Gilboa |
| 6,618,612 B1 | 9/2003 | Acker et al. |
| 6,626,832 B1 | 9/2003 | Paltieli et al. |
| 6,626,834 B2 | 9/2003 | Dunne et al. |
| 6,626,902 B1 | 9/2003 | Kucharczyk et al. |
| 6,630,879 B1 | 10/2003 | Creighton, IV et al. |
| 6,635,027 B1 | 10/2003 | Cragg et al. |
| 6,645,148 B2 | 11/2003 | Nguyen-Dinh et al. |
| 6,648,875 B2 | 11/2003 | Simpson et al. |
| 6,649,914 B1 | 11/2003 | Moorman et al. |
| 6,652,506 B2 | 11/2003 | Bowe et al. |
| 6,662,034 B2 | 12/2003 | Segner et al. |
| 6,672,308 B1 | 1/2004 | Gaspari |
| 6,677,752 B1 | 1/2004 | Creighton, IV et al. |
| 6,679,857 B1 | 1/2004 | Bastia et al. |
| 6,684,176 B2 | 1/2004 | Willins et al. |
| 6,685,644 B2 | 2/2004 | Seo et al. |
| 6,687,531 B1 | 2/2004 | Ferre et al. |
| 6,689,119 B1 | 2/2004 | Di Caprio et al. |
| 6,690,963 B2 | 2/2004 | Ben-Haim et al. |
| 6,690,964 B2 | 2/2004 | Bieger et al. |
| 6,690,968 B2 | 2/2004 | Mejia |
| 6,694,167 B1 | 2/2004 | Ferre et al. |
| 6,695,786 B2 | 2/2004 | Wang et al. |
| 6,701,179 B1 | 3/2004 | Martinelli et al. |
| 6,701,918 B2 | 3/2004 | Fariss et al. |
| 6,702,804 B1 | 3/2004 | Ritter et al. |
| 6,704,590 B2 | 3/2004 | Haldeman |
| 6,709,390 B1 | 3/2004 | Marie Pop |
| 6,711,429 B1 | 3/2004 | Gilboa et al. |
| 6,711,431 B2 | 3/2004 | Pratt et al. |
| 6,719,699 B2 | 4/2004 | Smith |
| 6,719,724 B1 | 4/2004 | Walker et al. |
| 6,719,756 B1 | 4/2004 | Muntermann |
| 6,720,745 B2 | 4/2004 | Lys et al. |
| 6,733,511 B2 | 5/2004 | Hall et al. |
| 6,736,782 B2 | 5/2004 | Pfeiffer et al. |
| 6,738,656 B1 | 5/2004 | Ferre et al. |
| 6,740,103 B2 | 5/2004 | Hall et al. |
| 6,743,177 B2 | 6/2004 | Ito et al. |
| 6,754,596 B2 | 6/2004 | Ashe |
| 6,755,789 B2 | 6/2004 | Stringer et al. |
| 6,755,816 B2 | 6/2004 | Ritter et al. |
| 6,757,557 B1 | 6/2004 | Bladen et al. |
| 6,763,261 B2 | 7/2004 | Casscells, III et al. |
| 6,764,449 B2 | 7/2004 | Lee et al. |
| 6,768,496 B2 | 7/2004 | Bieger et al. |
| 6,772,001 B2 | 8/2004 | Maschke et al. |
| 6,774,624 B2 | 8/2004 | Anderson et al. |
| 6,783,536 B2 | 8/2004 | Vilsmeier et al. |
| 6,784,660 B2 | 8/2004 | Ashe |
| 6,785,571 B2 | 8/2004 | Glossop et al. |
| 6,786,219 B2 | 9/2004 | Garibaldi et al. |
| 6,788,967 B2 | 9/2004 | Ben-Haim et al. |
| 6,794,667 B2 | 9/2004 | Noshi |
| 6,799,066 B2 | 9/2004 | Steines et al. |
| 6,815,651 B2 | 11/2004 | Odell |
| 6,816,266 B2 | 11/2004 | Varshneya et al. |
| 6,817,364 B2 | 11/2004 | Garibaldi |
| 6,834,201 B2 | 12/2004 | Gillies et al. |
| 6,844,713 B2 | 1/2005 | Steber et al. |
| 6,845,142 B2 | 1/2005 | Ohishi |
| 6,856,823 B2 | 2/2005 | Ashe |
| 6,860,422 B2 | 3/2005 | Hull et al. |
| 6,862,467 B2 | 3/2005 | Moore et al. |
| 6,869,390 B2 | 3/2005 | Elliott et al. |
| 6,875,179 B2 | 4/2005 | Ferguson et al. |
| 6,879,160 B2 | 4/2005 | Jakab |
| 6,889,091 B2 | 5/2005 | Hine et al. |
| 6,895,268 B1 | 5/2005 | Rahn et al. |
| 6,902,528 B1 | 6/2005 | Garibaldi et al. |
| 6,908,433 B1 | 6/2005 | Pruter |
| 6,911,026 B1 | 6/2005 | Hall et al. |
| 6,923,782 B2 | 8/2005 | O'Mahony et al. |
| 6,926,673 B2 | 8/2005 | Roberts et al. |
| 6,934,575 B2 | 8/2005 | Ferre et al. |
| 6,936,010 B2 | 8/2005 | Fang et al. |
| 6,940,379 B2 | 9/2005 | Creighton |
| 6,941,166 B2 | 9/2005 | MacAdam et al. |
| 6,947,788 B2 | 9/2005 | Gilboa et al. |
| 6,950,689 B1 | 9/2005 | Willis et al. |
| 6,953,754 B2 | 10/2005 | Machida et al. |
| 6,958,677 B1 | 10/2005 | Carter |
| 6,959,214 B2 | 10/2005 | Pape et al. |
| 6,962,566 B2 | 11/2005 | Quistgaard et al. |
| 6,968,846 B2 | 11/2005 | Viswanathan |
| 6,975,197 B2 | 12/2005 | Creighton, IV |
| 6,976,962 B2 | 12/2005 | Bullis |
| 6,976,987 B2 | 12/2005 | Flores |
| 6,980,843 B2 | 12/2005 | Eng et al. |
| 6,980,852 B2 | 12/2005 | Jersey-Willuhn et al. |
| 6,980,921 B2 | 12/2005 | Anderson et al. |
| 6,986,739 B2 | 1/2006 | Warren et al. |
| 6,999,821 B2 | 2/2006 | Jenney et al. |
| 7,001,355 B2 | 2/2006 | Nunomura et al. |
| 7,008,418 B2 | 3/2006 | Hall et al. |
| 7,010,338 B2 | 3/2006 | Ritter et al. |
| 7,015,393 B2 | 3/2006 | Weiner et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| D518,574 S | 4/2006 | Chaggares |
| 7,022,075 B2 | 4/2006 | Grunwald et al. |
| 7,022,082 B2 | 4/2006 | Sonek |
| 7,026,927 B2 | 4/2006 | Wright et al. |
| 7,027,634 B2 | 4/2006 | Odell |
| 7,028,387 B1 | 4/2006 | Huynh et al. |
| 7,029,446 B2 | 4/2006 | Wendelken et al. |
| 7,033,603 B2 | 4/2006 | Nelson et al. |
| D520,139 S | 5/2006 | Chaggares |
| D520,140 S | 5/2006 | Chaggares |
| 7,038,398 B1 | 5/2006 | Lys et al. |
| 7,038,657 B2 | 5/2006 | Rosenberg et al. |
| 7,043,293 B1 | 5/2006 | Baura |
| 7,054,228 B1 | 5/2006 | Hickling |
| 7,066,914 B2 | 6/2006 | Andersen |
| 7,066,924 B1 | 6/2006 | Garibaldi et al. |
| D525,363 S | 7/2006 | Chaggares |
| 7,070,565 B2 | 7/2006 | Vaezy et al. |
| 7,072,704 B2 | 7/2006 | Bucholz |
| 7,082,325 B2 | 7/2006 | Hashimshony et al. |
| 7,090,639 B2 | 8/2006 | Govari |
| 7,096,148 B2 | 8/2006 | Anderson et al. |
| 7,096,870 B2 | 8/2006 | Lamprich et al. |
| 7,098,907 B2 | 8/2006 | Houston et al. |
| 7,103,205 B2 | 9/2006 | Wang et al. |
| 7,104,980 B1 | 9/2006 | Laherty et al. |
| 7,106,043 B1 | 9/2006 | Da Silva et al. |
| 7,106,431 B2 | 9/2006 | Odell |
| 7,106,479 B2 | 9/2006 | Roy et al. |
| 7,107,105 B2 | 9/2006 | Bjorklund et al. |
| 7,132,804 B2 | 11/2006 | Lys et al. |
| 7,137,976 B2 | 11/2006 | Ritter et al. |
| 7,141,812 B2 | 11/2006 | Appleby et al. |
| 7,142,905 B2 | 11/2006 | Slayton et al. |
| 7,148,970 B2 | 12/2006 | de Boer |
| 7,153,291 B2 | 12/2006 | Bierman |
| 7,161,453 B2 | 1/2007 | Creighton, IV |
| 7,162,291 B1 | 1/2007 | Nachaliel |
| 7,167,738 B2 | 1/2007 | Schweikard et al. |
| 7,169,107 B2 | 1/2007 | Jersey-Willuhn et al. |
| 7,174,201 B2 | 2/2007 | Govari et al. |
| 7,175,646 B2 | 2/2007 | Brenneman et al. |
| 7,180,252 B2 | 2/2007 | Lys et al. |
| 7,184,820 B2 | 2/2007 | Jersey-Willuhn et al. |
| 7,189,198 B2 | 3/2007 | Harburn et al. |
| 7,190,819 B2 | 3/2007 | Viswanathan |
| 7,194,295 B2 | 3/2007 | Vilsmeier |
| 7,204,798 B2 | 4/2007 | Zdeblick et al. |
| 7,206,064 B2 | 4/2007 | Rogers et al. |
| 7,207,941 B2 | 4/2007 | Sharf |
| 7,211,082 B2 | 5/2007 | Hall et al |
| 7,214,191 B2 | 5/2007 | Stringer et al. |

(56) References Cited

U.S. PATENT DOCUMENTS

| | | |
|---|---|---|
| 7,215,326 B2 | 5/2007 | Rosenberg |
| 7,221,104 B2 | 5/2007 | Lys et al. |
| 7,223,256 B2 | 5/2007 | Bierman |
| 7,229,400 B2 | 6/2007 | Elliott et al. |
| 7,231,243 B2 | 6/2007 | Tearney et al. |
| 7,236,157 B2 | 6/2007 | Schena et al. |
| 7,236,816 B2 | 6/2007 | Kumar et al. |
| 7,237,313 B2 | 7/2007 | Skujins et al. |
| 7,241,267 B2 | 7/2007 | Furia |
| 7,244,234 B2 | 7/2007 | Ridley et al. |
| 7,248,032 B1 | 7/2007 | Hular et al. |
| 7,248,914 B2 | 7/2007 | Hastings et al. |
| 7,264,584 B2 | 9/2007 | Ritter et al. |
| 7,270,662 B2 | 9/2007 | Visram et al. |
| 7,276,044 B2 | 10/2007 | Ferry et al. |
| 7,286,034 B2 | 10/2007 | Creighton |
| 7,291,146 B2 | 11/2007 | Steinke et al. |
| 7,297,140 B2 | 11/2007 | Orlu et al. |
| 7,308,296 B2 | 12/2007 | Lys et al. |
| 7,310,150 B2 | 12/2007 | Guillermo et al. |
| 7,321,228 B2 | 1/2008 | Govari |
| 7,342,058 B2 | 3/2008 | Peppmoller et al. |
| 7,355,716 B2 | 4/2008 | de Boer et al. |
| 7,360,427 B2 | 4/2008 | Drinkwater et al. |
| 7,366,376 B2 | 4/2008 | Shishkov et al. |
| 7,366,562 B2 | 4/2008 | Dukesherer et al. |
| 7,366,563 B2 | 4/2008 | Kleen et al. |
| 7,373,271 B1 | 5/2008 | Schneider |
| 7,382,949 B2 | 6/2008 | Bouma et al. |
| 7,418,169 B2 | 8/2008 | Tearney et al. |
| 7,447,408 B2 | 11/2008 | Bouma et al. |
| 7,452,331 B1 | 11/2008 | Pruter |
| 7,452,358 B2 | 11/2008 | Stern et al. |
| D585,556 S | 1/2009 | Kosaku |
| 7,479,141 B2 | 1/2009 | Kleen et al. |
| 7,534,223 B2 | 5/2009 | Boutilette et al. |
| 7,538,859 B2 | 5/2009 | Tearney et al. |
| 7,547,282 B2 | 6/2009 | Lo et al. |
| 7,551,293 B2 | 6/2009 | Yelin et al. |
| D603,050 S | 10/2009 | Chen |
| 7,599,730 B2 | 10/2009 | Hunter et al. |
| 7,635,336 B1 | 12/2009 | Pruter |
| 7,637,163 B2 | 12/2009 | Fetzer et al. |
| 7,640,053 B2 | 12/2009 | Verin |
| 7,651,469 B2 | 1/2010 | Osborne et al. |
| 7,652,080 B2 | 1/2010 | Peppmoller et al. |
| 7,665,893 B2 | 2/2010 | Buchalter |
| 7,668,583 B2 | 2/2010 | Fegert et al. |
| 7,699,782 B2 | 4/2010 | Angelsen et al. |
| 7,727,192 B2 | 6/2010 | Tokumoto et al. |
| 7,751,865 B2 | 7/2010 | Jascob et al. |
| 7,766,839 B2 | 8/2010 | Rogers et al. |
| 7,774,051 B2 | 8/2010 | Voth |
| 7,794,407 B2 | 9/2010 | Rothenberg |
| 7,798,970 B2 | 9/2010 | Lo et al. |
| 7,819,810 B2 | 10/2010 | Stringer et al. |
| D629,526 S | 12/2010 | Ladwig et al. |
| D629,527 S | 12/2010 | Crunkilton |
| 7,850,613 B2 | 12/2010 | Stribling |
| D630,756 S | 1/2011 | Kitayama |
| D630,757 S | 1/2011 | Kitayama |
| 7,909,815 B2 | 3/2011 | Whitmore, III et al. |
| 7,931,596 B2 | 4/2011 | Rachlin et al. |
| 7,976,469 B2 | 7/2011 | Bonde et al. |
| 8,118,743 B2 | 2/2012 | Park et al. |
| 8,388,541 B2 | 3/2013 | Messerly et al. |
| 8,388,546 B2 | 3/2013 | Rothenberg |
| 8,437,833 B2 | 5/2013 | Silverstein |
| D684,265 S | 6/2013 | Cadera |
| 8,478,382 B2 | 7/2013 | Burnside et al. |
| 8,512,256 B2 | 8/2013 | Rothenberg |
| 2002/0019447 A1 | 2/2002 | Renn et al. |
| 2002/0022777 A1 | 2/2002 | Crieghton et al. |
| 2002/0032391 A1 | 3/2002 | McFann et al. |
| 2002/0055680 A1 | 5/2002 | Miele et al. |
| 2002/0082559 A1 | 6/2002 | Chang et al. |
| 2002/0113555 A1 | 8/2002 | Lys et al. |
| 2002/0123679 A1 | 9/2002 | Dominguez |
| 2002/0128554 A1 | 9/2002 | Seward |
| 2002/0133079 A1 | 9/2002 | Sandhu |
| 2002/0156363 A1 | 10/2002 | Hunter et al. |
| 2002/0156376 A1 | 10/2002 | Wang et al. |
| 2002/0165448 A1 | 11/2002 | Ben-Haim et al. |
| 2002/0165534 A1 | 11/2002 | Hayzelden et al. |
| 2002/0198568 A1 | 12/2002 | Hafer et al. |
| 2003/0009132 A1 | 1/2003 | Schwartz et al. |
| 2003/0011359 A1 | 1/2003 | Ashe |
| 2003/0013966 A1 | 1/2003 | Barnes et al. |
| 2003/0036696 A1 | 2/2003 | Willis et al. |
| 2003/0040671 A1 | 2/2003 | Somogyi et al. |
| 2003/0072805 A1 | 4/2003 | Miyazawa et al. |
| 2003/0076281 A1 | 4/2003 | Morgan et al. |
| 2003/0083698 A1 | 5/2003 | Whitehurst et al. |
| 2003/0088195 A1 | 5/2003 | Vardi et al. |
| 2003/0100849 A1 | 5/2003 | Jang |
| 2003/0114742 A1 | 6/2003 | Lewkowicz et al. |
| 2003/0114777 A1 | 6/2003 | Griffin et al. |
| 2003/0120150 A1 | 6/2003 | Govari |
| 2003/0120154 A1 | 6/2003 | Sauer et al. |
| 2003/0139661 A1 | 7/2003 | Kimchy et al. |
| 2003/0149328 A1 | 8/2003 | Elliott et al. |
| 2003/0152290 A1 | 8/2003 | Odell |
| 2003/0160721 A1 | 8/2003 | Gilboa et al. |
| 2003/0163037 A1 | 8/2003 | Bladen et al. |
| 2003/0171691 A1 | 9/2003 | Casscells, III et al. |
| 2003/0173953 A1 | 9/2003 | Ashe |
| 2003/0184544 A1 | 10/2003 | Prudent |
| 2003/0191392 A1 | 10/2003 | Haldeman |
| 2003/0191460 A1 | 10/2003 | Hobbs et al. |
| 2003/0195420 A1 | 10/2003 | Mendlein et al. |
| 2003/0199746 A1 | 10/2003 | Fuimaono et al. |
| 2003/0208142 A1 | 11/2003 | Boudewijn et al. |
| 2003/0216639 A1 | 11/2003 | Gilboa et al. |
| 2003/0220557 A1 | 11/2003 | Cleary et al. |
| 2003/0220578 A1 | 11/2003 | Ho et al. |
| 2003/0229298 A1 | 12/2003 | Iwami et al. |
| 2003/0233042 A1 | 12/2003 | Ashe |
| 2004/0015070 A1 | 1/2004 | Liang et al. |
| 2004/0024301 A1 | 2/2004 | Hockett et al. |
| 2004/0030319 A1 | 2/2004 | Korkor et al. |
| 2004/0054278 A1 | 3/2004 | Kimchy et al. |
| 2004/0082916 A1 | 4/2004 | Jenkins |
| 2004/0087877 A1 | 5/2004 | Besz et al. |
| 2004/0088136 A1 | 5/2004 | Ashe |
| 2004/0097803 A1 | 5/2004 | Panescu |
| 2004/0097804 A1 | 5/2004 | Sobe |
| 2004/0097805 A1 | 5/2004 | Verard et al. |
| 2004/0097806 A1 | 5/2004 | Hunter et al. |
| 2004/0116809 A1 | 6/2004 | Chow et al. |
| 2004/0127805 A1 | 7/2004 | MacAdam et al. |
| 2004/0131998 A1 | 7/2004 | Marom et al. |
| 2004/0133111 A1 | 7/2004 | Szczech et al. |
| 2004/0133130 A1 | 7/2004 | Ferry et al. |
| 2004/0135069 A1 | 7/2004 | Odell |
| 2004/0138564 A1 | 7/2004 | Hwang et al. |
| 2004/0138570 A1 | 7/2004 | Nita et al. |
| 2004/0147837 A1 | 7/2004 | Macaulay et al. |
| 2004/0150963 A1 | 8/2004 | Holmberg et al. |
| 2004/0152972 A1 | 8/2004 | Hunter |
| 2004/0155609 A1 | 8/2004 | Lys et al. |
| 2004/0158140 A1 | 8/2004 | Fuimaono et al. |
| 2004/0171924 A1 | 9/2004 | Mire et al. |
| 2004/0176688 A1 | 9/2004 | Haldeman |
| 2004/0186461 A1 | 9/2004 | DiMatteo |
| 2004/0199069 A1 | 10/2004 | Connelly et al. |
| 2004/0210289 A1 | 10/2004 | Wang et al. |
| 2004/0230271 A1 | 11/2004 | Wang et al. |
| 2004/0234453 A1 | 11/2004 | Smith |
| 2004/0253365 A1 | 12/2004 | Warren et al. |
| 2004/0254470 A1 | 12/2004 | Drinkwater et al. |
| 2004/0260174 A1 | 12/2004 | Keene |
| 2004/0267086 A1 | 12/2004 | Anstadt et al. |
| 2005/0004450 A1 | 1/2005 | Ben-Haim et al. |
| 2005/0021019 A1 | 1/2005 | Hashimshony et al. |

(56) References Cited

U.S. PATENT DOCUMENTS

| | | |
|---|---|---|
| 2005/0033150 A1 | 2/2005 | Takahashi et al. |
| 2005/0038355 A1 | 2/2005 | Gellman et al. |
| 2005/0049486 A1 | 3/2005 | Urquhart et al. |
| 2005/0049510 A1 | 3/2005 | Haldeman et al. |
| 2005/0063194 A1 | 3/2005 | Lys et al. |
| 2005/0070788 A1 | 3/2005 | Wilson et al. |
| 2005/0075561 A1 | 4/2005 | Golden |
| 2005/0085716 A1 | 4/2005 | Hamm et al. |
| 2005/0085718 A1 | 4/2005 | Shahidi |
| 2005/0085720 A1 | 4/2005 | Jascob et al. |
| 2005/0101868 A1 | 5/2005 | Ridley et al. |
| 2005/0101869 A1 | 5/2005 | Burba et al. |
| 2005/0105081 A1 | 5/2005 | Odell |
| 2005/0105101 A1 | 5/2005 | Duling et al. |
| 2005/0112135 A1 | 5/2005 | Cormier et al. |
| 2005/0113669 A1 | 5/2005 | Helfer et al. |
| 2005/0113676 A1 | 5/2005 | Weiner et al. |
| 2005/0113700 A1 | 5/2005 | Yanagihara et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0149002 A1 | 7/2005 | Wang et al. |
| 2005/0151489 A1 | 7/2005 | Lys et al. |
| 2005/0154308 A1 | 7/2005 | Quistgaard et al. |
| 2005/0159644 A1 | 7/2005 | Takano |
| 2005/0159790 A1 | 7/2005 | Shalev |
| 2005/0165301 A1 | 7/2005 | Smith et al. |
| 2005/0165313 A1 | 7/2005 | Byron et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182295 A1 | 8/2005 | Soper et al. |
| 2005/0203368 A1 | 9/2005 | Verin |
| 2005/0203396 A1 | 9/2005 | Angelsen et al. |
| 2005/0205081 A1 | 9/2005 | Barker et al. |
| 2005/0215901 A1 | 9/2005 | Anderson et al. |
| 2005/0215945 A1 | 9/2005 | Harris et al. |
| 2005/0222532 A1 | 10/2005 | Bertolero et al. |
| 2005/0240102 A1 | 10/2005 | Rachlin et al. |
| 2005/0256398 A1 | 11/2005 | Hastings et al. |
| 2005/0256541 A1 | 11/2005 | Stypulkowski |
| 2006/0015003 A1 | 1/2006 | Moaddes et al. |
| 2006/0025677 A1 | 2/2006 | Verard et al. |
| 2006/0058633 A1 | 3/2006 | Hoshino et al. |
| 2006/0068074 A1 | 3/2006 | Stefandl |
| 2006/0084867 A1 | 4/2006 | Tremblay et al. |
| 2006/0116571 A1 | 6/2006 | Maschke et al. |
| 2006/0116578 A1 | 6/2006 | Grunwald et al. |
| 2006/0149134 A1 | 7/2006 | Soper et al. |
| 2006/0173329 A1 | 8/2006 | Irioka et al. |
| 2006/0173407 A1 | 8/2006 | Shaughnessy et al. |
| 2006/0176242 A1 | 8/2006 | Jaramaz et al. |
| 2006/0184074 A1 | 8/2006 | Vaezy et al. |
| 2006/0206037 A1 | 9/2006 | Braxton |
| 2006/0211944 A1 | 9/2006 | Mauge et al. |
| 2006/0224188 A1 | 10/2006 | Libbus et al. |
| 2006/0247746 A1 | 11/2006 | Danek et al. |
| 2006/0276867 A1 | 12/2006 | Viswanathan |
| 2007/0010753 A1 | 1/2007 | MacAdam |
| 2007/0016007 A1 | 1/2007 | Govari et al. |
| 2007/0016013 A1 | 1/2007 | Camus |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0049822 A1 | 3/2007 | Bunce et al. |
| 2007/0049846 A1 | 3/2007 | Bown et al. |
| 2007/0055141 A1 | 3/2007 | Kruger et al. |
| 2007/0055142 A1 | 3/2007 | Webler |
| 2007/0060992 A1 | 3/2007 | Pappone |
| 2007/0062544 A1 | 3/2007 | Rauk Bergstrom et al. |
| 2007/0073155 A1 | 3/2007 | Park et al. |
| 2007/0087038 A1 | 4/2007 | Richardson et al. |
| 2007/0093710 A1 | 4/2007 | Maschke |
| 2007/0100285 A1 | 5/2007 | Griffin et al. |
| 2007/0112282 A1 | 5/2007 | Skujins et al. |
| 2007/0123805 A1 | 5/2007 | Shireman et al. |
| 2007/0129770 A1 | 6/2007 | Younis |
| 2007/0135803 A1 | 6/2007 | Belson |
| 2007/0135886 A1 | 6/2007 | Maschke |
| 2007/0156205 A1 | 7/2007 | Larson et al. |
| 2007/0161915 A1 | 7/2007 | Desai |
| 2007/0167738 A1 | 7/2007 | Timinger et al. |
| 2007/0167801 A1 | 7/2007 | Webler et al. |
| 2007/0167997 A1 | 7/2007 | Forsberg et al. |
| 2007/0197905 A1 | 8/2007 | Timinger et al. |
| 2007/0208255 A1 | 9/2007 | Ridley et al. |
| 2007/0225589 A1 | 9/2007 | Viswanathan |
| 2007/0225610 A1 | 9/2007 | Mickley et al. |
| 2007/0232882 A1 | 10/2007 | Glossop et al. |
| 2007/0238984 A1 | 10/2007 | Maschke et al. |
| 2007/0239018 A1 | 10/2007 | Fetzer et al. |
| 2007/0244413 A1 | 10/2007 | Biggins |
| 2007/0247454 A1 | 10/2007 | Rahn et al. |
| 2007/0249911 A1 | 10/2007 | Simon |
| 2007/0265526 A1 | 11/2007 | Govari et al. |
| 2007/0280974 A1 | 12/2007 | Son et al. |
| 2007/0282196 A1 | 12/2007 | Birk et al. |
| 2007/0282197 A1 | 12/2007 | Bill et al. |
| 2007/0299352 A1 | 12/2007 | Harlev et al. |
| 2008/0008745 A1 | 1/2008 | Stinchcomb et al. |
| 2008/0009720 A1 | 1/2008 | Schefelker et al. |
| 2008/0015442 A1 | 1/2008 | Watson et al. |
| 2008/0027320 A1 | 1/2008 | Bolorforosh et al. |
| 2008/0045908 A1 | 2/2008 | Gould et al. |
| 2008/0051626 A1 | 2/2008 | Sato et al. |
| 2008/0081958 A1 | 4/2008 | Denison et al. |
| 2008/0082136 A1 | 4/2008 | Gaudiani |
| 2008/0097232 A1 | 4/2008 | Rothenberg |
| 2008/0108949 A1 | 5/2008 | Beasley et al. |
| 2008/0114095 A1 | 5/2008 | Peppmoller et al. |
| 2008/0125772 A1 | 5/2008 | Stone et al. |
| 2008/0139944 A1 | 6/2008 | Weymer et al. |
| 2008/0146939 A1 | 6/2008 | McMorrow et al. |
| 2008/0146940 A1 | 6/2008 | Jenkins et al. |
| 2008/0154100 A1 | 6/2008 | Thalmeier et al. |
| 2008/0166453 A1 | 7/2008 | Steele et al. |
| 2008/0171934 A1 | 7/2008 | Greenan et al. |
| 2008/0183075 A1 | 7/2008 | Govari et al. |
| 2008/0200754 A1 | 8/2008 | Buchalter |
| 2008/0228082 A1 | 9/2008 | Scheirer et al. |
| 2008/0255404 A1 | 10/2008 | Nogawa et al. |
| 2008/0255475 A1 | 10/2008 | Kondrosky et al. |
| 2008/0275765 A1 | 11/2008 | Kuchar |
| 2009/0005675 A1 | 1/2009 | Grunwald et al. |
| 2009/0018497 A1 | 1/2009 | Birchard et al. |
| 2009/0024018 A1 | 1/2009 | Boyden et al. |
| 2009/0043205 A1 | 2/2009 | Pelissier et al. |
| 2009/0082661 A1 | 3/2009 | Saladin et al. |
| 2009/0084382 A1 | 4/2009 | Jalde et al. |
| 2009/0101577 A1 | 4/2009 | Fulkerson et al. |
| 2009/0118612 A1 | 5/2009 | Grunwald et al. |
| 2009/0118706 A1 | 5/2009 | Schweikert et al. |
| 2009/0124901 A1 | 5/2009 | Fink et al. |
| 2009/0143736 A1 | 6/2009 | Mittermeyer et al. |
| 2009/0156926 A1 | 6/2009 | Messerly et al. |
| 2009/0163810 A1 | 6/2009 | Kanade et al. |
| 2009/0171217 A1 | 7/2009 | Kim et al. |
| 2009/0177083 A1 | 7/2009 | Matsumura |
| 2009/0177090 A1 | 7/2009 | Grunwald et al. |
| 2009/0203989 A1 | 8/2009 | Burnside et al. |
| 2009/0204113 A1 | 8/2009 | MacAdam et al. |
| 2009/0209950 A1 | 8/2009 | Starksen |
| 2009/0227952 A1 | 9/2009 | Blakstvedt et al. |
| 2009/0234328 A1 | 9/2009 | Cox et al. |
| 2009/0258171 A1 | 10/2009 | Uang |
| 2009/0259124 A1 | 10/2009 | Rothenberg |
| 2009/0262982 A1 | 10/2009 | Markowitz et al. |
| 2009/0275828 A1 | 11/2009 | Shachar et al. |
| 2009/0297441 A1 | 12/2009 | Canham et al. |
| 2010/0004543 A1 | 1/2010 | Ahlund et al. |
| 2010/0004547 A1 | 1/2010 | Scholz et al. |
| 2010/0016726 A1 | 1/2010 | Meier |

(56) References Cited

U.S. PATENT DOCUMENTS

| | | |
|---|---|---|
| 2010/0036227 A1 | 2/2010 | Cox et al. |
| 2010/0049062 A1 | 2/2010 | Ziv |
| 2010/0055153 A1 | 3/2010 | Majmudar |
| 2010/0055184 A1 | 3/2010 | Zeitels et al. |
| 2010/0057157 A1 | 3/2010 | Govari et al. |
| 2010/0060472 A1 | 3/2010 | Kimura et al. |
| 2010/0083719 A1 | 4/2010 | Peppmoller et al. |
| 2010/0094116 A1 | 4/2010 | Silverstein |
| 2010/0106011 A1 | 4/2010 | Byrd et al. |
| 2010/0114573 A1 | 5/2010 | Huang et al. |
| 2010/0143119 A1 | 6/2010 | Kooijman et al. |
| 2010/0185097 A1 | 7/2010 | Hall |
| 2010/0198048 A1 | 8/2010 | Togawa |
| 2010/0204569 A1 | 8/2010 | Burnside et al. |
| 2010/0217116 A1 | 8/2010 | Eck et al. |
| 2010/0222664 A1 | 9/2010 | Lemon et al. |
| 2010/0234733 A1 | 9/2010 | Wahlheim |
| 2010/0249598 A1 | 9/2010 | Smith et al. |
| 2010/0258033 A1 | 10/2010 | Yang et al. |
| 2010/0273895 A1 | 10/2010 | Stinchcomb et al. |
| 2010/0298702 A1 | 11/2010 | Rogers et al. |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0015527 A1 | 1/2011 | Heasty et al. |
| 2011/0015533 A1 | 1/2011 | Cox et al. |
| 2011/0040212 A1 | 2/2011 | Dietz et al. |
| 2011/0052694 A1 | 3/2011 | Stinchcomb et al. |
| 2011/0087107 A1 | 4/2011 | Lindekugel et al. |
| 2011/0196248 A1 | 8/2011 | Grunwald |
| 2011/0282188 A1 | 11/2011 | Burnside et al. |
| 2011/0295108 A1 | 12/2011 | Cox et al. |
| 2011/0313293 A1 | 12/2011 | Lindekugel et al. |
| 2012/0046562 A1 | 2/2012 | Powers et al. |
| 2012/0059270 A1 | 3/2012 | Grunwald |
| 2012/0095319 A1 | 4/2012 | Kondrosky et al. |
| 2012/0108950 A1 | 5/2012 | He et al. |
| 2012/0143029 A1 | 6/2012 | Silverstein et al. |
| 2012/0220854 A1 | 8/2012 | Messerly et al. |
| 2013/0006102 A1 | 1/2013 | Wilkes et al. |
| 2013/0060116 A1 | 3/2013 | Messerly et al. |

FOREIGN PATENT DOCUMENTS

| | | |
|---|---|---|
| AU | 20009592 | 9/2000 |
| AU | 20015250 | 6/2001 |
| AU | 768362 B2 | 12/2003 |
| AU | 2001229024 B2 | 9/2005 |
| AU | 2001283703 B2 | 5/2006 |
| AU | 2006202149 | 6/2006 |
| AU | 2006904933 | 9/2006 |
| AU | 2006283022 B2 | 2/2012 |
| CA | 2420676 | 2/2002 |
| CN | 1672649 A | 9/2005 |
| CN | 102209490 A | 10/2011 |
| CN | 102802514 A | 11/2012 |
| CN | 102821679 A | 12/2012 |
| CN | 103037761 A | 4/2013 |
| CN | 103037762 A | 4/2013 |
| CN | 103118591 A | 5/2013 |
| DE | 4319033 C1 | 6/1994 |
| EP | 0359697 | 3/1990 |
| EP | 0362821 | 4/1990 |
| EP | 0399536 A1 | 11/1990 |
| EP | 0823261 A2 | 2/1998 |
| EP | 0928976 A2 | 7/1999 |
| EP | 1311226 A1 | 5/2003 |
| EP | 1504713 A1 | 2/2005 |
| EP | 2313143 A1 | 4/2011 |
| EP | 2440122 A1 | 4/2012 |
| EP | 2464407 A2 | 6/2012 |
| EP | 2482719 A1 | 8/2012 |
| EP | 2575610 A1 | 4/2013 |
| EP | 2575611 A1 | 4/2013 |
| EP | 2603145 A2 | 6/2013 |
| EP | 2605699 A2 | 6/2013 |
| FR | 2545349 | 11/1984 |
| JP | 01097440 | 4/1989 |
| JP | 03173542 A | 7/1991 |
| JP | 4090741 | 8/1992 |
| JP | 9-503054 | 3/1997 |
| JP | 09-094298 A | 4/1997 |
| JP | 10043310 | 2/1998 |
| JP | 10290839 A | 11/1998 |
| JP | 11128237 A | 5/1999 |
| JP | 2001161683 | 6/2001 |
| JP | 2001340334 | 12/2001 |
| JP | 2003501127 A | 1/2003 |
| JP | 2003061752 A | 3/2003 |
| JP | 2003299654 | 10/2003 |
| JP | 2003334191 | 11/2003 |
| JP | 2002520893 | 2/2004 |
| JP | 2004505748 T | 2/2004 |
| JP | 2004515298 A | 5/2004 |
| JP | 2006508744 A | 3/2006 |
| JP | 5010604 | 6/2012 |
| JP | 2012-529929 | 11/2012 |
| JP | 2013-518676 A | 5/2013 |
| WO | 9112836 A1 | 9/1991 |
| WO | 9203090 | 3/1992 |
| WO | 9403159 A1 | 2/1994 |
| WO | 9404938 | 3/1994 |
| WO | 9605768 A1 | 2/1996 |
| WO | 9607352 A1 | 3/1996 |
| WO | 9641119 | 12/1996 |
| WO | 9729683 A1 | 8/1997 |
| WO | 9743989 A1 | 11/1997 |
| WO | 9916495 A1 | 4/1999 |
| WO | 9949407 A1 | 9/1999 |
| WO | 0019906 | 4/2000 |
| WO | 0040155 | 7/2000 |
| WO | 0074775 A1 | 12/2000 |
| WO | 0176479 A1 | 10/2001 |
| WO | 0215973 A1 | 2/2002 |
| WO | 0225277 A1 | 3/2002 |
| WO | 03061752 | 7/2003 |
| WO | 03077759 A1 | 9/2003 |
| WO | 2004094970 A2 | 6/2004 |
| WO | 2005033524 A1 | 4/2005 |
| WO | 2005033574 A1 | 4/2005 |
| WO | 2005117690 A1 | 12/2005 |
| WO | 2006074509 A1 | 7/2006 |
| WO | 2006074510 A1 | 7/2006 |
| WO | 2006078677 A2 | 7/2006 |
| WO | 2006103661 A2 | 10/2006 |
| WO | 2006111056 A1 | 10/2006 |
| WO | 2007002541 A1 | 1/2007 |
| WO | 2007005976 A1 | 1/2007 |
| WO | 2007014447 A1 | 2/2007 |
| WO | 2007034196 A2 | 3/2007 |
| WO | 2007067324 A1 | 6/2007 |
| WO | 2007069168 A2 | 6/2007 |
| WO | 2007109123 A2 | 9/2007 |
| WO | 2007126536 A2 | 11/2007 |
| WO | 2007144894 A1 | 12/2007 |
| WO | 2008005480 A1 | 1/2008 |
| WO | 2008024596 A2 | 2/2008 |
| WO | 2008028253 | 3/2008 |
| WO | 2008083111 | 7/2008 |
| WO | 2008118992 A1 | 10/2008 |
| WO | 2008126074 A2 | 10/2008 |
| WO | 2008131017 A2 | 10/2008 |
| WO | 2008136008 A2 | 11/2008 |
| WO | 2009002514 A2 | 12/2008 |
| WO | 2009009064 A1 | 1/2009 |
| WO | 2009057774 A1 | 5/2009 |
| WO | 2009070616 A2 | 6/2009 |
| WO | 2009100158 A1 | 8/2009 |
| WO | 2009123819 A2 | 10/2009 |
| WO | 2009126340 A1 | 10/2009 |
| WO | 2009129475 A1 | 10/2009 |
| WO | 2009129477 A1 | 10/2009 |
| WO | 2009134605 A2 | 11/2009 |

(56) References Cited

FOREIGN PATENT DOCUMENTS

| WO | 2009137262 A2 | 11/2009 |
|---|---|---|
| WO | 2010002313 A1 | 1/2010 |
| WO | 2010018500 A1 | 2/2010 |
| WO | 2010022370 A1 | 2/2010 |
| WO | 2010027349 A1 | 3/2010 |
| WO | 2010027471 A2 | 3/2010 |
| WO | 2010030820 A1 | 3/2010 |
| WO | 2010132857 A1 | 11/2010 |
| WO | 2010143196 A1 | 12/2010 |
| WO | 2010144922 A1 | 12/2010 |
| WO | 2011019760 A2 | 2/2011 |
| WO | 2011041450 A1 | 4/2011 |
| WO | 2011044421 A1 | 4/2011 |
| WO | 2011064209 A1 | 6/2011 |
| WO | 2011084593 A2 | 7/2011 |
| WO | 2011097312 A1 | 8/2011 |
| WO | 2011128052 A2 | 10/2011 |
| WO | 2011150358 A1 | 12/2011 |
| WO | 2012021542 A2 | 2/2012 |
| WO | 2012024577 A2 | 2/2012 |
| WO | 2012040487 | 3/2012 |
| WO | 2012058461 A1 | 5/2012 |
| WO | 2012083245 A1 | 6/2012 |
| WO | 2012088535 A1 | 6/2012 |
| WO | 2013006817 A1 | 1/2013 |

OTHER PUBLICATIONS

U.S. Appl. No. 11/466,602, filed Aug. 23, 2006 Non-Final Office Action dated Sep. 25, 2009.
U.S. Appl. No. 11/466,602, filed Aug. 23, 2006 Notice of Allowance dated Dec. 3, 2012.
U.S. Appl. No. 11/552,094, filed Oct. 23, 2006 Notice of Allowability dated Apr. 2, 2010.
U.S. Appl. No. 11/552,094, filed Oct. 23, 2006 Non-Final Office Action dated Apr. 27, 2009.
U.S. Appl. No. 11/552,094 filed Oct. 23, 2006 Notice of Allowance dated May 20, 2010.
U.S. Appl. No. 12/104,253, filed Apr. 16, 2008 Final Office Action dated Jul. 27, 2011.
U.S. Appl. No. 12/104,253, filed Apr. 16, 2008 Non-Final Office Action dated Nov. 29, 2010.
U.S. Appl. No. 12/323,273, filed Nov. 25, 2008 Non-Final Office Action dated Jun. 8, 2012.
U.S. Appl. No. 12/369,625, filed Feb. 11, 2009 Final Office Action dated Feb. 23, 2012.
U.S. Appl. No. 12/369,625, filed Feb. 11, 2009 Notice of Allowance dated Oct. 5, 2012.
U.S. Appl. No. 12/369,625, filed Feb. 11, 2009 Notice of Panel Decision dated Aug. 1, 2012.
U.S. Appl. No. 12/369,625, filed Feb. 11, 2009 Non-Final Office Action dated Jul. 20, 2011.
U.S. Appl. No. 12/426,175, filed Apr. 17, 2009 Non-Final Office Action dated Dec. 3, 2012.
U.S. Appl. No. 12/427,244, filed Apr. 21, 2009 Non-Final Office Action dated Jan. 19, 2012.
U.S. Appl. No. 12/545,762, filed Aug. 21, 2009 Non-Final Office Action dated Aug. 1, 2012.
U.S. Appl. No. 12/557,401, filed Sep. 10, 2009 Non-Final Office Action dated Apr. 24, 2012.
U.S. Appl. No. 12/575,456, filed Oct. 7, 2009 Non-Final Office Action dated Oct. 5, 2012.
U.S. Appl. No. 12/715,556, filed Mar. 2, 2010 Non-Final Office Action dated Sep. 13, 2012.
U.S. Appl. No. 12/878,915, filed Sep. 9, 2010 Final Office Action dated Sep. 26, 2012.
U.S. Appl. No. 12/878,915, filed Sep. 9, 2010 Non-Final Office Action dated Mar. 15, 2012.
U.S. Appl. No. 13/118,138, filed May 27, 2011 Non-Final Office Action dated Oct. 3, 2012.
U.S. Appl. No. 13/213,622, filed Aug. 19, 2011 Non-Final Office Action dated Jul. 31, 2012.
U.S. Appl. No. 13/336,919, filed Dec. 23, 2011 Non-Final Office Action dated Oct. 16, 2012.
Valdivieso, J.R. Perez, et al., Evaluation of a formula for optimal positioning of a central venous catheter inserted through the right internal jugular vein, Rev. Esp. Anestesiol. Reanim. 2003; 50: 77-79.
VasoNova Inc, Vascular navigation system for accurate placement of PICCs, Start-Up Emerging Medical Ventures, pp. 44-45, vol. 14 No. 7, Jul.-Aug. 2009.
Vesely, Thomas M. et al., Central Venous Catheter Tip Position: A Continuing Controversy, J Vasc Intery Radiol 2003; 14:527-534.
VIASYS Health Care Inc. Cortrak© Fact Sheet, 2005.
VIASYS Healthcare MedSystems, Navigator® Benefits, 2008.
VIASYS Healthcare MedSystems, Navigator® Research in Cost Justification, 2008.
VIASYS MedSystems, Cortrak™ Systems Brochure, 2005.
Volcano ComboMap Features and Benefits/Technical Specifications, 2 pages, 2011.
Watters, et al. "Use of Electrocardiogram to Position Right Atrial Catheters During Surgery." Annals of Surgery, vol. 225, No. 2, pp. 165-171, 1997.
Welch Allyn Cardioperfect® PC-Based Resting ECG, 2003.
Wilson, R. G. et al, Right Atrial Electrocardiography in Placement of Central Venous Catheters, The Lancet, pp. 462-463, Feb. 27, 1988.
Wong, Jeffrey J. et al., Azygos Tip Placement for Hemodialysis Catheters in Patients with Superior Vena Cava Occlusion, Cardiovasc Intervent Radiol (2006) 29:143-146.
Worley, Seth J. "Use of a Real-Time Three-Dimensional Magenetic Navigation System for Radiofrequency Ablation of Accessory Pathways." PACE, vol. 21 pp. 1636-1643, Aug. 1998.
Yilmazlar A et al, Complications of 1303 Central Venous Cannulations, J R Soc Med, pp. 319-321, vol. 90 No. 6, Jun. 1997 (Abstract only).
Yoon, SZ et al, Usefulness of the Carina as a Radiographic Landmark for Central Venous Catheter Placement in Paediatric Patients, Br J Anaesth, Jul. 2005.
Yoshida, Teruhisa et al, Detection of Concealed Left Sided Accessory Atrioventricular Pathway by P Wave Signal Averaged Electrocardiogram, J Am Coll Cardiol, pp. 55-62, 1999.
Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.
Zachariou, Zacharias et al., Intra-atrial ECG recording: a new and safe method for implantation of Broviac catheters in children, Pediatr Surg Int (1994) 9: 457-458.
MedGraphics, CardioPerfect® Resting/Stress ECG System, 3 pages, 2001.
Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.
Michenfelder, John et al, Air Embolism During Neurosurgery. A New Method of Treatment, Anesthesia and Analgesia. Current Researches, pp. 390-395, vol. 45, No. 4, Jul.-Aug. 1966.
MICROBIRD™ Miniaturized DC Magnetic Sensors for Intra-body Navigation and Localization, Specifications, 2005.
Micronix CathRite™ Cardiac Access Device Brochure. Jun. 2004.
Micronix Pty Ltd "CathRite" Guiding Styled Core Manufacturing, Jun. 15, 2006.
Murthy, Vrudhula et al, Analysis of Power Spectral Densities of Electrocardiograms, Mathematical Biosciences, pp. 41-51, vol. 12 No. 1-2, Oct. 1971.
Nadroo, AM et al, Changes in Upper Extremity Position Cause Migration of Peripherally Inserted Central Catheters in Neonates, Pediatrics, pp. 131-136, vol. 110, Jul. 2002.
Nakatani, K et al, Accurate Placement of Central Venous Catheters— ECG-guided method vs Patient Height Method, MASUI, pp. 34-38, vol. 51 No. 1, Jan. 2002.
Nazarian, GK et al, Changes in Tunneled Catheter Tip Position when a patient is Upright, J Vasc Intery Radio!, pp. 437-441, vol. 8 No. 3, May-Jun. 1997.
Neurometer® CPT, Clinical Applications. Neurotron , Inc. website: www.neurotron.com/CLINAPS.html, last accessed Oct. 23, 2006.

(56) References Cited

OTHER PUBLICATIONS

Neurometer® CPT, Frequently Asked Questions. Neurotron, Inc. website: www.neurotron.com/CPTFAQ/html, last accessed Oct. 23, 2006.
Neurometer® CPT, Products Page. Neurotron, Inc. website: www.neurotron.com/products.html, last accessed Oct. 23, 2006.
Neurometer® Electrodiagnostic Neuroselective Sensory Nerve Evaluation: Charts, Tables, Documents & Downloads. Neurotron, Inc. website: www.neurotron.com/downloads.html, last accessed Oct. 23, 2006.
Odd, De et al, Does Radio-opaque Contrast Improve Radiographic localisation of Percutaneous Central Venous Lines?, Arch Dis Child Fetal Neonatal Ed, pp. 41-43, vol. 89 No. 1, Jan. 2004.
Palesty, JA et al, Routine Chest Radiographs Following Central Venous Recatherization over a Wire are not Justified, Am J Surg, pp. 618-621, vol. 176 No. 6, Dec. 1998.
Paliotti, Roberta P. et al, Intravascular Doppler Technique for Monitoring Renal Venous Blood Flow in Man, J Nephrol, pp. 57-62, 2003.
Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.
Pawlik, et al., "Central Venous Catheter Placement: Comparison of the Intravascular Guidewire and the Fluid Column Electrocardiograms." European Journal of Anaesthesiology, vol. 41, pp. 594-599, 2004.
PCT/US2006/033079 filed Aug. 24, 2006 International Preliminary Report on Patentability dated Feb. 26, 2008.
PCT/US2006/033079 filed Aug. 24, 2006 Search Report dated Dec. 19, 2006.
PCT/US2006/033079 filed Aug. 24, 2006 Written Opinion dated Dec. 19, 2006.
PCT/US2008/060502 filed Apr. 16, 2008 International Search Report and Written Opinion dated Oct. 16, 2008.
PCT/US2008/084751 filed Nov. 25, 2008 International Preliminary Report on Patentability dated Jun. 1, 2010.
PCT/US2008/084751 filed Nov. 25, 2008 Search Report dated May 20, 2009.
PCT/US2008/084751 filed Nov. 25, 2008 Written Opinion dated May 20, 2009.
PCT/US2009/033116 filed Feb. 4, 2009 International Preliminary Report on Patentability dated Aug. 10, 2010.
PCT/US2009/033116 filed Feb. 4, 2009 Search Report dated Mar. 13, 2009.
PCT/US2009/033116 filed Feb. 4, 2009 Written Opinion dated Mar. 13, 2009.
PCT/US2009/041051 filed Apr. 17, 2009 Search Report dated Jul. 28, 2009.
PCT/US2009/041051 filed Apr. 17, 2009 Written Opinion dated Jul. 28, 2009.
PCT/US2009/054687 filed Aug. 21, 2009 International Preliminary Report on Patentability dated Feb. 22, 2011.
PCT/US2009/054687 filed Aug. 21, 2009 Search Report dated Oct. 6, 2009.
PCT/US2009/054687 filed Aug. 21, 2009 Written Opinion dated Oct. 6, 2009.
PCT/US2009/056567 filed Sep. 10, 2009 International Preliminary Report on Patentability dated Mar. 15, 2011.
PCT/US2009/056567 filed Sep. 10, 2009 Search Report dated Nov. 6, 2009.
PCT/US2009/056567 filed Sep. 10, 2009 Written Opinion dated Nov. 6, 2009.
PCT/US2010/038555 filed Jun. 14, 2010 Search Report dated Oct. 5, 2010.
PCT/US2010/038555 filed Jun. 14, 2010 Written Opinion dated Oct. 5, 2010.
PCT/US2010/045084 filed Aug. 10, 2010 International Preliminary Report on Patentability dated Feb. 23, 2012.
PCT/US2010/045084 filed Aug. 10, 2010 Search Report dated Apr. 14, 2011.
PCT/US2010/045084 filed Aug. 10, 2010 Written Opinion dated Apr. 14, 2011.
PCT/US2010/050773 filed Sep. 29, 2010 Search Report dated Jan. 24, 2011.
PCT/US2010/050773 filed Sep. 29, 2010 Written Opinion dated Jan. 24, 2011.
PCT/US2010/051917 filed Oct. 8, 2010 Search Report dated Nov. 29, 2010.
PCT/US2010/051917 filed Oct. 8, 2010 Written Opinion dated Nov. 29, 2010.
PCT/US2011/023497 filed Feb. 2, 2011 Search Report dated Jun. 6, 2011.
PCT/US2011/023497 filed Feb. 2, 2011 Written Opinion dated Jun. 6, 2011.
PCT/US2011/038391 filed May 27, 2011 International Preliminary Report on Patentability and Written Opinion dated Dec. 4, 2012.
PCT/US2011/038391 filed May 27, 2011 International Search Report dated Sep. 21, 2011.
AU 2008329807 exam requested Aug. 13, 2012 Examination Report No. 1 dated Feb. 15, 2013.
CN 200880125528.4 filed Nov. 25, 2008 Second Office Action dated Mar. 6, 2013.
CN 200980123021.X filed Dec. 17, 2010 First Office Action dated Nov. 19, 2012.
CN 200980144663.8 filed May 9, 2011 First Office Action dated Dec. 5, 2012.
EP 09808901.4 filed Aug. 21, 2009 Examination Report dated May 10, 2013.
EP 09813632.8 filed Apr. 5, 2011 Office Action dated Apr. 30, 2013.
EP 12177438.4 filed Jul. 23, 2012 European Search Report dated Dec. 4, 2012.
EP 12177438.4 filed Jul. 23, 2012 extended European Search Report dated Mar. 25, 2013.
PCT/US2011/038415 filed May 27, 2011 International Preliminary Report on Patentability dated Dec. 13, 2012.
PCT/US2011/047127 filed Aug. 9, 2011 International Preliminary Report on Patentability dated Apr. 18, 2013.
PCT/US2011/052793 filed Sep. 22, 2011 International Preliminary Report on Patentability dated Apr. 4, 2013.
U.S. Appl. No. 11/466,602, filed Aug. 23, 2006 Non-Final Office Action dated Mar. 28, 2013.
U.S. Appl. No. 12/545,762, filed Aug. 21, 2009 Final Office Action dated Mar. 7, 2013.
U.S. Appl. No. 12/854,083, filed Aug. 10, 2010 Non-Final Office Action dated Jan. 29, 2013.
U.S. Appl. No. 12/878,915, filed Sep. 9, 2010 Notice of Allowance dated Jan. 8, 2013.
U.S. Appl. No. 13/118,138, filed May 27, 2011 Final Office Action dated Apr. 3, 2013.
U.S. Appl. No. 13/213,622, filed Aug. 19, 2011 Final Office Action dated Feb. 19, 2013.
U.S. Appl. No. 13/283,395, filed Oct. 27, 2011 Non-Final Office Action dated Apr. 23, 2013.
U.S. Appl. No. 13/336,919, filed Dec. 23, 2011 Advisory Action dated May 23, 2013.
U.S. Appl. No. 13/336,919, filed Dec. 23, 2011 Final Office Action dated Mar. 1, 2013.
U.S. Appl. No. 13/337,987, filed Dec. 27, 2011 Non-Final Office Action dated Mar. 15, 2013.
AU 2011289513 filed Jan. 21, 2013 Examiners Report dated Jul. 5, 2013.
AU 2012202293 filed Apr. 19, 2012 Examination Report No. 1 dated Apr. 24, 2013.
AU 2013204243 filed Apr. 12, 2013 Examiner's Report dated Jun. 5, 2013.
CN 200880012117.4 filed Apr. 16, 2008 Third Office Action dated Apr. 27, 2013.
CN 200880125528.4 filed Nov. 25, 2008 Third Office Action dated Jul. 1, 2013.
EP 08855396.1 filed Jun. 15, 2010 Intent to Grant dated Jul. 5, 2013.
EP 09707467.8 supplemental European search report dated Jun. 18, 2013.

(56) References Cited

OTHER PUBLICATIONS

JP 2010-504220 filed Sep. 3, 2009 Final Office Action dated Apr. 18, 2013.
PCT/US2011/058138 filed Oct. 27, 2011 International Preliminary Report on Patentability dated May 10, 2013.
PCT/US2011/067268 filed Dec. 23, 2011 International Preliminary Report on Patentability dated Jul. 4, 2013.
U.S. Appl. No. 12/900,750, filed Oct. 8, 2010 Non-Final Office Action dated Jun. 3, 2013.
U.S. Appl. No. 29/428,649, filed Aug. 1, 2012 Notice of Allowance dated Jul. 5, 2013.
Cullinane, DC et al, The Futility of Chest Roentgenograms Following Routine Central Venous Line Changes, Am J Surg, pp. 283-285, vol. 176 No. 3, Sep. 1998.
Curet, Myriam J. et al., University and Practice-based Physicians' Input on the Content of a Surgical Curriculum, The American Journal of Surgery® vol. 178 Jul. 1999, 78-84.
David, et al., "Is ECG-Guidance a Helpful Method to Correctly Position a Central Venous Catheter During Prehospital Emergency Care?" ACTA Anaesthesiologica Scandinavica, vol. 49, pp. 1010-1014, 2005.
Deltec Cath-Finder® Tracking System Operation Manual, 1994.
Egelhof, Petra, Effects of Somatostatin on Portal Blood Flow and Portal Vein Pressure in Patients with Portal Hypertension due to Liver Cirrhosis Invasive Monitoring during TIPSS Procedures, Dissertation submitted to: Technical University of Munich, Faculty of Medicine, May 13, 2002; Date of examination: Feb. 26, 2003.
Engelhardt, W et al, ECG-Controlled Placement of Central Venous Catheters in Patients with Atrial Fibrallation, Anaesthesist, pp. 476-479, vol. 38 No. 9, Sep. 1989 (Abstract only).
EP 08855396.1 filed Jun. 15, 2010 European Search Report dated Jul. 31, 2012.
EP 09808901.4 filed Aug. 21, 2009 European Search Report dated May 23, 2012.
EP 09813632.8 filed Apr. 5, 2011 European Search Report dated Jul. 4, 2012.
Fearon, William F et al, Evaluating Intermediate Coronary Lesions in the Cardiac Catheterization Laboratory, vol. 4, No. 1, 7 pages, Reviews in Cardiovascular Medicine, 2003.
Felleiter P et al, Use of Electrocardiographic Placement Control of Central Venous Catheters in Austria, Acta Med Austriaca, pp. 109-113, vol. 26 No. 3, 1999 (Abstract only).
Forauer, AR et al, Change in Peripherally Inserted Central Catheter Tip Location with Abduction and Adduction of the Upper Extremity, J Vasc Intery Radiol, pp. 1315-1318, vol. 11 No. 10, Nov.-Dec. 2000.
Frassinelli, P et al, Utility of Chest Radiographs after Guidewire Exchanges of Central Venous Catheters, Crit Care Med, pp. 611-615, vol. 26 No. 3, Mar. 1998.
Frazin L et al, A Doppler Guided Retrograde Catheterization System, Cathet. Cardiovasc Diagn, pp. 41-50, May 1992.
French, PJ et al, Sensors for Catheter Applications, Sensors Update, vol. 13 Issue 1 pp. 107-153, Dec. 2003.
GB Application 0800474.9 filed Aug. 24, 2006 Office Action dated Aug. 9, 2010.
GB Application 0800474.9 filed Aug. 24, 2006 Office Action dated Mar. 17, 2010.
Gebauer, B et al, Ultrasound and Fluoroscopy-guided Implantation of Peripherally Inserted Central Venous Catheters (PICCs), ROFO, pp. 386-391, vol. 176 No. 3, Mar. 2004 (Abstract only).
Gebhard, et al., "The accuracy of Electrocardiogram-Controlled Central Line Placement." The International Anesthesia Research Society, vol. 104, No. 1 Jan. 2007.
Gjendemsjo, Anders, et al., Energy and Power, The Connexions Project, Version 1.2, Feb. 20, 2004.
Gladwin, MT et al, Cannulation of the Internal Jugular Vein: is postpocedural chest radiography always necessary?, Crit Care Med, 33 pages, Oct. 2000.
Gonzales, et al. "Peripherally Inserted Central Catheter Placement in Swine Using Magnet Detection." Journal of Intravenous Nursing, vol. 22, No. 3, May/Jun. 1999.
Greenall, M.J. et al, Cardiac Tamponade and Central Venous Catheters, British Medical Journal, pp. 595-597, Jun. 14, 1975.
Guillory, "Basic Principles of Technologies for Catheter Localization." C.R. Bard internal paper, Oct. 20, 2004.
Guth, AA, Routine Chest X-rays after Insertion of Implantable Long-Term Venous Catheters: Necessary or Not?, Am Surg, pp. 26-29, vol. 67 No. 1, Jan. 2001 (Abstract only).
Hill, Bradley et al, Abstract of article discussing VasaNova VPS as guide for placement of PICCs. 2009.
Hill, Bradley, Identifying the Caval-Atrial Junction Using Smart-Catheter Technology presentation, 22nd Annual Scientific Meeting of the AVA in Savannah, Georgia, Sep. 13, 2008.
Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.
Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.
Iacopino, Domenico Gerardo et al, Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.
Joosting, Jean-Pierre, "Dual-interface RFID-compatible EEPROM enables remote access to electronic device parameters," EE Times, Mar. 8, 2010.
JP 2008-528151 filed Aug 24, 2006 Notice of Grant dated May 6, 2012.
JP 2010-504220 filed Sep. 3, 2009 Office Action dated May 21, 2012.
Kim, Ko et al, Positioning Internal Jugular Venous Catheters using the Right Third Intercostal Space in Children, Acta Anaesthesiol Scand, pp. 1284-1286, vol. 47 No. 10, Nov. 2003.
Kjelstrup T et al, Positioning of Central Venous Catheters using ECG, Tidssk nor Laegeforen, pp. 599-601, vol. 111 No. 5, Feb. 1999 (Abstract only).
Kofler, Julia, et al., Epinephrine application via an endotracheal airway and via the Combitube in esophageal position, Critical Care Medicine: May 2000, vol. 28: Issue 5, pp. 1445-1449.
Konings, MK, et al., Development of an intravascular impedance catheter for detection of fatty lesions in arteries, IEEE Trans Med Imaging Aug. 1997; 16(4):439-46.
Kowalski, CM et al, Migration of Central Venous Catheters: Implications for Initial Catheter Tip Positioning, J Vasc Intery Radiol, pp. 443-447, vol. 8 No. 3, May-Jun. 1997.
Leowenthal, MR et al, The Peripherally Inserted Central Catheter (PICC): A Prospective Study of its Natural History after Fossa Insertion, Anaesth Intensive Care, pp. 21-24; vol. 30 No. 1, Feb. 2002.
Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.
Liu , Ji-Bin et al, Catheter-Based Intraluminical Sonography, J Ultrasound Med, pp. 145-160, vol. 23, 2004.
Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No. 5, Sep.-Oct. 1999.
Lum, Phillip, A New Formula-Based Measurement Guide for Optimal Positioning of Central Venous Catheters, JAVA, vol. 9, No. 2, pp. 80-85, 2004.
Lynch, RE et al, A Procedure for Placing Pediatric Femoral Venous Catheter Tips near the Right Atrium, Pediatr Emerg Care, pp. 130-132, vol. 18 No. 2, Apr. 2002.
Madan, et al. "Right Atrial Electrocardiography: A Technique for the Placement of Central Venous Catheters for Chemotherapy or Intravenous Nutrition." British Journal of Surgery, vol. B1, pp. 1604-1605, 1994.
Madias, John E, Intracardiac (Superior Vena Cava/Right Atrial) ECGs using Saline Solution as the Conductive Medium for the

(56) References Cited

OTHER PUBLICATIONS

Proper Positioning of the Shiley Hemodialysis Catheter: Is it Not Time to Forego the Postinsertion Chest Radiograph?, pp. 2363-2367, Chest, 2003.
Markovich, Mary B., Central Venous Catheter Tip Placement: Determination of Posterior Malposition—A Case Study, Java, vol. 11, No. 2, pp. 85-89, 2006.
Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.
McDonnall, "Intra-Atrial Electrocardiography (ECG) for Catheter Placement." Literature review prepared for Bard Access Systems, Oct. 2007.
McGee et al., "Accurate Placement of Central Venous Catheters: A Prospective, Randomize, Multicenter Trail." Critical Care Medicine, vol. 21 No. 8, Aug. 1993.
PCT/US2011/038415 filed May 27, 2011 International Search Report dated Sep. 28, 2011.
PCT/US2011/038415 filed May 27, 2011 Written Opinion dated Sep. 28, 2011.
PCT/US2011/047127 filed Aug. 9, 2011 International Search Report dated Feb. 29, 2012.
PCT/US2011/047127 filed Aug. 9, 2011 Written Opinion dated Feb. 29, 2012.
PCT/US2011/048403 filed Aug. 19, 2011 International Search Report dated Dec. 15, 2011.
PCT/US2011/048403 filed Aug. 19, 2011 Written Opinion dated Dec. 15, 2011.
PCT/US2011/052793 filed Sep. 22, 2011 International Search Report dated Jan. 6, 2012.
PCT/US2011/052793 filed Sep. 22, 2011 Written Opinion dated Jan. 6, 2012.
PCT/US2011/058138 filed Oct. 27, 2011 International Search Report dated Feb. 7, 2012.
PCT/US2011/058138 filed Oct. 27, 2011 Written Opinion dated Feb. 7, 2012.
PCT/US2011/067268 filed Dec. 23, 2011 International Search Report and Written Opinion dated Apr. 27, 2012.
PCT/US2012/045814 filed Jul. 6, 2012 International Search Report and Written Opinion dated Oct. 1, 2012.
Pennington, C.R., Right Atrial Thrombus: a Complication of Total Parenteral Nutrition, British Medical Journal, pp. 446-447, vol. 295, Aug. 15, 1987.
Petersen, J et al, Silicone Venous Access Devices Positioned with their Tip High in the Superior Vena Cava are More Likely to Malfunction, Am J Surg, pp. 38-41, vol. 178 No. 1, Jul. 1999.
Pittiruti, et al, Intracavitary EKG Monitoring: A reliable method for controlling tip position during and after PICC Insertion presentation in Catholic University, Rome, Italy in 2008.
Pittiruti, et al. "The EKG Method for Positioning the Tip of PICCs: Results from Two Preliminary Studies." JAVA, vol. 13, No. 4, pp. 179-185, 2008.
Polos, PG et al, Tips for Monitoring the Position of a Central Venous Catheter—How Placement can go awry—even when the anatomy is normal, J Crit Illn, pp. 660-674, vol. 8 No. 6, Jun. 1993 (Abstract only).
Pop, Gheorghe A. et al., Catheter-based impedance measurements in the right atrium for continuously monitoring hematocrit and estimating blood viscosity changes; an in vivo feasibility study in swine, Biosensors and Bioelectronics 19 (2004) 1685-1693.
Popp, M. B. et al., Accuracy of implanted port placement with the use of the electromagnetic CathTrack® catheter locator system, The Journal of Vascular Access 2005; 6: 9-12.
Randolph AG et al, Ultrasound guidance for placement of central venous catheters: a meta-analysis of the literature, Critcal Care Medicine, pp. 2053-2058, vol. 24, Dec. 1996.
Reece, A et al, Posititioning Long Lines: Contrast Versus Plain Radiography, Arch Dis Child Fetal Neonatal Ed, pp. 129-130, vol. 84 No. 2, Mar. 2001.
Reynolds, N et al, Assessment of Distal Tip Position of Long Term Central Venous Feeding Catheters using Transesophageal Echocardiology, JPEN J Parenter Enteral Nutr, pp. 39-41, vol. 25 No. 1, Jan.-Feb. 2001.
Ruschulte, Heiner et al, Prevention of Central Venous Catheter related infections with chlorhex idine gluconate impregnated wound dressings: A randomized controlled trial, presented as an abstract at the Annual meeting of the European Society of Anaesthesiologists (ESA) in Madrid, Spain in Jun. 2006, 12 pages, Annals of Hematology, Jul. 14, 2008.
Rutherford, J. S. et al., Depth of Central Venous Catheterization: An Audit of Practice in a Cardiac Surgical Unit, Anaesth Intens Care 1994; 22: 267-271.
Sacolick, et al. "Electromagnetically Tracked Placement of a Peripherally Inserted Central Catheter." SPIE Medical Imaging, 2004 Proceedings.
Salem, et al. "A New Peripherally Implanted Subcutaneous Permanent Central Venous Access Device for Patients Requiring Chemotherapy." Journal of Clinical Oncology, vol. 11, No. 11, pp. 2181-2185, Nov. 1993.
Savary, D et al, Intra-atrial Monitoring to Add Insertion of a Central Venous Line in Pre-Hospital Emergency Care Journal Europeen des Urgences, pp. 75-78, vol. 17 No. 2, 2004.
Schafer et al. "Incorrect placement of a vena cava catheter and its prevention by intra-atrial ECG." Anaesthesist. Jan. 1988;37(1):49-51.
Schummer, et al. "Central Venous Catheters—The inability of 'intra-atrial ECG' to prove adequate positioning." British Journal of Anaesthesia, vol. 93, No. 2, pp. 193-198, 2004.
Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).
Schummer, W et al, Intra-Atrial ECG is not a Reliable Method for Positioning Left Internal Jugular Vein Catheters, Br J Anaesth, pp. 481-486, vol. 91 No. 4, Oct. 2003.
Schummer, W, Central Venous Catheter—the Inability of "Intra-Atrial ECG" to prove Adequate Positioning, Br J Anaesth, pp. 193-198, vol. 93 No. 2, Aug. 2004.
Schuster, M. et al., The carina as a landmark in central venous catheter placement, British Journal of Anaesthesia 85 (2): 192-4 (2000).
Siela, Debra, Using Chest Radiography in the Intensive Care Unit, Crit Care Nurse Aug. 1, 2002 vol. 22 No. 4, pp. 18-27.
Simon, et al., "Central Venous Catheter Placement in Children: Evaluation of Electrocardiography Using J-Wire." Paediatric Anaesthesia vol. 9, pp. 501-504, 1999.
Smith, Brigham, et al., Intravenous electrocardiographic guidance for placement of peripherally inserted central catheters, Journal of Electrocardiology 43 (2010) 274-278.
Stark, DD et al, Radiographic Assessment of Venous Catheter Position in Children: Value of the Lateral View, Pediatric Radiology, pp. 76-80, vol. 14 No. 2, 1984.
Starkhammar et al. "Cath-Finder Catheter Tracking System: A New Device for Positioning of Central Venous Catheters. Early Experience from Implantation of Brachial portal Systems." Acta Anaesthesiol Scandinavia, vol. 34, No. 4 pp. 296-300, May 1990.
Starkhammer, H et al, Central Venous Catheter Placement using Electromagnetic Position Sensing: A Clinical Evaluation, Biomed. Instrum Technol, vol. 30 No. 2, pp. 164-170; Mar.-Apr. 1996.
Starr, David S et al, EKG Guided Placement of Subclavian CVP Catheters Using J-Wire, pp. 673-676, Ann. Surg, Dec. 1986.
Stas, M et al, Peroperative Intravasal Electrographic Control of Catheter Tip Position in Access Ports Placed by Venous Cut-Down Technique, EJSP, pp. 316-320, vol. 27, 2001.
Stereotaxis Magetic Navigation System with Navigant™ User Interface, 2005 Brochure.
Stereotaxis, Expanding the Possibilites of Interventional Medicine: Remote Navigation and Automation, pp. 1-8, Apr. 2011.
Tepa® Health Innovation PC based ECG System Introduction and Technical Specifications, EKG Master Usb, 2 pages, Nov. 2003.
The FloWire Doppler Guide Wire located <http://www.volcanocorp.com/products/flowire-doppler-guide-wire.php>, 2011.

(56) References Cited

OTHER PUBLICATIONS

Traxal Technologies, Tracking Technology website overview: www.traxal.com/rd/rd_classroom_trackingtechnology.htm, last accessed Dec. 1, 2006.
UAB Health Systems, Arrhythmias, retrieved from http://www.health,uab.edu/14564/ on Nov. 15, 2007, 12 pages.
U.S. Appl. No. 11/466,602, filed Aug. 23, 2006 Advisory Action dated Jun. 22, 2009.
U.S. Appl. No. 11/466,602, filed Aug. 23, 2006 Appeal Board Decision dated Sep. 17, 2012.
U.S. Appl. No. 11/466,602, filed Aug. 23, 2006 Final Office Action dated Apr. 8, 2010.
"Ascension to Launch New 3D Guidance™ Tracker at TCT 2006." Press Releases from Ascension website: www.ascension-tech.com/news/press_101106.php, last accessed Dec. 1, 2006.
Acuson—The Value of Vision, AcuNav Diagnostic Ultrasound Catheter, 2000.
Advertising flyer for GAVECELT—The Italian Group for Long Term Venous Access Devices, for program on International Meeting on PICC's, Midline Catheters and Long Term Venous Access Devices in Catholic University, Rome, Italy on Dec. 3, 4, 5, 2008.
Alexander, GD et al, The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.
Allan, P.L. et al, Role of Ultrsound in the Assessment of Chronic Venous Insufficiency, Ultrasound Quarterly, vol. 17, No. 1, pp. 3-10, 2001.
Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.
Anonymous author, Correct Catheter Placement with a low-impact, reliable and economical method, <http://www.cvc-partner.com/index.cfm?103A955CC6844BF58ACFE3C9C1471959>, last accessed Dec. 22, 2011.
Arai, J et al, Detection of Peripherally Inserted Central Catheter Occlusion by in-line Pressure Monitoring, Paediatr Anaesth, pp. 621-624, vol. 12 No. 7, Sep. 2002.
Arrow International, Inc., The Arrow-Johans RAECG Adapter—Making Proper Central Venous Catheter Placement More Reliable (Modle No. EG-04900), Technical Report 1987, USA.
Aslamy, et al. "MRI of Central Venous Anatomy: Implications for Central Venous Catheter Insertion." American College of Chest Physicians, Jun. 8, 2009.
AU 2006283022 filed Aug. 24, 2006 Office Action dated Dec. 22, 2010.
Aurora® System Technical Specifications, Oct. 2003.
B. Braun Website, "The Optimal Position of the Central Venous Catheter." http://www.cvcpartner.com/index.cfm18F1BDEA1310466194960A39F4E90968 (2009).
B. Braun, Certofix Central Venous Catheter for Placement Using the Seldinger Technique with Simultaneous ECG Lead Option, Feb. 2010.
Bailey, SH et al, Is Immediate Chest Radiograph Necessary after Central Venous Catheter Placement in a Surgical Intensive Care Unit?, Am J Surg, pp. 517-522, vol. 180 No. 6, Dec. 2000.
Bankier, Alexander A., Azygos Arch Cannulation by Central Venous Catheters: Radiographic Detection of Malposition and Subsequent Complications, Journal of Thoracic Imaging 12:64-69 (1997).
Barber, JMm et al, A Nurse led Peripherally Inserted Central Catheter Line Insertion Service is Effective with Radiological Support, Clin Radiol, pp. 352-354, vol. 57 No. 5, May 2002.
Bard Access Systems, Sherlock Tip Location System, 5 pages, 2006.
Bard Access Systems, Site Rite Vascular Acess Ultrasound System, 4 pages, 2005.

Benchimol, Alberto at al, Right Atrium and Superior Vena Cava Flow Velocity in Man Measured with the Doppler-Catheter Flowmeter-Telemetry System, The Amer Journal of Medicine, pp. 303-309, vol. 48, Mar. 1970.
BioAdvance Lumen Vu, Greenhouse Fund Feb. 2004 Recipient, www.bioadvance.com <http://www.bioadvance.com>, 2005.
Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.
Buehrle, Douglas, PICC Placement in Humans using Electromagnetic Detection, <http://www.corpakmedsystems.com/supplement_material/supplementpages/navigator/navarticle.html>, 2008.
C.R. Bard, CathTrack™ Catheter Location System at www.bardaccess.com <http://www.bardaccess.com>, last accessed Apr. 28, 2011.
C.R. Bard, Inc., Bard Electrophysiology Product Catalogue, Bard Catheters, pp. 74-75 (2002), USA.
CA 2,619,909 filed Aug. 24, 2006 Examiner's Report dated Oct. 26, 2012.
Cadman, A et al, To Clot or Not to Clot? That is the question in Central Venous Catheters, Clinical Radiology, pp. 349-355, vol. 59 No. 4, Apr. 2004.
Calvert, N et al, The Effectiveness and Cost-effectiveness of Ultrasound Locating Devices for Central Venous Access: A Systematic Review and Economic Evaluation, Health Technology Assessment, vol. 7, No. 12, 2003.
Cardella, John F. et al., Interventinal Radiologic Placement of Peripherally Inserted Central Catheters, Journal of Vascular and Interventional Radiology 1993; 4:653-660.
Carlon, R et al, Secondary Migration of a Central Venous Catheter—A Case Report, Minerva Anestesiol, pp. 927-931, vol. 69 No. 12, Dec. 2003.
Caruso, LJ et al, A Better Landmark for Positioning a Central Venous Catheter, J Clinical Monitoring and Computing, pp. 331-334, vol. 17 No. 6, Aug. 2002.
Cavatorta, et al., "Central Venous Catheter Placement in Hemodialysis: Evaluation of Electrocardiography Using a Guidewire." The Journal of Vascular Access, vol. 2, pp. 45-50, 2001.
Chalkiadis, GA et al, Depth of Central Venous Catheter Insertion in Adults: An Audit and Assessment of a Technique to Improve Tip Position, Anaesth Intensive Care, pp. 61-66, vol. 26 No. 1, Feb. 1998.
Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.
Chang, Thomas C. et al., Are Routine Ch Ladiographs Necessary After Image-Guided Placement of Internal Jugular Central Venous Access Devices?, AJR Feb. 1998;170:335-337.
Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.
Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.
Cheng, Ki et al, A Novel Approach of Intravenous Electrocardiograph Technique in Correct Position the Long-Term Central Venous Catheter, Kaohsiung J Med Sci, pp. 241-247, vol. 16 No. 5, May 2000 (Abstract only).
Cheung, P., et al., The Effect of a Disposable Probe Cover on Pulse Oximetry, Anaesth Intensive Care 2002; 30: 211-214.
Chu, et al., "Accurate Central Venous Port-A Catheter Placement: Intravenous Electrocardiography and Surface Landmark Techniques Compared by Using Transesophageal Echocardiography." The International Anesthesia Research Society, vol. 98, pp. 910-914, 2004.
Claasz, Antonia et al, A Study of the Relationship of the Superior Vena Cava to the Bony Landmarks of the Sternum in the Supine Adult: Implications for Magnetic Guidance Systems, Journal, vol. 12 No. 3, JAVA, Jul. 24, 2007.
Clifford, et al. "Assessment of Hepatic Motion Secondary to Respiration for Computer Assisted Interventions." Computer Aided Surgery, vol. 7, pp. 291-299, 2002.

(56) References Cited

OTHER PUBLICATIONS

CN 200880012117.4 filed Apr. 16, 2008 First Office Action dated Dec. 23, 2011.
CN 200880012117.4 filed Apr. 16, 2008 Second Office Action dated Oct. 8, 2012.
CN 200880125528.4 filed Nov. 25, 2008 First Office Action dated Jun. 5, 2012.
Colley, Peter S et al, ECG-Guided Placement of Sorenson CVP Catheters via Arm Veins, Anesthesia and Analgesia, pp. 953-956, vol. 63, 1984.
Collier, PE et al, Cardiac Tamponade from Central Venous Catheters, Am J Surg, pp. 212-214, vol. 176 No. 2, Aug. 1998.
ComboWire® Pressure/Flow Guide Wire Ref 9500 Series, Instructions for Use, Apr. 2011.
Corsten, et al., "Central Placement Catheter Placement Using the ECG-Guided Cavafix-Certodyn SD Catheter." Journal of Clinical Anesthesiology, vol. 6, Nov./Dec. 1994.
Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.

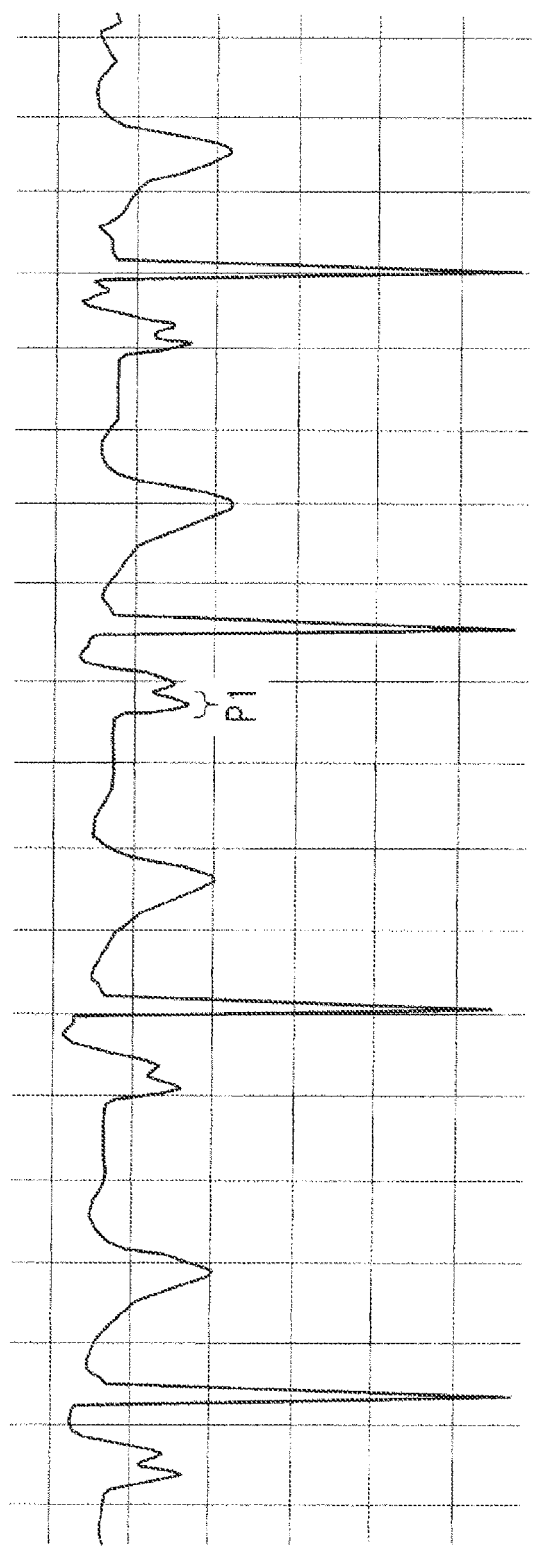

METHOD OF LOCATING THE TIP OF A CENTRAL VENOUS CATHETER

CROSS REFERENCE TO RELATED APPLICATION(S)

This application is a division of U.S. patent application Ser. No. 12/427,244, which is: 1) a continuation of International Application No. PCT/US2009/033116, filed Feb. 4, 2009, claiming priority under 35 U.S.C. §119(e) to U.S. Provisional Application No. 61/026,372, filed Feb. 5, 2008; and 2) a continuation-in-part of U.S. patent application Ser. No. 11/552,094, filed Oct. 23, 2006, now U.S. Pat. No. 7,794,407. Each of the aforementioned applications is incorporated by reference in its entirety into this application.

BACKGROUND OF THE INVENTION

1. Field of the Invention

The present invention is directed generally to devices for and methods of locating a catheter inside a body and more particularly to devices for and methods of locating the tip of a central venous catheter inside the superior vena cava, right atrium, and/or right ventricle using information obtained from an electrocardiogram.

2. Description of the Related Art

Central venous catheters ("CVC") include any catheter designed to utilize the central veins (e.g., subclavian and superior vena cava) or right sided cardiac chambers for the delivery and/or withdrawal of blood, blood products, therapeutic agents, and/or diagnostic agents. CVCs also include catheters inserted into the central veins or right sided cardiac chambers for the acquisition of hemodynamic data. Standard central venous catheters for intravenous access, dialysis catheters, percutaneously introduced central catheters ("PICC" lines), and right heart ("Swan-Ganz™") catheters are examples of CVCs.

The standard of care for placing a CVC (other than right heart catheters which generally terminate in the pulmonary artery) dictates that the tip of the CVC lie just above and not inside the right atrium. In fact, in 1989, the Food and Drug Administration issued a warning citing an increased risk of perforation of the right atrium, clot formation, and arrhythmias among other potential complications resulting from the tip of the CVC being placed inside the right atrium.

While CVCs have been used for many years, determining the position of the tip of the CVC has always been problematic. Currently, a chest x-ray is used to determine the position of the tip of the CVC. Because CVC may be a radiopaque and/or include radiopaque materials, the CVC is visible on an x-ray. However, this method has several drawbacks. For example, obtaining a chest x-ray is labor intensive and expensive. In recent years, CVCs, which were traditionally placed in a hospital in-patient setting, are being placed in an outpatient setting more frequently. In an outpatient setting, obtaining a chest x-ray to determine the position of the tip of the CVC can be very cumbersome and may not be obtained in a timely manner. Therefore, using a chest x-ray to determine the position of the tip of the CVC may introduce a considerable delay, prolonging the procedure. Generally, the operator will leave the patient to perform other duties while the x-ray is processed. If the tip is improperly placed, the operator must return to the patient's bedside to reposition the CVC. To reposition the CVC, the operator must open the sterile dressing, cut the sutures, re-suture, and redress the wound, all of which potentially expose the patient to discomfort and infection.

Recently, navigational systems principally used to guide peripherally placed lines have become available. Based upon the detection of magnetic fields between a stylet tip and a detector, these systems assume (and depend upon) a relationship between surface landmarks and anatomic locations. Unfortunately, these systems cannot be used to determine the location of the tip of a CVC with sufficient accuracy because the relationship between surface landmarks and anatomic locations is highly variable from one patient to another.

In addition to the need to know where the tip is during initial placement, the CVC may migrate or otherwise move after the initial placement and require re-positioning. Therefore, the operator must monitor or periodically reevaluate the location of the tip.

An electrocardiogram ("ECG") measures electrical potential changes occurring in the heart. Referring to FIGS. 1A-1C, the ECG measurements may be visualized or displayed as an ECG trace, which includes ECG waveforms. As is appreciated by those of ordinary skill in the art, ECG waveforms are divided into portions that include a QRS complex portion and a P wave portion in addition to other wave portions. The QRS complex corresponds to the depolarization of the ventricular muscle. The P wave portion of the ECG waveforms represents atrial muscle depolarization: the first half is attributable to the right atrium and the second half to the left atrium. Under normal circumstances, atrial muscle depolarization is initiated by a release of an excitatory signal from the sino-atrial ("SA") node, a specialized strip of tissue located at the juncture of the superior vena cava ("SVC") and right atrium.

As is appreciated by those of ordinary skill in the art, an ECG may be obtained using different electrode configurations. For example, a standard configuration referred to as "Lead II" may used. In a bipolar Lead II configuration, one of the electrodes (the cathode) is attached to the left leg and the other electrode (the anode) is attached to the right shoulder. As is appreciated by those of ordinary skill in the art, using a different configuration could change the polarity and/or the shape of the P wave. Other standard bipolar configurations include a bipolar Lead I configuration where the cathode is attached to the left shoulder and the anode is attached to the right shoulder and a bipolar Lead III configuration where the cathode is attached to the left leg and the anode is attached to the right shoulder.

The waveforms depicted in FIGS. 1A-1C and 2B were obtained using the anode of a standardized bipolar ECG Lead II configuration attached to the right shoulder and the tip of the CVC as the cathode. While technically this configuration is not a standard Lead II configuration, the trace produced by the electrodes 114A and 114B may be displayed on a standard ECG monitor using the monitor's circuitry to display the trace as a bipolar Lead II trace.

Techniques of using ECG waveforms to locate the tip of a CVC have been available since the 1940's. Some of these prior art devices construct an intravascular ECG trace by placing an electrode near the tip of the CVC and using that electrode to measure the voltage near the tip of the CVC relative to a surface electrode(s) and/or a second electrode spaced from the first.

These techniques have shown that both the magnitude and shape of the P wave change depending upon the positioning or location of the electrode attached to the tip of the CVC. Referring to FIGS. 1A and 1B, two exemplary ECG traces are provided for illustrative purposes.

FIG. 1A is an ECG trace made when the electrode attached to the tip of the CVC is in the proximal SVC. This tip location corresponds to position "1" depicted in FIG. 2A. The portion of the ECG trace corresponding to an exemplary P wave produced when the electrode attached to the tip is located in position "1" is labeled "P1."

FIG. 1B is an ECG trace made when the electrode attached to the tip of the CVC is approaching the SA node and stops at a location adjacent to the SA node. These tip locations correspond to moving the tip from a position "2" to position "3" depicted in FIG. 2A. The portion of the ECG trace corresponding to an exemplary P wave produced when the electrode attached to the tip is approaching the SA node is labeled "P2" and the portion of the ECG trace corresponding to an exemplary P wave produced when the electrode attached to the tip is located adjacent to the SA node is labeled "P3."

Normally as the electrode attached to the tip of the CVC moves from the proximal SVC (position "1") toward the SA node (position "3"), the maximum value of the absolute value of the voltage of the P wave increases dramatically. When the electrode attached to the tip of the CVC is adjacent to the SA node (position "3"), the voltage of the P wave (please see "P3" of FIG. 1B) reaches a maximum value that is more than twice the value experienced in the proximal SVC and may be as large as eight times the voltage in the proximal SVC. When this occurs, the tip of the CVC is considered to have entered into the right atrium. Because the magnitude of the P wave more than doubles when the electrode attached to the tip of the CVC is adjacent to the SA node, this information may be used to place the tip of the CVC within a few centimeters (e.g., about 1 cm to about 2 cm) proximal to the SA node. Additionally, as the electrode attached to the tip of the CVC moves from the proximal SVC toward the right atrium, the shape of the P wave changes from a "u" shape (FIG. 1A) to a spike-like shape (FIG. 1B).

Referring to FIG. 2B, another exemplary illustration of the P wave portion of the ECG trace produced when the electrode attached to the tip of the CVC is located at positions 1-5 depicted in FIG. 2A is provided. The P wave portions of the ECG traces of FIG. 2B are labeled with the letter "P" and occur between the vertical dashed lines. Each of the exemplary traces is numbered to correspond to positions "1" through "5." Therefore, the ECG trace "1" was produced when the electrode attached to the tip was located in the proximal SVC. The trace "2" was produced when the electrode attached to the tip was in position "2" (distal SVC). The trace "3" was produced when the electrode attached to the tip was adjacent to the SA node.

As the electrode attached to the tip of the CVC is advanced further into the right atrium, the polarity of the P wave "P" changes from predominantly negative near the top of the right atrium (position "3") to isoelectric (i.e., half has a positive polarity and half has a negative polarity) near the middle of the right atrium (position "4") to almost entirely positive at the bottom of the right atrium (position "5"). These changes in the P wave "P" are illustrated in traces "3" through "5."

FIG. 1C is an ECG trace made when the electrode attached to the tip of the CVC is in the right ventricle. The portion of the ECG trace corresponding to an exemplary P wave produced when the electrode attached to the tip is labeled "P6." When the electrode attached to the tip of the CVC is advanced into the right ventricle, the maximum magnitude of the absolute value of the P wave "P6" approximates the maximum magnitude of the absolute value of the P wave "P1" when the electrode attached to the tip of the CVC was inside the proximal SVC above the SA node (i.e., located at position "1"). However, the polarity of the first half of P wave "P6," which corresponds to the right atrium, is opposite.

The first technique developed for viewing the ECG waveform during the insertion of a CVC used a column of saline disposed within a hollow tube or lumen longitudinally traversing the CVC. The column of saline provides a conductive medium. Saline was inserted into the lumen by a saline filled syringe with a metal needle. The needle of the syringe remained within the entrance to the lumen or port in contact with the column of saline after the lumen was filled. One end of a double-sided alligator clip was attached to the needle and the other end was attached to an ECG lead, which in turn was attached to an ECG monitor. By using the saline solution filled CVC as a unipolar electrode and a second virtual electrode generated by ECG software from three surface electrodes, an intravascular ECG was obtained. The operator would adjust the position of the tip of the CVC based on the magnitude and shape of the P wave displayed by the ECG monitor.

Subsequently, this technique was modified by substituting an Arrow-Johans adapter for the metal needle. The Arrow-Johans adapter is a standard tubing connector with an embedded conductive ECG eyelet. The Arrow-Johans adapter may be placed in line with any conventional CVC. In a closed system, the tubing and CVC may be filled with saline, i.e., a conductive medium, and the CVC used as a unipolar electrode in conjunction with surface electrodes and a standard ECG monitor. The ECG eyelet is placed in contact with the saline in the lumen of the CVC. One end of the ECG lead is attached to the ECG eyelet and the other end to the ECG monitor for displaying the intravascular ECG waveforms. Because the system must be closed to prevent the saline from leaking out, this system works best after the guide wire used to thread the CVC forward has been withdrawn, i.e., after placement has been completed. Therefore, although the catheter may be withdrawn after initial placement, it may not be advanced into proper position.

B. Braun introduced its Certofix catheter to be used in conjunction with its CERTODYN adapter. In this system, a patch lead with two ends has an alligator clip connected to one end. The alligator clip is clipped to the CVC guide wire. The other end of the patch lead includes a connector that is plugged into the CERTODYN adapter. The ECG may be obtained during placement and the catheter may be advanced or withdrawn as desired. However, the CERTODYN adapter has many moving parts and is not sterile, making the procedure cumbersome to perform and the operative field more congested. Additionally, the sterile field may become contaminated by the non-sterile equipment.

The Alphacard, manufactured by B. Braun, merges the Arrow-Johans adapter and the CERTODYN adapter. The Alphacard consists of a saline filled syringe (used to flush the CVC with saline) and a connector to the CERTODYN. The Alphacard is used to obtain a 'snapshot' of the ECG trace from the saline column. If an atrial spike is seen in the ECG trace, the CVC is withdrawn.

With respect to all of these prior art methods of using an ECG trace to place the tip of the CVC, some degree of expertise is required to interpret the P waves measured because the user must advance the guide wire slowly and watch for changes in the P wave. If the catheter is inserted too far too quickly and the changes to the P wave go unnoticed (i.e., the operator fails to notice the increase or spike in the voltage experienced when the electrode attached to the tip is in the right atrium), the operator may mistakenly believe the tip is in the SVC when, in fact, the tip is in the right ventricle. If this occurs, advancing the tip may injure the patient.

U.S. Pat. Nos. 5,078,678 and 5,121,750 both issued to Katims teach a method of using the P wave portion of an ECG trace to guide placement of the tip of the CVC. The CVC includes two empty lumens into which a transmission line is fed or an electrolyte is added. Each of the lumens has a distal exit aperture located near the tip of the CVC. The two exit apertures are spaced from one another. In this manner, two spaced apart electrodes or a single anode/cathode pair are constructed near the tip of the CVC. The voltage or potential of one of the electrodes relative to the other varies depending upon the placement of the electrodes. The voltage of the electrodes is conducted to a catheter monitoring system. The catheter monitoring system detects increases and decreases in the voltage of the P wave. The voltage increases as the electrodes approach the SA node and decrease as the electrodes move away from the SA node. Based on whether the voltage is increasing or decreasing, the operator is instructed by messages on a screen to advance or withdraw the CVC.

While Katims teaches a method of locating the tip of a CVC relative to the SA node, Katims relies on advancing or withdrawing the CVC and observing the changes of the P wave. Katims does not disclose a method of determining the location of the tip of the CVC based on a single stationary position. Unless the entire insertion procedure is monitored carefully, the method cannot determine the position of the tip of the CVC. Further, the Katims method may be unsuitable for determining the location of a previously positioned stationary tip.

Other devices such as Bard's Zucker, Myler, Gorlin, and CVP/Pacing Lumen Electrode Catheters are designed primarily to pace. These devices include a pair of electrodes at their tip that are permanently installed and designed to contact the endocardial lining. These devices include a lumen, which may be used to deliver and/or withdraw medications or fluids as well as for pressure monitoring. These leads are not designed for tip location and do not include multi-lumen capability.

A method of obtaining an intravascular ECG for the purposes of placing a temporary pacing wire was described in U.S. Pat. No. 5,666,958 issued to Rothenberg et al. Rothenberg et al. discloses a bipolar pacing wire having a distal electrode. The distal electrode serves as a unipolar electrode when the pacing wire is inserted into the chambers of the heart. The pacing wire is connected to a bedside monitor through a specialized connector for the purposes of displaying the ECG waveforms detected by the distal electrode.

Given the volume of CVCs placed yearly and the increasing demand particularly for PICC lines (devices that permit the delivery of intravenous therapeutic agents in the outpatient setting, avoiding the need for hospitalization) a great need exists for methods and devices related to locating the tip of a CVC. Particularly, devices and methods are needed that are capable of determining the location of the tip before the operator leaves the bedside of the patient. Further, a method of determining the location (SVC, right atrium, or right ventricle) of the tip from a single data point rather than from a series of data points collected as the catheter is moved may be advantageous. Such a system may be helpful during initial placement and/or repositioning. A need also exists for a device for or a method of interpreting the ECG waveforms that does not require specialized expertise. Methods and devices that avoid the need for hospital and x-ray facilities are also desirable. A need also exists for devices and methods related to determining the position of the tip of the CVC that are less expensive, expose patients to fewer risks, and/or are less cumbersome than the x-ray method currently in use.

BRIEF DESCRIPTION OF THE SEVERAL VIEWS OF THE DRAWING(S)

FIG. 1A is an exemplary ECG trace obtained from an electrode placed inside the proximal SVC.

Figure 1B:
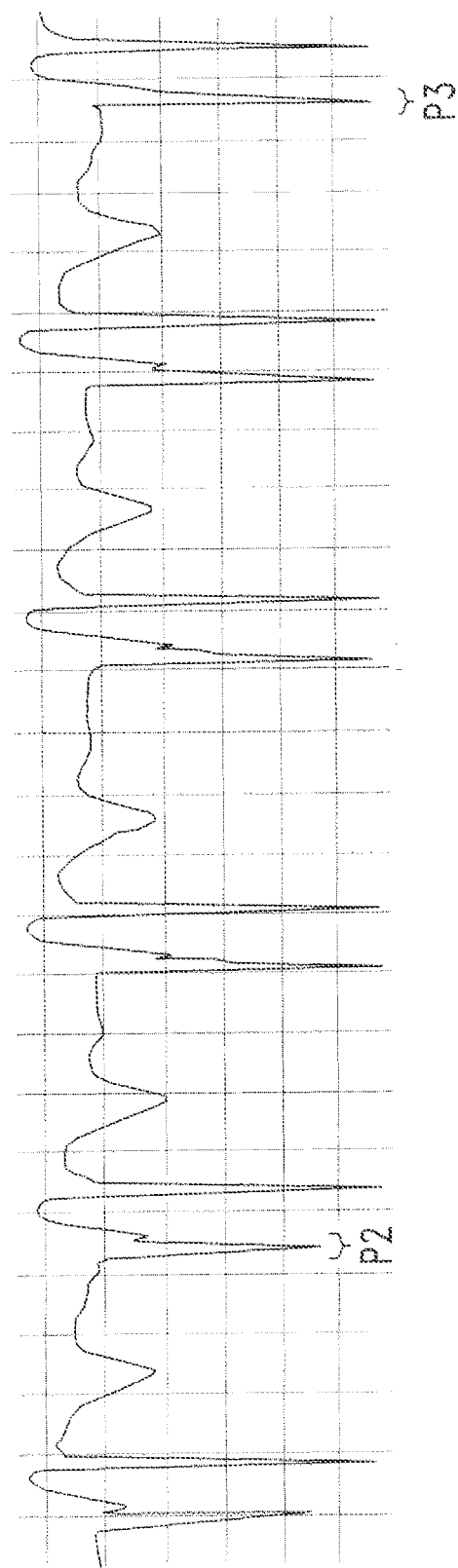
FIG. 1B is an exemplary ECG trace obtained from an electrode approaching the sino-atrial node and stopping adjacent thereto.
Figure 1C:
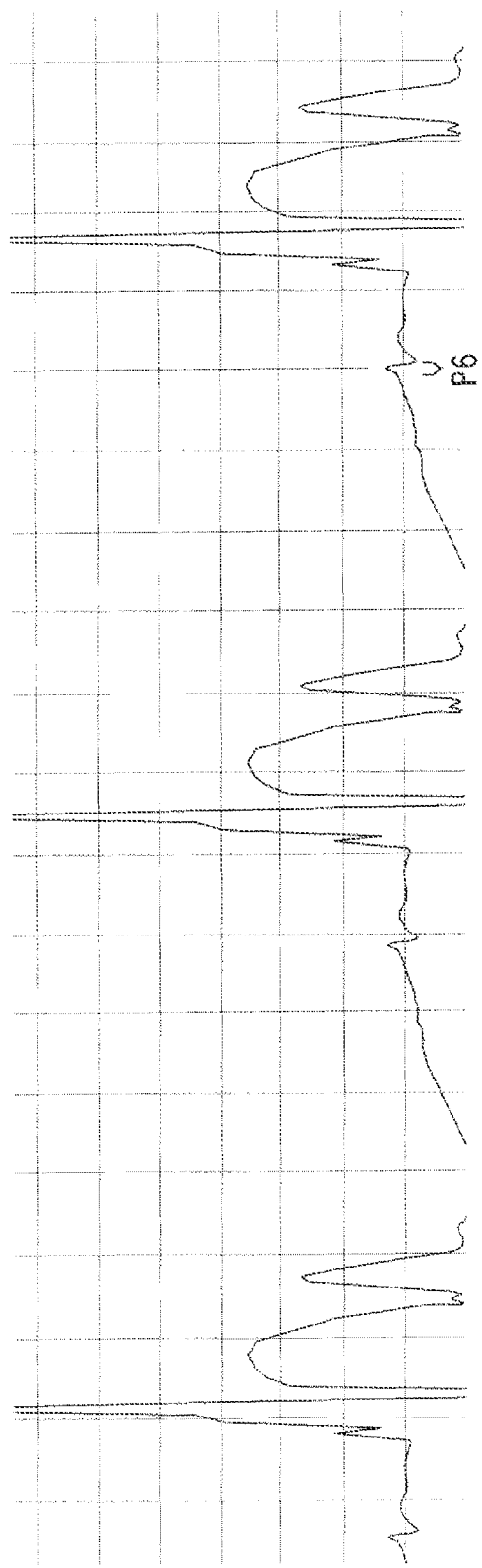
FIG. 1C is an exemplary ECG trace obtained from an electrode placed inside the right ventricle.
Figure 2B:
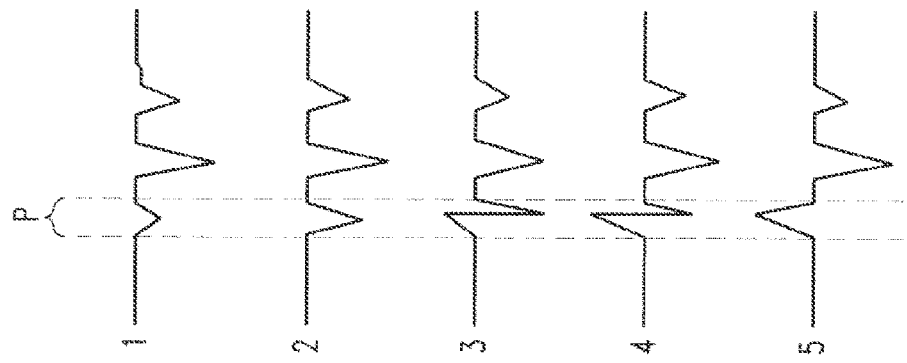
FIG. 2A is an illustration of a partial cross-section of the heart providing five exemplary tip locations 1, 2, 3, 4, and 5.
Figure 2A:
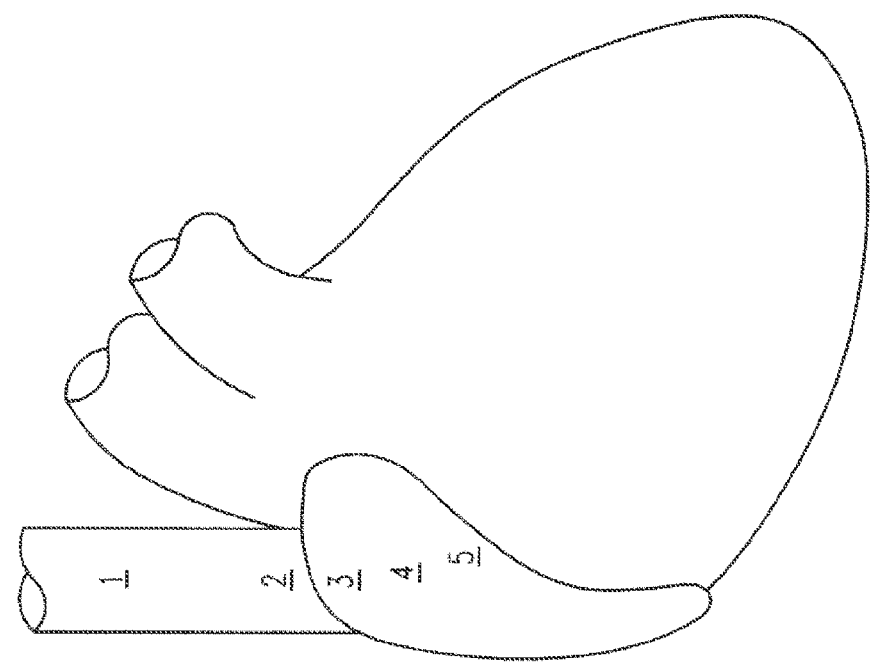

FIG. 2B is a series of exemplary P wave traces 1, 2, 3, 4, and 5 obtained from an electrode placed in each of the exemplary tip locations 1, 2, 3, 4, and 5 depicted in FIG. 2A, respectively.

Figure 3A:
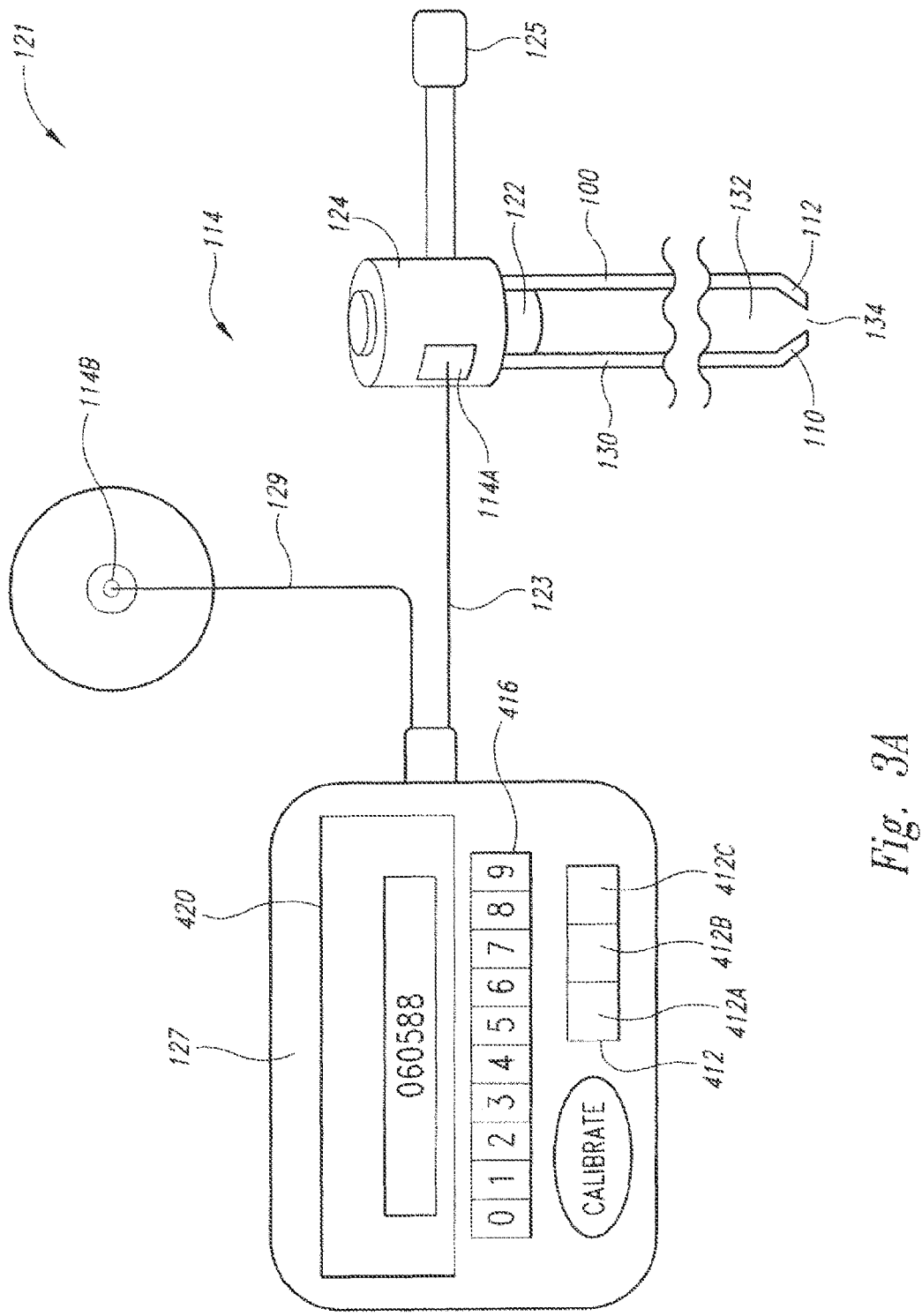

FIG. 3A is a signal analysis system configured to determine the position of the tip of a CVC using a single pair of electrodes.

Figure 3B:
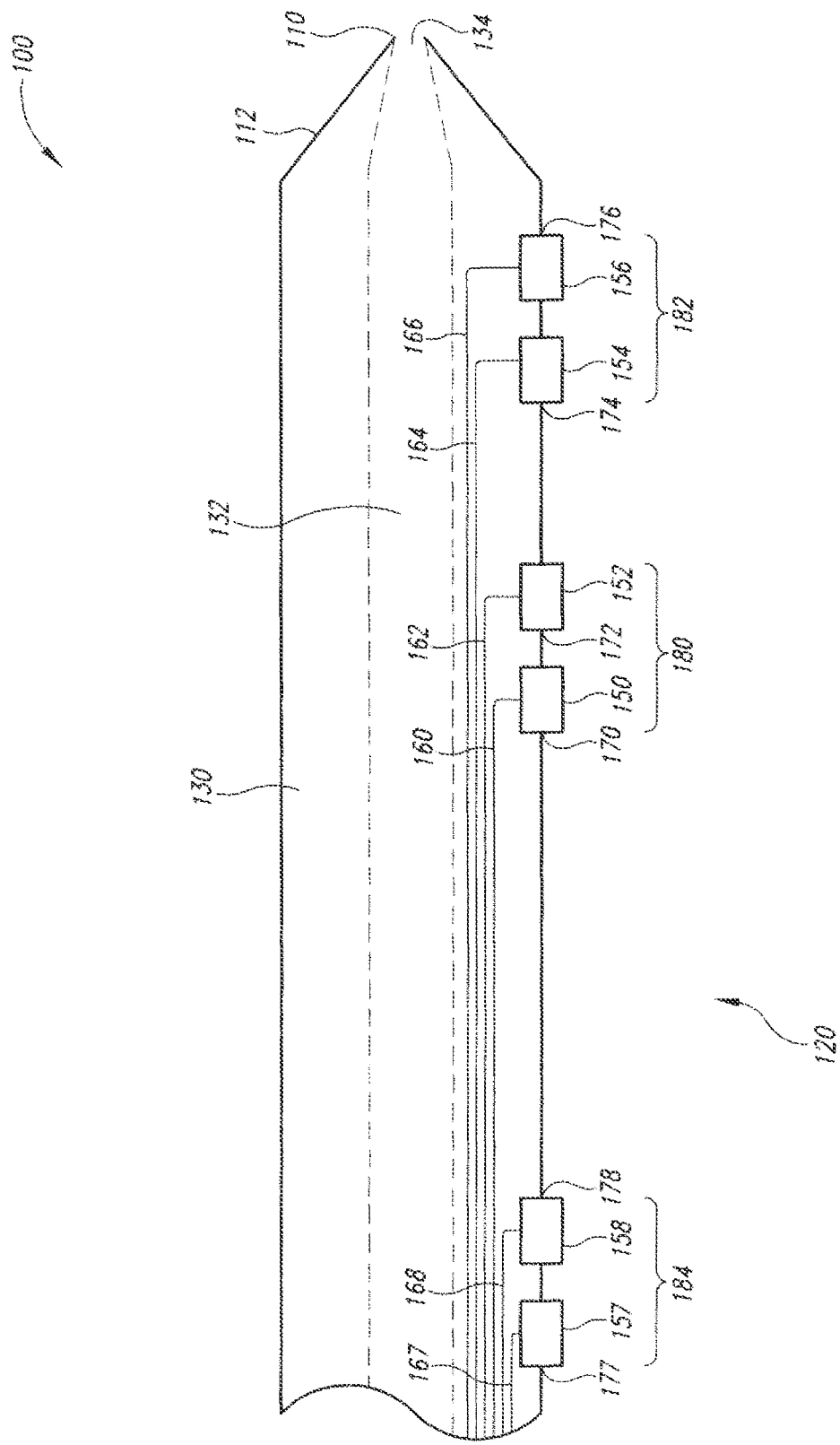

FIG. 3B is an embodiment of a CVC including three pairs of electrodes.

Figure 4:
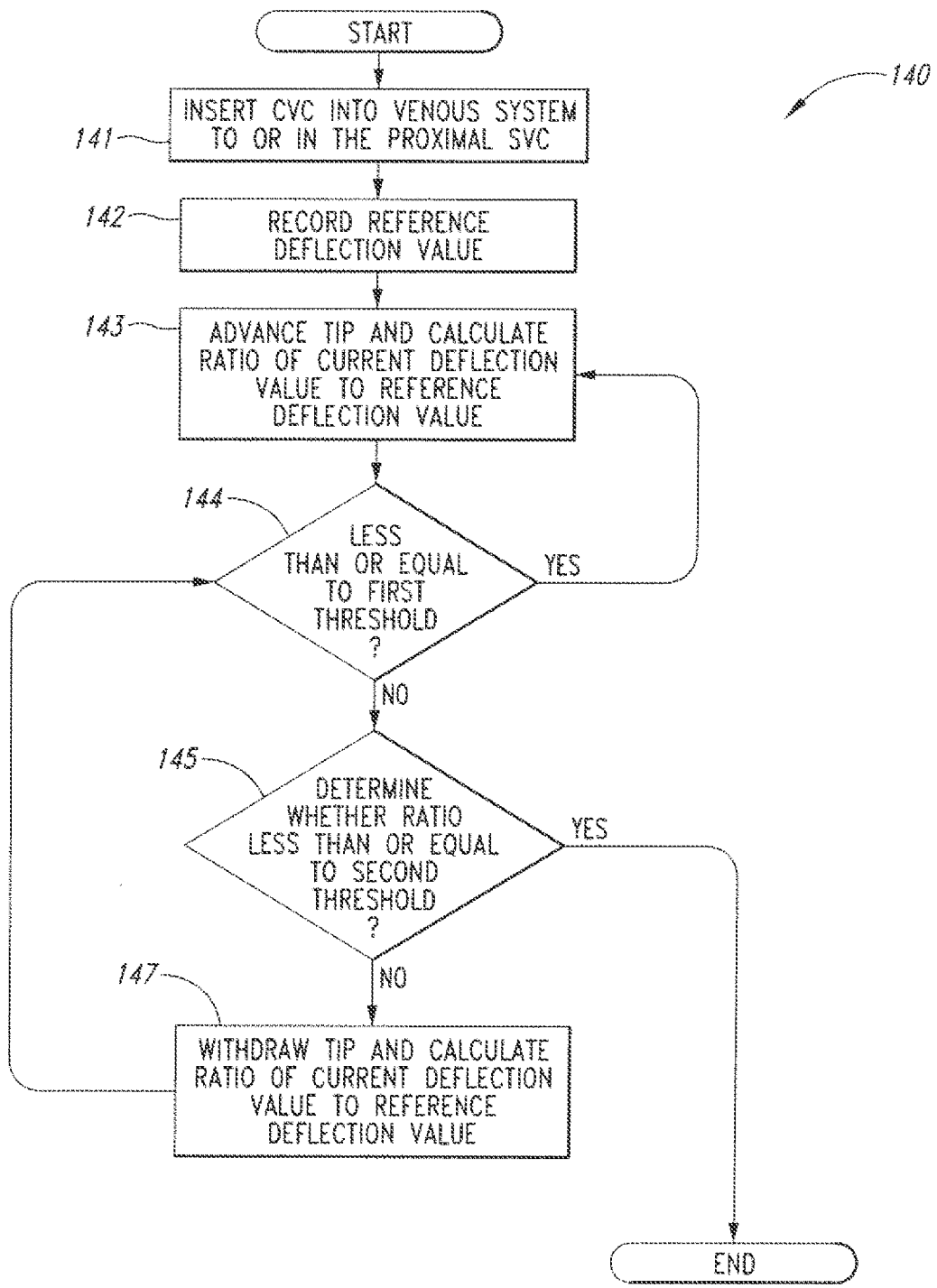

FIG. 4 is a block diagram illustrating a method of using a single pair of electrodes to locate the tip of the CVC within the SVC.

Figure 5:
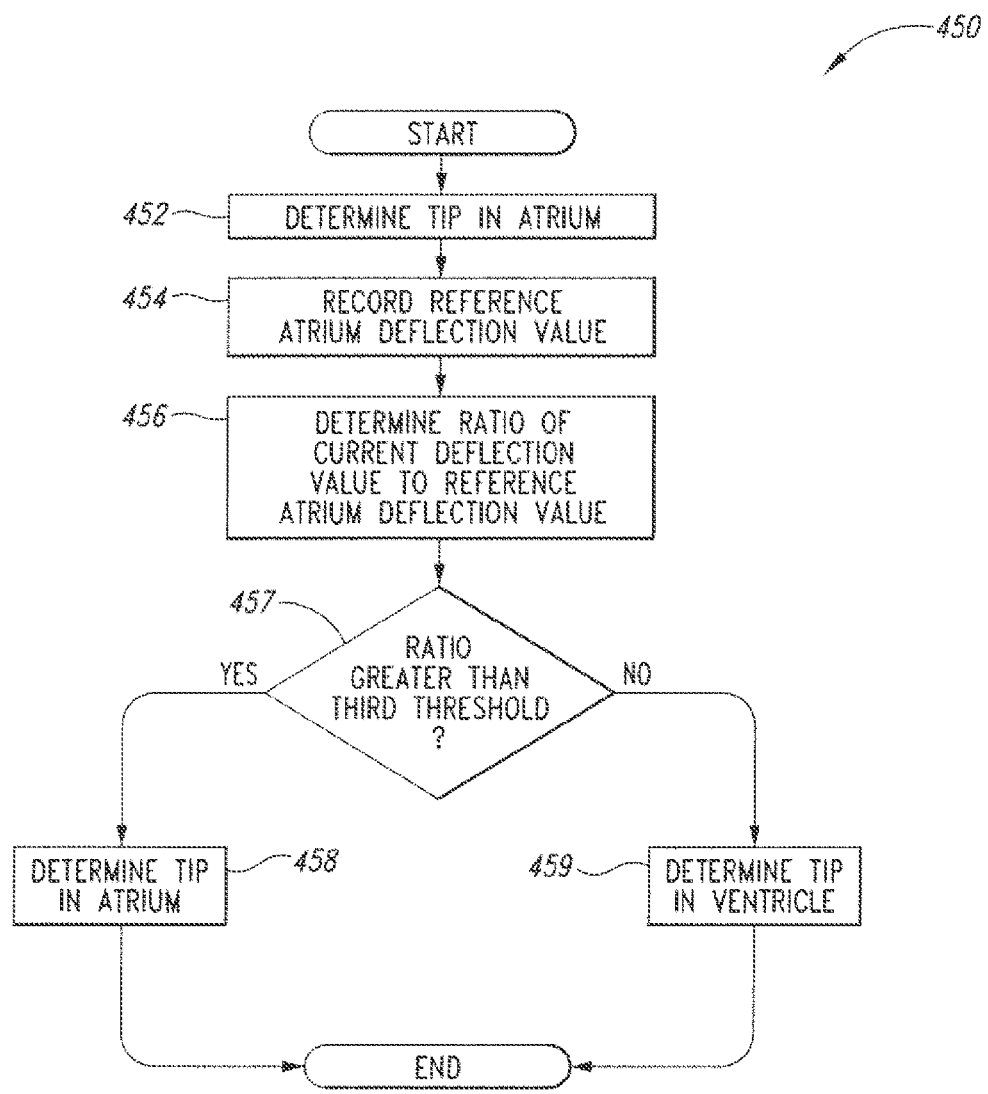

FIG. 5 is a block diagram illustrating a method of using a single pair of electrodes to determine the tip of the CVC is located within the right ventricle.

Figure 6:
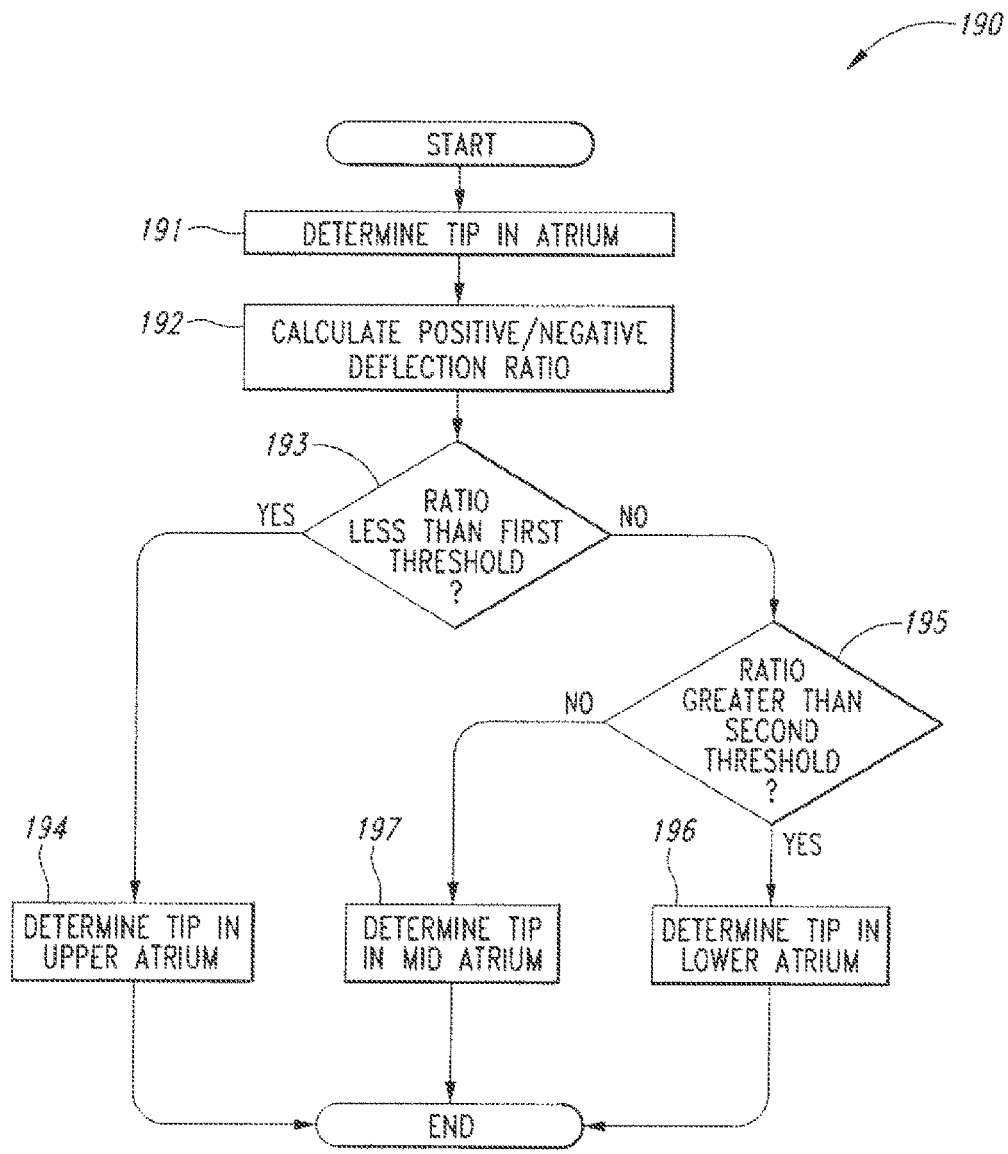

FIG. 6 is a block diagram illustrating a method of using a single pair of electrodes to determine the location of the tip of the CVC within the right atrium.

Figure 7:
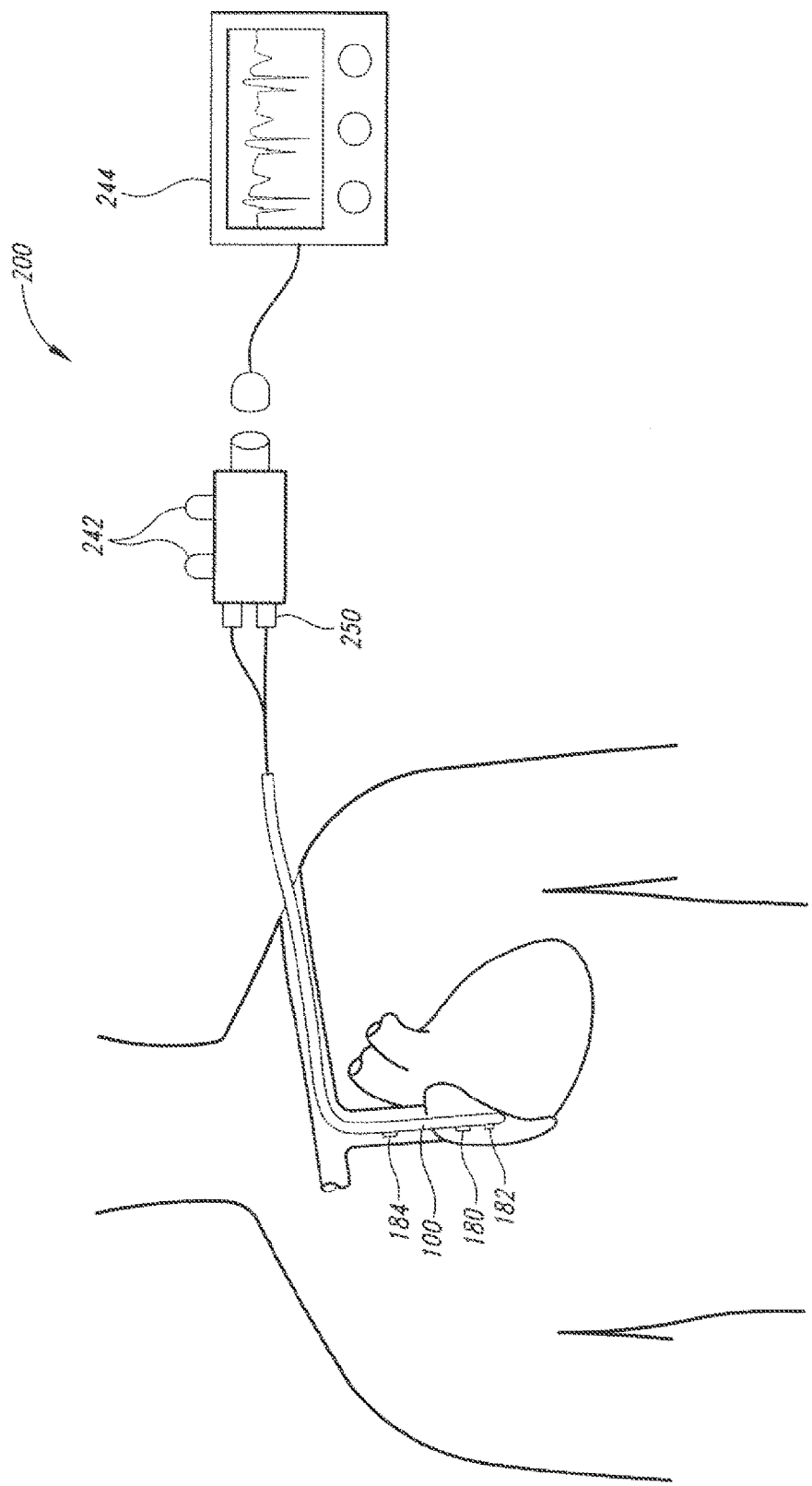

FIG. 7 is an embodiment of a signal analysis system for use with the CVC of FIG. 3B.

Figure 8:
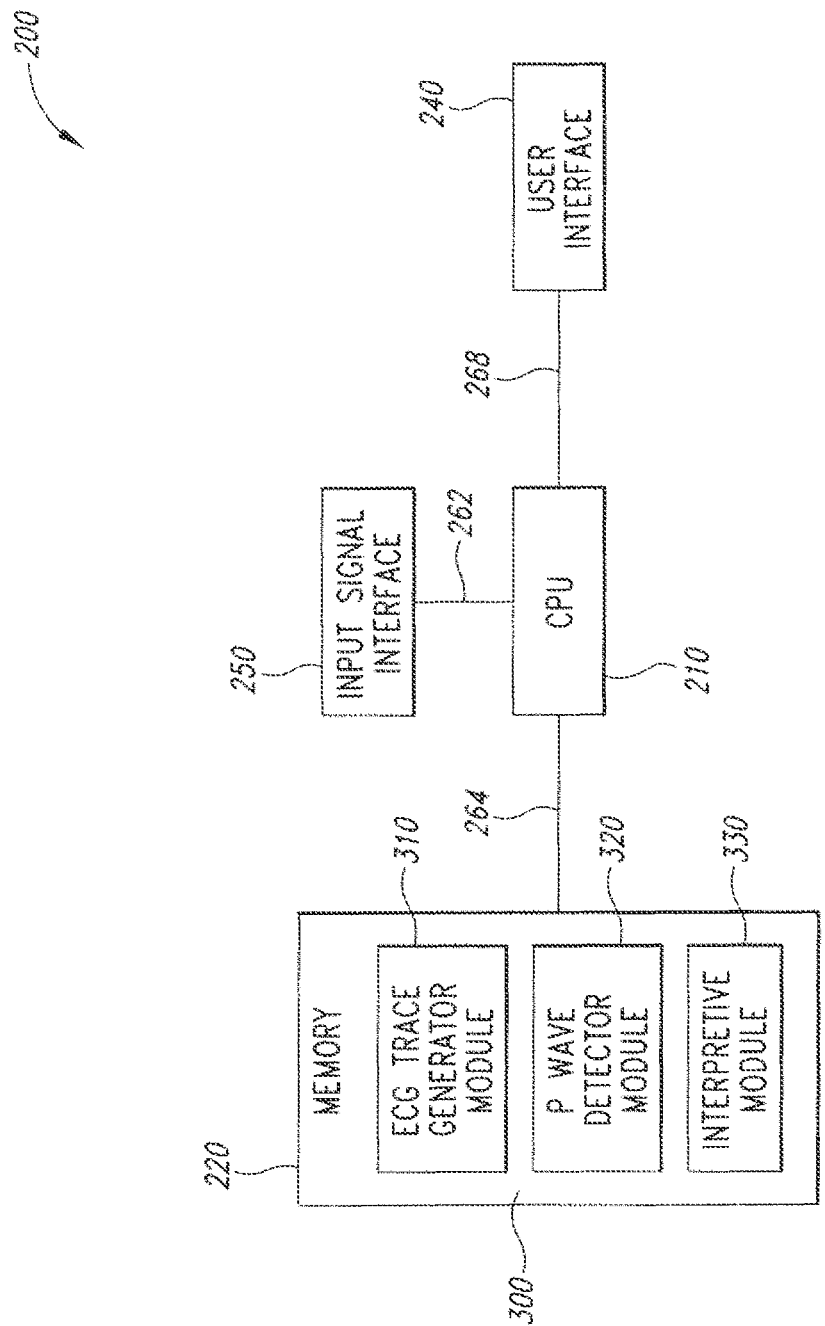

FIG. 8 is a block diagram illustrating the components of the signal analysis system of FIG. 7.

Figure 9:
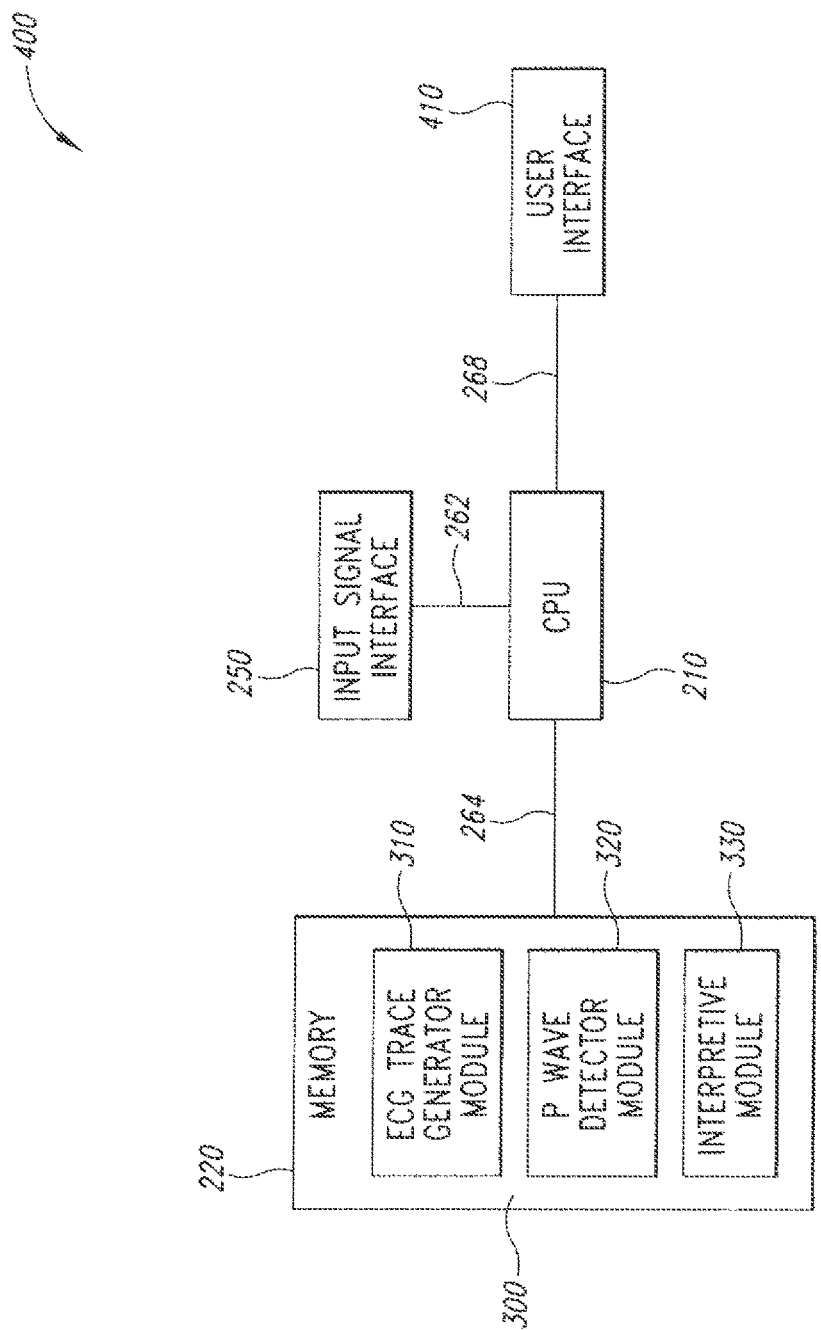

FIG. 9 is block diagram illustrating the components of a monitor of the signal analysis system of FIG. 3A.

Figure 10:
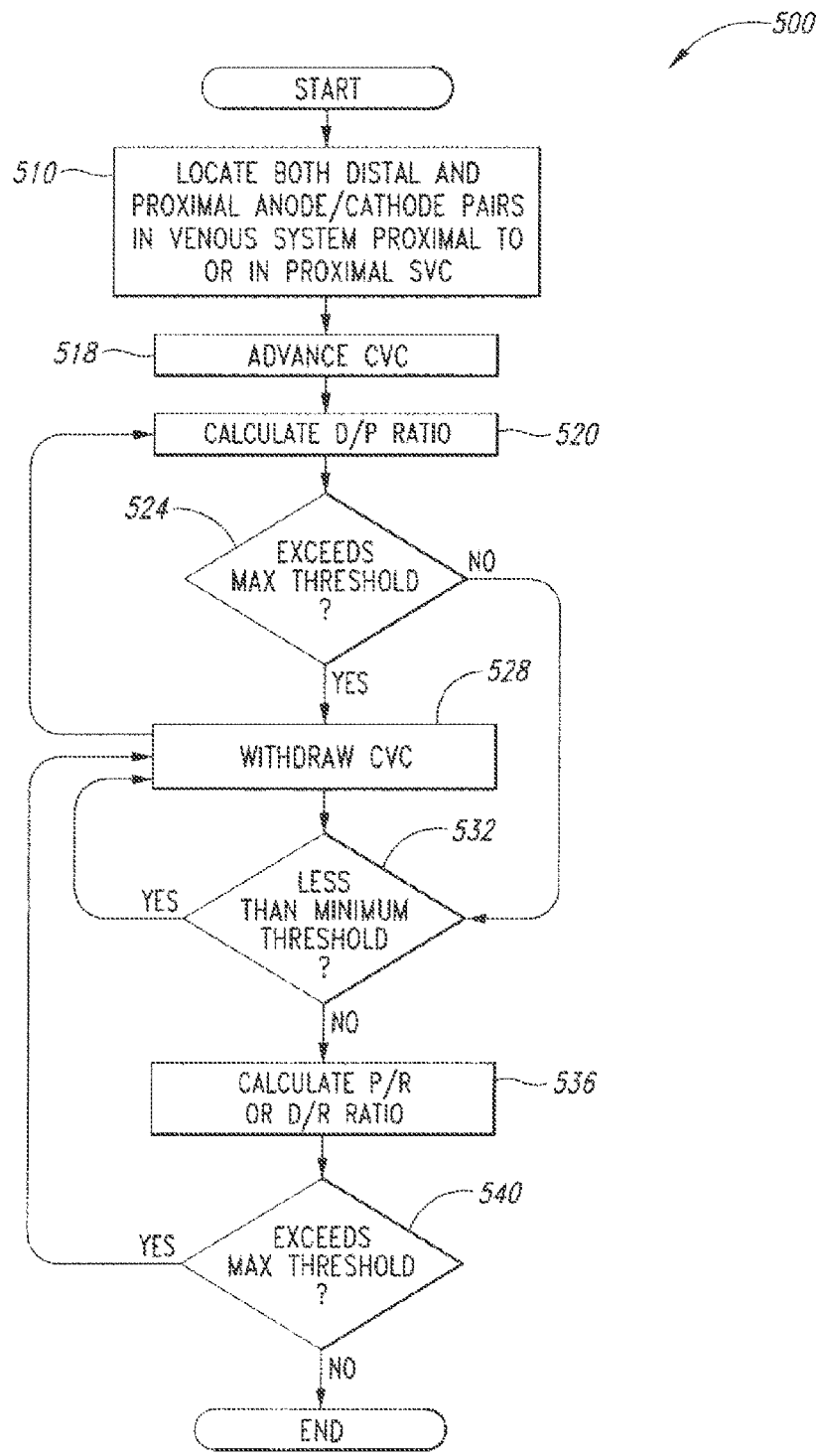

FIG. 10 is a block diagram illustrating a method of using at least two pairs of electrodes to locate the tip of the CVC relative to the SVC, right atrium, and right ventricle.

Figure 11A:
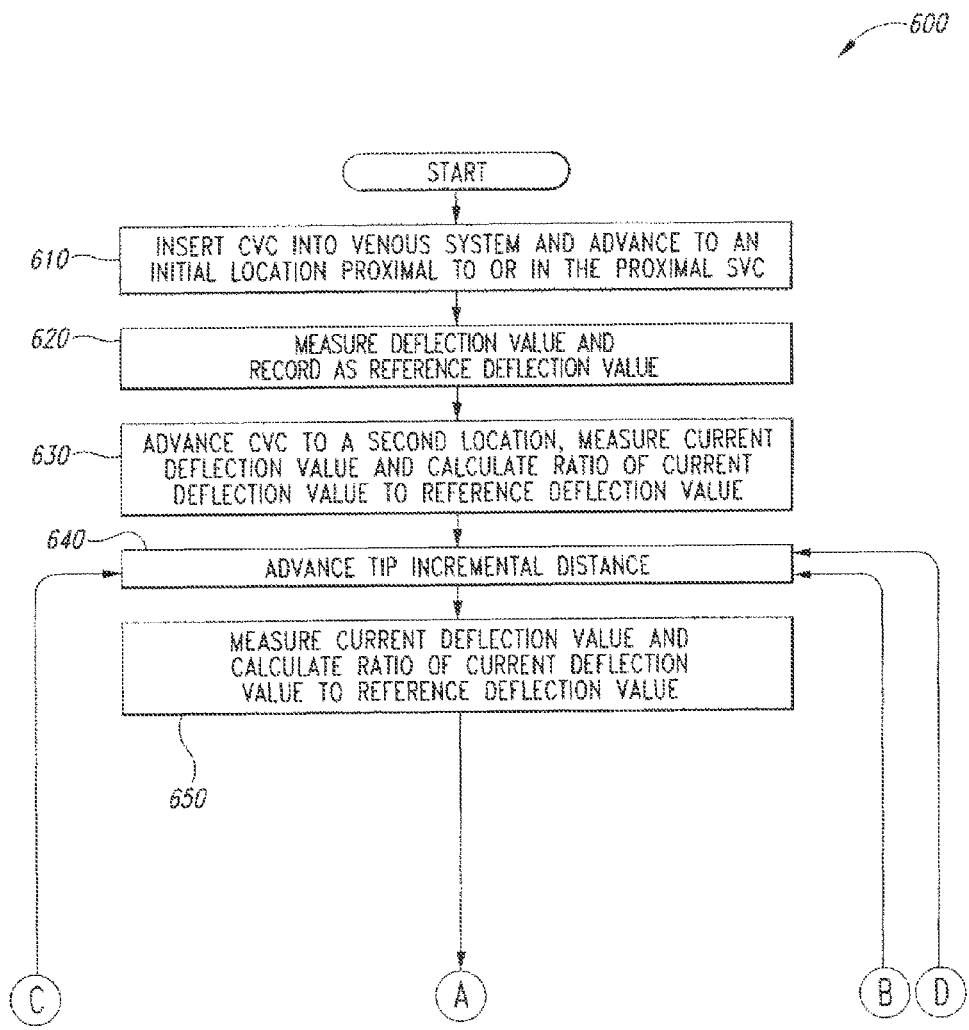
Figure 11B:
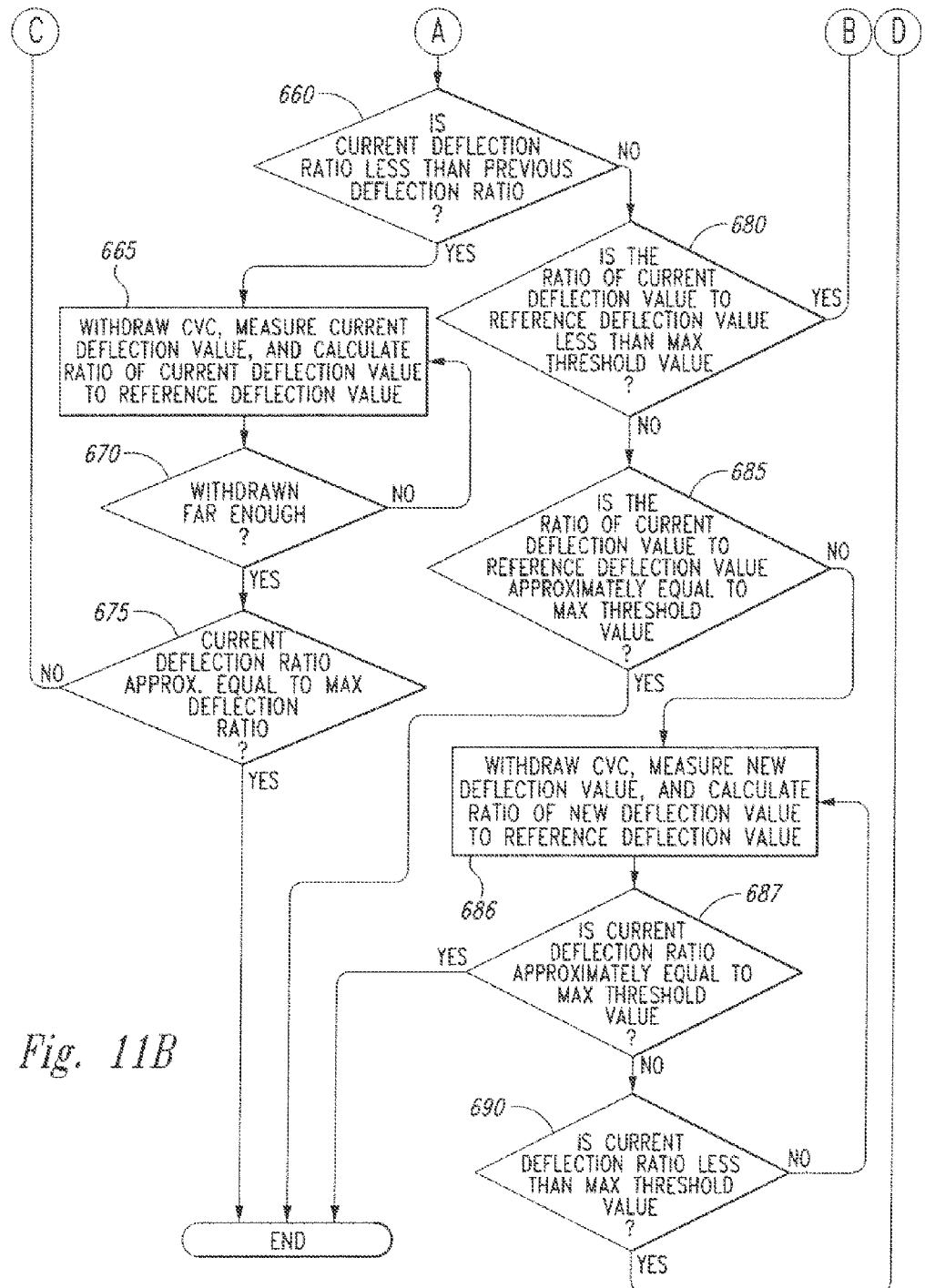

FIGS. 11A-11B are a block diagram illustrating an alternate method of using a single pair of electrodes to locate the tip of the CVC relative to the SA node.

DETAILED DESCRIPTION OF THE INVENTION

Central Venous Catheter 100

Aspects of the present invention are directed toward a device for locating the tip of a central venous catheter ("CVC") and a method of determining the location of the tip of a CVC. The embodiments depicted in FIGS. 3A and 3B, include a CVC 100 constructed using any manner known in the art from a flexible nonconductive material, such as polyurethane or other suitable polymer material. It may also be desirable to use a radiopaque material to construct the CVC 100. As is appreciated by those of ordinary skill in the art, the material used to construct the CVC 100 may include materials and/or coatings that provide improved anti-thrombotic or anti-bacterial properties. The CVC 100 has a body 130 configured to be received within a central vein. The body 130 may include a distal end 110 having a tapered tip 112 and a proximal end 120 spaced longitudinally along the body 130 from the distal end 110.

Referring to FIG. 3A, the body 130 may include one or more lumens 132 that traverse the length of the body and may have one or more openings 134 at or spaced from the tip 112 and an open end portion 122 configured to permit access into the lumen 132. When the tip 112 of the CVC 100 is received within a central vein, the open end portion 122 may remain outside the central vein allowing materials (e.g., saline, mediations, etc.) to be inserted into the lumen 132 while the tip 112 is inside the central vein or another anatomical structure. The opening 134 permits the passage of materials between the lumen 132 and the environment outside the CVC 100. If one or more materials are inserted into the lumen 132 via the open end portion 122, those materials may exit the lumen 132 via the opening 134. If materials enter the lumen 132 via the opening 134, those materials may exit the lumen 132 via the open end portion 122.

The open end portion 122 is configured be coupled to a connector 124 through which materials may be introduced into or exit from the open end portion 122 of the lumen 132. The connector 124 may include any suitable connector known in the art including a Tuohy-Borst adapter, stop cock, and the like. In the embodiment depicted in FIG. 3A, the connector 124 is a Tuohy-Borst adapter, which includes a side port 125 through which materials (e.g., saline) may be introduced into the open end portion 122 of the lumen 132. The side port 125 may be used to flush the lumen 132 with normal saline or another material. The connector 124 is configured to maintain materials within the lumen 132 and to prevent those materials from leaking out of the CVC 100 through the open end portion 122.

The lumens 132 may be used as conduits for the passage of materials such as medications and/or other fluids to and from the environment outside the CVC 100. For example, the lumen 132 may be used to aspirate blood into the CVC 100 and/or provide a conduit through which pressure data may be collected and used to construct pressure waveforms. The environment outside the CVC 100 may include the inside of the SVC, right atrium, and/or right ventricle. The CVC 100 is provided for illustrative purposes and those of ordinary skill in the art appreciate that alternate embodiments of CVC 100 including embodiments with additional lumens, a flow directed balloon tip, thermistors, thermodilution ports, pacing wire ports, embedded pacing electrodes, and the like are within the scope of the present invention.

Deflection Value

The deflection of an ECG trace, (i.e., its vertical height relative to the baseline) may be used to compare two or more P waves. Because a P wave constitutes a voltage change over time, the deflection of the P wave is not constant. In particular embodiments, the P wave is represented by an array or series of discrete numerical values.

The deflection value may be calculated in several ways. For example, the maximum or peak deflection may be used. Alternatively, the deflection value may be calculated as the difference between the maximum deflection and the minimum deflection. The deflection value may also be calculated as the sum of the absolute value of the maximum and minimum deflections. If the P wave has two peaks, which may occur when the tip 112 is located within the right atrium and the P wave is biphasic (see position 4 of FIGS. 2A and 2B), the deflection value may be calculated by totaling the absolute value of the two peaks. When this method is used, the deflection value of the P wave measured at positions 3-5 may all be approximately equal. Further, if discrete data is being used, the deflection value may also be calculated as a total of the discrete deflection quantities. If continuous data is being used, the deflection value may also be calculated as the integral under the P wave. Further, the deflection value may also be calculated as the average P wave deflection. Because the polarity of portions of the P wave change depending upon the location of the tip 112, it may be beneficial to use the absolute value of the deflection of the P wave to calculate the deflection value.

For the purposes of this application, the term "deflection value" will be used hereafter to describe the metric used to compare two or more P waves, which depending upon the implementation details may be detected by one or more pairs of electrodes. It is appreciated by those of ordinary skill in the art that the deflection value may be determined in numerous ways including those listed above and others not listed and the invention is not limited by the method and manner of determining the deflection value of the P wave.

In the embodiments discussed below, unless otherwise indicated, the deflection value is calculated as the sum of the absolute value of the maximum and minimum deflections when the maximum and minimum deflections have opposite polarities. The deflection value is calculated as the larger of the absolute value of the maximum and minimum deflections when the maximum and minimum deflections have the same polarity. In other words, the vertical height of the P wave is used.

Embodiments Using a Single Pair of Electrodes

Referring to FIG. 3A, an embodiment of a system 121 using a single pair of electrodes 114 to determine the position of the tip 112 of the CVC 100 will be described. An electrolytic material or solution, such as saline, may be disposed inside the lumen 132. The electrolytic material inside the lumen 132 forms a continuous conductor or column of electrolytic material that may be used to conduct an electrical signal from the opening 134 in the tip 112, and up the continuous column. In other words, the opening 134 exposes the electrolytic material inside the lumen 132 to electrical activity occurring in the environment outside the tip 112. A first electrode 114A of the pair of electrodes 114 is placed in electrical communication with the continuous column inside the lumen 132. The first electrode 114A may be coupled by a wire 123 to a monitor 127.

A second or surface electrode 114B is placed in contact with the skin of a patient. By way of a non-limiting example, the surface electrode 114B may be affixed to the skin of the patient's chest using any method known in the art. The surface electrode 114B is coupled to the monitor 127 by a wire 129. The voltage at or near the opening 134 in the tip 112 may be measured using the pair of electrodes 114.

The voltages detected by the pair of electrodes 114 may be used to create an ECG trace of the electrical activity observed at or near the tip 112 of the CVC 100. Because the voltage across each of the pair of electrodes 114 may vary with time, the voltage across wires 123 and 129 may constitute a time-varying signal that can be analyzed using standard signal processing methods well known in the art. In a typical patient, the maximum voltage across the pair of electrodes 114 may range from about 0.2 mV to about 3 mV. The signal detected by the pair of electrodes 114 may be amplified and/or filtered to improve the signal quality.

In the embodiment depicted in FIG. 3A, the first electrode 114A is coupled to the connector 124. Alternatively, the first electrode 114A may be located inside at least a portion of the lumen 132. By way of another example, the first electrode 114A is coupled to the side port 125 through which the electrolytic material (e.g., saline) may be introduced into the open end portion 122 of the lumen 132. As is apparent to those of ordinary skill in the art, the first electrode 114A may be located anywhere that would place it in electrical continuity or communication with the electrolytic material (e.g., saline) exiting the tip 112 via the opening 134 or otherwise communicating electrically with the environment outside the opening 134 of the tip 112. By way of another example, the first electrode 114A may be incorporated into a guide wire (not shown), stylet, and the like that extends from, or near the tip 112 up the body 130 of the CVC 100 and is electrically coupled by the wire 123 to the monitor 127. The monitor 127 is described in detail below.

Method of Using a Single Electrode Pair to Determine the Position of the TIP of the CVC Referring to FIG. 4, a method 140 of determining the location of the tip 112 using the pair of electrodes 114 will now be described. In block 141, the CVC 100 is inserted into the SVC. The CVC 100 may gain venous access to the SVC by any method known in the art including inserting the CVC 100 in a standard sterile fashion through the subclavian, one of the jugular veins, or a peripheral vein and directing the tip 112 of the CVC 100 through that vein toward the proximal SVC.

Next, in block 142, a reference deflection value is recorded in a storage location. The reference deflection value is the deflection value obtained from the pair of electrodes 114 when the tip 112 is located in the venous system proximal to or in the proximal SVC.

Then, in block 143, the tip 112 is advanced. As the tip 112 is advanced, a ratio of the deflection value of the currently observed P wave to the reference deflection value is calculated. Inside the SVC, as the tip 112 approaches the mid SVC, the deflection value of the P wave may increase by two to four times the reference deflection value. Further, as the tip 112 approaches the distal SVC, the deflection value of the P wave may increase by four to six times the reference deflection value. In the distal SVC near the SA node, the deflection value of the P wave may increase by six to eight times the reference deflection value.

In decision block 144, whether the ratio is less than or equal to a first predefined threshold value is determined. The first predefined threshold value should be large enough to ensure the tip 112 has left the proximal SVC and entered the mid SVC. Further, the first predefined threshold value should be small enough to prevent placement of the tip 112 in the distal SVC. Thus, the first predefined threshold value may be within a range of about 1.6 to about 3.9. By way of a non-limiting example, the first predefined threshold value may be about 2.0. If the ratio is less than or equal to the first predefined threshold value, in block 143, the tip 112 may be advanced and the ratio recalculated. Ratio values less than or equal to the first predefined threshold value indicate the tip 112 is in the proximal or mid SVC and has not yet reached either the distal SVC, caval-atrial junction adjacent to the SA node or the upper right atrium.

If decision block 144 determines the ratio is not less than or equal to the first predefined threshold value, the method 140 advances to decision block 145. In decision block 145, whether the ratio is less than or equal to a second predefined threshold value is determined. The second predefined threshold value should be large enough to ensure the tip 112 is in the distal SVC and small enough to avoid entry of the tip 112 into the right atrium. By way of a non-limiting example, the second predefined threshold value may within a range of about 4.0 to about 8.0. By way of a non-limiting example, the second predefined threshold value may be about 8.0. In other words, the block 144 determines whether the ratio is between the first and second threshold values or within a range defined between the first and second threshold values (e.g., about 2.0 to about 8.0). Nevertheless, ratio values within the range defined between the first and second threshold values may indicate the tip 112 is approaching or has reached the SA node, or the tip is located within the right atrium. In other words, any ratio value above the second predefined threshold value may indicate the tip 112 is located in the distal SVC or the upper atrium. If the ratio is within the range defined between the first and second threshold values, the decision in decision block 145 is "YES" and the method 140 ends.

If the ratio is greater than the second threshold value, the decision in decision block 145 is "NO," and the method 140 advances to block 147. When the ratio is greater than the second threshold value, the tip 112 is in or near the right atrium and in block 147, the user or operator is advised to withdraw the tip 112. By way of a non-limiting example, the user or operator may be advised to withdraw the tip 112 about 0.5 cm to about 1 cm. Then, in block 147, advancement of the tip 112 is terminated and the tip 112 withdrawn. By way of a non-limiting example, the user or operator may withdraw the tip 112 about 0.5 cm to about 1 cm. In block 147, as the tip 112 is withdrawn, the ratio of the deflection value of the currently observed P wave to the reference deflection value is recalculated.

Then, the method 140 returns to decision block 144.

In particular embodiments, if at any time during the performance of method 140, the ratio is equal to the second predefined threshold value, the tip 112 is maintained in its current position without additional advancement or withdrawal and the method 140 ends. When the method 140 ends, the ratio is between the first and second threshold values and the tip 112 is located in the mid SVC or distal SVC.

The following table, Table 1, summarizes the relationship between the location of the tip 112 of the CVC 100 and the ratio of the deflection value of the currently observed P wave to the reference deflection value:

TABLE 1

| Location of the tip 112 | Proximal SVC | Mid SVC | Distal SVC | Very Distal SVC or Right Atrium |
|---|---|---|---|---|
| Ratio: ratio of the deflection value of the currently observed P wave to the reference deflection value | ≤1.5 | 1.6-4.0 | 4.1-5.5 | >5.5-8.0 |

While Table 1 provides exemplary ranges and/or threshold values for use as a general guideline, those of ordinary skill in the art appreciate that these values may benefit from adjustment as additional anatomic or electrophysiologic data is acquired and such modified values are within the scope of the present invention.

As is apparent to those of ordinary skill, the pair of electrodes 114 may be used to detect the instantaneous location of the tip 112. Therefore, if the tip 112 migrates into the atrium, this movement may be detected immediately by calculating a ratio of the deflection value of the currently observed P wave to the recorded reference deflection value and comparing the ratio to the first and second threshold values. This calculation may be performed periodically or at random intervals. If the tip 112 migrates into the atrium, a medical professional may be alerted via a signal, such as an alarm, and the like, to reposition the tip 112.

Referring to FIG. 5, a method 450 may be used to determine the tip 112 is located within the ventricle. In first block 452, the tip 112 is located in the atrium. Then, in block 454, a reference atrium deflection value is recorded. The reference atrium deflection value is the deflection value obtained from the pair of electrodes 114 when the tip 112 is located in the atrium. Then, in block 456, a ratio of the deflection value of the current P wave detected by the pair of electrodes 114 to the reference atrium deflection value is determined. In decision block 457, whether the ratio is greater than a third predefined threshold value is determined. The third predefined threshold value may be about 0.5. If the decision is "YES," the ratio is greater than the third predefined threshold value, and in block 458, the tip 112 is determined to be in the right atrium. Then, the method 450 ends. If the decision in decision block 457 is "NO," the ratio is less than or equal to the third predefined threshold value, and in block 459, the tip 112 is determined to be in the right ventricle. Then, the method 450 ends.

Within at least a portion of the range defined between the first and second threshold values (e.g., about 2.0 to about 8.0), the P wave voltage measured using prior art techniques, such as those disclosed by U.S. Pat. Nos. 5,078,678 and 5,121,750 (both issued to Katims), has generally not yet reached its maximum value. Therefore, the present method indicates the tip 112 should be withdrawn before those techniques would signal withdrawal. For example, typically the P wave voltage within the proximal SVC is about 0.2 to about 0.3 mV. Near the SA node, the P wave voltage may increase about 8 fold (e.g., about 1.6 mV to about 2.4 mV. In other words, the ratio is about 8 near the SA node, which is the location of the maximum P wave voltage used in the prior art. However, prior art techniques advise to advance the tip until it can be clearly seen that the maximum P voltage has been reached. Therefore, the prior art techniques allow the tip 112 to advance further into the right atrium than the present technique before identifying the advancement should be halted and the tip withdrawn back into the SVC. Because the present technique halts the advancement of the tip 112 earlier (e.g., when the P wave voltage increases above the second predefined threshold value of about 8.0, which corresponds to about 1.6 mV to about 2.4 mV) than prior art techniques, the present teachings may avoid many of the risks associated with advancing the tip into the right atrium.

Further, the prior art teaches using a threshold percentage decrease to determine the tip 112 is in the correct location. However, using a threshold percentage decrease may be ineffective at locating the tip 112 within the SVC because the percentage decrease may vary from patient to patient. In other words, depending upon the anatomical structures of the patient, the tip 112 may have to be withdrawn until the percentage decreases differing amounts. On the other hand, if the tip 112 is withdrawn until the ratio is between about 2.0 and about 8.0 (e.g., the current P wave voltage is about 0.4 mV to about 2.4 mV), the tip will be located in the mid SVC or in some cases, the distal SVC. Therefore, the present technique more accurately positions the tip 112 than prior art techniques.

In addition to halting the advancement of the tip 112 when the ratio of the deflection value of the currently observed P wave to the reference deflection value has exceeded either of the first and second predefined threshold values, advancement of the tip 112 could also be halted when the deflection value of the currently observed P wave is approximately equivalent to the voltage (or deflection value) of the QRS complex.

As discussed above, when observed using a standard bipolar Lead II trace, the P wave voltage is almost entirely negative at the top of the right atrium (see trace 3 of FIG. 2B), biphasic in the mid right atrium (see trace 4 of FIG. 2B), and positive at the bottom of the right atrium (see trace 5 of FIG. 2B). A positive/total deflection ratio may be calculated and used to determine when advancement of the tip 112 should be halted. The positive/total deflection ratio is a ratio of the greatest positive deflection value (of an initial positive or upwardly deflecting portion that precedes a downwardly deflecting portion) to the total deflection value of the currently observed P wave. When the positive/total deflection ratio is greater than a predetermined fraction (e.g., one quarter, one eighth, etc.) advancement of the tip 112 should be halted. For example, the traces 3-5 illustrated in FIG. 2B each have an initial upwardly deflecting portion. However, in both cases, the greatest positive deflection value of the initial upwardly deflecting portion of the P wave is clearly greater than one quarter of the total deflection value of the currently observed P wave. As explained above, in these traces, the tip 112 is located in the right atrium. Thus, if the greatest positive deflection value is greater than the predetermined fraction of the total deflection value of the currently observed P wave, the tip 112 is in the right atrium and should be withdrawn.

Alternate Method of Using a Single Electrode Pair to Determine the Position of the TIP of the CVC FIGS. 11A and 11B provide a block diagram of an alternate method 600 of advancing and locating the tip 112 of the CVC 100. A physical cathode-anode electrode pair is used in a standard bipolar lead setup. A bipolar lead setup means two physical leads are used (rather than one virtual lead and one physical lead, which are referred to as a unipolar lead setup).

For illustrative purposes, the method 600 is described using the first electrode 114A (see FIG. 3A) functions as a cathode at the tip 112 and the second electrode 114B (see FIG. 3A) functions as an anode attached to the patient's skin near his/her right shoulder. The continuous conductor or column inside the lumen 132, which is in electrical communication with both the first electrode 114A and the electrical activity occurring in the environment outside the tip 112 functions as a "wandering electrode," which is the positive cathode. The second electrode 114B serves as the negative anode electrode. While technically this configuration is not a standard Lead II configuration, the trace produced by the electrodes 114A and 114B may be displayed on a standard ECG monitor using the monitor's circuitry to display the trace as a bipolar Lead II trace. Thus, an ECG trace is generated for the wandering electrode relative to the electrode "RA," which is displayed as a Lead II trace. However, as is apparent to those of ordinary skill in the art, through application of ordinary skill in the art to the present teachings other ECG Lead traces could be used and are within the scope of the present disclosure.

As is apparent to those of ordinary skill in the art, in a standard unipolar lead setup, three surface electrodes (not shown) are attached to a patient's skin: an electrode "RA" is attached to the patient's right arm (or shoulder), an electrode "LA" is attached to the patient's left arm (or shoulder), and an electrode "LL" is attached to the patient's left leg. A virtual electrode may be created using ECG software, which calculates the virtual electrode as the electrical center of an Einthoven's triangle created by the electrodes "RA," "LA," and "LL" used in the Lead I, Lead II, and Lead III configurations. The continuous conductor or column inside the lumen 132, which is in electrical communication with both the first electrode 114A and the electrical activity occurring in the environment outside the tip 112 functions as a "wandering electrode." The wandering electrode is the positive cathode, and the virtual electrode is the negative anode electrode. Thus, an ECG trace is derived for the wandering electrode relative to the virtual electrode. In addition to Leads I, II, and III (of the bipolar configurations), some ECG monitors display unipolar lead configurations, e.g., aVR, aVL, aVF derived from a composite of the electrodes "RA," "LA" and "LL," or a chest electrode, variably called a "V," "MCL," or "Chest" lead (hereafter referred to as the "V" lead). Some ECG monitors display this ECG trace as a unipolar "V" lead trace and some users particularly like to use the unipolar "V" lead trace to guide the tip 112 of the CVC 100. However, most users use the bipolar Lead II trace generated for the wandering electrode relative to the electrode "RA" (i.e., the ECG Lead II configuration discussed above). As is apparent to those of ordinary skill in the art, with respect to the method 600, any number of bipolar or unipolar lead configurations may be used with acceptable results. Further, either the unipolar "V" lead trace or the bipolar Lead II trace (among others) may be used to perform the method 140.

In method 600, the deflection values measured include only the negative polarity or downwardly extending portion of the P-wave. The upwardly extending positive polarity portion is not included in the measurement of the deflection values. Thus, the deflection value is calculated as the absolute value of the minimum deflection.

In first block 610, the CVC 100 is introduced into the venous system and advanced to an initial location estimated to place the tip 112 of the CVC 100 at or proximal to the proximal SVC. In next block 620, a deflection value of the P wave observed at the initial location is measured and stored as a reference deflection value.

Then, in block 630, the CVC 100 is advanced from the initial location to a second location. By way of a non-limiting example, the CVC 100 may be advanced from the initial location about 0.5 cm to about 1.0 cm in block 630. At the second location, a new deflection value is measured using of the P wave observed at the second location. A deflection ratio of the new deflection value to the reference deflection value is then calculated. As the method 600 is performed, a maximum deflection ratio observed is stored. Thus, in block 630, the maximum deflection value observed is equal to the deflection ratio observed at the second location.

In block 640, the CVC 100 is advanced from the second location by an incremental distance. By way of a non-limiting example, the incremental distance may be within a range of about 0.5 cm to about 1.0 cm. However, a smaller sized incremental distance may be used and is within the scope of the present teachings.

After the CVC 100 has been advanced by the incremental distance, in block 650, a current deflection value of the P wave observed at the new location is measured and a current deflection ratio of the current deflection value to the reference deflection value is calculated. If the current deflection ratio is greater than the maximum deflection ratio, the maximum deflection ratio is set equal to the current deflection ratio. Before the CVC 100 was advanced, the CVC was located a previous location. The deflection value measured at the previous location is a previous deflection value and the deflection ratio of the previous deflection value to the reference deflection value is a previous deflection ratio.

Then, in decision block 660, the current deflection ratio is compared to the previous deflection ratio. The decision in decision block 660 is "YES" when the current deflection ratio is less than the previous deflection ratio. Otherwise, the decision in decision block 660 is "NO."

When the decision in decision block 660 is "YES," in block 665, the CVC 100 is withdrawn from the current location to a new location. By way of a non-limiting example, in block 665, the CVC 100 may be withdrawn about 0.5 cm to about 1.0 cm. Then, a new deflection value of the P wave observed at the new location is measured and a new deflection ratio of the new deflection value to the reference deflection value is calculated. If the new deflection ratio is greater than the maximum deflection ratio, the maximum deflection ratio is set equal to the new deflection ratio. At this point, the location of the CVC 100 before withdrawal is a previous location and the deflection ratio calculated at the previous location is a previous deflection ratio. The location of the CVC 100 after withdrawal is a current location and the deflection ratio calculated at the current location is a current deflection ratio. By way of a non-limiting example, the CVC 100 may be withdrawn about 1 cm. Then, the method 600 advances to decision block 670.

In decision block 670 whether the CVC 100 has been withdrawn far enough is determined. In decision block 670, a positive/total deflection ratio of the greatest positive deflection value (of an initial positive or upwardly deflecting portion which precedes a downwardly deflecting portion) to the total deflection value of the currently observed P wave is calculated. The decision in decision block 670 is "YES" when the positive/total deflection ratio is less than a predetermined fraction (e.g., one quarter, one eighth, etc.). Otherwise, the decision in decision block 670 is "NO."

Alternatively, in decision block 670, a negative/total deflection ratio of the smallest negative deflection value (of a negative polarity or downwardly deflecting portion of the currently observed P wave which follows an upwardly deflecting positive polarity portion of the currently observed P wave) to the total deflection value of the currently observed P wave is calculated. The decision in decision block 670 is "YES" when the negative/total deflection ratio is greater than or equal to a predetermined fraction (e.g., three quarters, seven eighths, etc.). Otherwise, the decision in decision block 670 is "NO."

When the decision in decision block 670 is "YES," the method 600 advances to decision block 675. When the decision in decision block 670 is "NO," the method 600 returns to block 665.

In decision block 675, the current deflection ratio is compared to the maximum deflection ratio observed. The decision in decision block 675 is "YES" when the current deflection ratio is approximately equal to the maximum deflection ratio observed. By way of a non-limiting example, the current deflection ratio may be considered approximately equal to the maximum deflection ratio observed when the absolute value of the difference between the current deflection ratio and the maximum deflection ratio observed is less than 0.2. If the current deflection ratio is not approximately equal to the maximum deflection ratio observed, the decision in decision block 675 is "NO."

When the decision in decision block 675 is "YES," the method 600 ends. When the decision in decision block 675 is "NO," the method 600 returns to block 640.

When the decision in decision block 660 is "NO," the current deflection ratio (calculated after the CVC 100 was advanced by the current incremental distance) is greater than or equal to the previous deflection ratio (calculated after the CVC 100 was advanced by the previous incremental distance). When the decision in decision block 660 is "NO," the method 600 advances to decision block 680.

The decision in decision block 680 is "YES," when the current deflection ratio is less than a maximum threshold value. Otherwise, decision in decision block 680 is "NO." By way of a non-limiting example, the maximum threshold value may be about 8.0.

When the decision in decision block 680 is "YES," the current deflection ratio is less than the maximum threshold value (e.g., 8.0) and greater than the previous deflection ratio. When this is the case, the method 600 returns to block 640.

When the decision in decision block 680 is "NO," the current deflection ratio is greater than or equal to the maximum threshold value (e.g., 8.0), and the method 600 advances to decision block 685 to determine whether the current deflection ratio is approximately equal to the maximum threshold value.

When the current deflection ratio is approximately equal to the maximum threshold value, the decision in decision block 685 is "YES." Otherwise, decision in decision block 685 is "NO." The current deflection ratio may be considered approximately equal to the maximum threshold value when the absolute value of the difference between the current deflection ratio and the maximum threshold value is less than 0.2.

When the decision in decision block 685 is "YES," the method 600 ends. When the decision in decision block 685 is "NO," the current deflection value is neither less than nor equal to the maximum threshold value. When this occurs, the method 600 progresses to block 686 whereat the CVC 100 is withdrawn from the current location to a new location. Then, a new deflection value of the P wave observed at the new location is measured and a new deflection ratio of the new deflection value to the reference deflection value is calculated. The location of the CVC 100 after withdrawal is a current location and the deflection ratio calculated at the current location is a current deflection ratio. By way of a non-limiting example, the CVC 100 may be withdrawn about 1 cm. Then, the method 600 advances to decision block 687.

In decision block 687, the current deflection ratio is compared to the maximum threshold value. The decision in decision block 670 is "YES" when the current deflection ratio is approximately equal to the maximum threshold value. By way of a non-limiting example, the current deflection ratio may be considered approximately equal to the maximum threshold value when the absolute value of the difference between the current deflection ratio and the previous deflection ratio is less than 0.2. When the current deflection ratio is not approximately equal to the maximum threshold value, the decision in decision block 687 is "NO."

When the decision in decision block 687 is "YES," the method 600 ends. When the decision in decision block 670 is "NO," the method 600 advances to decision block 690. Decision block 690 determines whether the CVC 100 was withdrawn too far in block 686. The decision in decision block 690 is "YES" when the current deflection ratio is less than maximum threshold value. When this occurs, continuing to withdraw the CVC 100 will simply reduce the current deflection value. Thus, to make the current deflection ratio approximately equal to the maximum threshold value, the CVC 100 must be advanced.

The decision in decision block 690 is "NO" when the current deflection ratio is greater than the maximum threshold value. Thus, to make the current deflection ratio approximately equal to the maximum threshold value, the CVC 100 must be withdrawn. When the decision in decision block 690 is "NO," the method 600 returns to block 686.

If at anytime during the performance of the method 600, the current deflection ratio is approximately equal to the previously observed maximum deflection ratio, advancement and withdrawal of the CVC 100 may be halted and performance of the method 600 terminated. Similarly, if at anytime during the performance of the method 600, the current deflection ratio is approximately equal to the maximum threshold value, advancement and withdrawal of the CVC 100 is halted and performance of the method 600 terminated.

Method of Using a Single Electrode Pair to
Determine the Location of the TIP of the CVC
within the Right Atrium As discussed above, the P wave voltage is almost entirely negative at the top of the right atrium (see trace 3 of FIG. 2B), biphasic in the mid right atrium (see trace 4 of FIG. 2B), and positive at the bottom of the right atrium (see trace 5 of FIG. 2B). Referring to FIG. 6, a method 190 uses these characteristics of the P wave voltage to determine the location of the tip 112 of the CVC 100 within the atrium. As is apparent to those of ordinary skill in the art, with respect to the method 190, either the unipolar "V" lead trace or the bipolar Lead II trace may be used.

In block 191, any method known in the art or described herein is used to determine the tip 112 is located in the atrium. For example, the tip 112 is in the atrium when the ratio of the deflection value of the currently observed P wave to the reference deflection value is greater than a value that may vary from person to person but is within a range of about 4.0 to about 8.0. Alternatively, the tip 112 may be determined to be in the atrium when the P wave voltage has exceeded a predetermined amount (e.g., about 0.8 mV to about 2.4 mV). Further, the tip 112 may be determined to be in the atrium when the positive/total deflection ratio (i.e., a ratio of the greatest positive deflection value of the initial upwardly deflecting portion of the currently observed P wave, which precedes a downwardly deflecting portion, to the total deflection value) is greater than the predetermined fraction (e.g., one quarter, one eighth, etc.). By way of another example, the tip 112 may be determined to be in the atrium when the voltage (or deflection value) of the currently observed P wave is approximately equivalent to or greater than the voltage (or deflection value) of the QRS complex.

After it is determined the tip 112 is in the right atrium, in block 192, a positive/negative deflection ratio is calculated. The positive/negative deflection ratio is a ratio of the greatest positive deflection value to the smallest negative deflection value. As discussed above, the absolute value of the deflection values may used. Thus, the positive/negative deflection ratio may be calculated as a ratio of the deflection value having the largest absolute value within the portion of the P wave that has a positive polarity to the deflection value having the largest absolute value within the portion of the P wave having a negative polarity. If the P wave is entirely negative, the positive/negative ratio is zero (and the tip 112 is in the upper atrium). On the other hand, if the largest positive deflection value and the smallest negative deflection value are equal, the positive/negative deflection ratio is equal to one. In subsequent blocks 193-197, the positive/negative deflection ratio is used to determine whether the tip 112 is located in the upper, mid, or lower atrium.

In decision block 193, whether the positive/negative deflection ratio is less than a first predetermined threshold value is determined. The first predetermined threshold value may be about 0.80. If decision block 193 determines the ratio is less than the first predetermined threshold value, in block 194, the method 190 determines the tip 112 is in the upper atrium and the method 190 ends.

If decision block 193 determines the ratio is not less than the first predetermined threshold value, the method 190 advances to decision block 195. In decision block 195, whether the positive/negative deflection ratio is greater than a second predetermined threshold value is determined. The second predetermined threshold value may be about 1.20. If decision block 195 determines the ratio is greater than the second predetermined threshold value, in block 196, the method 190 determines the tip 112 is in the lower atrium and the method 190 ends.

If decision block 195 determines the ratio is not greater than the second predetermined threshold value, in block 197, the method 190 determines the tip 112 is in the mid atrium and the method 190 ends. In other words, if the positive/negative deflection ratio is between the first and second predetermined threshold values, the tip 112 is in the mid atrium. Further, if the positive/negative deflection ratio is equal to the first predetermined threshold value or the second predetermined threshold value, the tip 112 is in the mid atrium.

The following table summarizes the relationship between the location of the tip 112 of the CVC 100 and the positive/negative deflection ratio:

TABLE 2

| Location of the tip 112 | Upper Atrium | Mid Atrium | Lower Atrium |
|---|---|---|---|
| Positive/Negative Deflection Ratio: ratio of the greatest positive deflection value to the smallest negative deflection value | <0.80 | 0.80-1.20 | >1.20 |

While Table 2 provides exemplary ranges and/or threshold values for use as a general guideline, those of ordinary skill in the art appreciate that these values may benefit from adjustment as additional anatomic or electrophysiologic data is acquired and such modified values are within the scope of the present invention.

Embodiments Using Two or More Pairs of Electrodes

In the embodiment depicted in FIG. 3B, the CVC 100 includes four longitudinally spaced apart electrodes 150, 152, 154, and 156. Each electrode 150, 152, 154, and 156 is in electrical communication with a wire 160, 162, 164, and 166, respectively. In particular embodiments, the electrodes 150, 152, 154, and 156 are constructed from the distal end of each of the wires 160, 162, 164, and 166. In another embodiment, the electrodes 150, 152, 154, and 156 are attached to the ends of the wires 160, 162, 164, and 166 by any method known in the art for attaching an electrode to a wire, including soldering. The wires 160, 162, 164, and 166 are electrically isolated from one another. The wires 160, 162, 164, and 166 may be insulated from the environment outside the body 130 by the body 130.

The electrodes 150, 152, 154, and 156 and the wires 160, 162, 164, and 166 may be constructed from any suitable materials known in the art such as stainless steel or platinum. Alternatively, a column of conductive material such as an electrolytic material (e.g., saline) may be used to construct one or more of the electrodes 150, 152, 154, and 156 and/or the wires 160, 162, 164, and 166. The electrodes 150, 152, 154, and 156 may be about 6 mm to about 12 mm long, about 6 mm to about 12 mm wide, and about 1 mm to about 4 mm thick. The wires 160, 162, 164, and 166 may be constructed using any electrical lead wire suitable for obtaining an ECG trace.

Optionally, the invention may include two longitudinally spaced apart electrodes 157 and 158. Each of the electrodes 157 and 158 may be electrical communication with a wire 167 and 168, respectively. The electrodes 157 and 158 and wires 167 and 168 may be constructed in a manner substantially similar to that used to construct the electrodes 150, 152, 154, and 156 and the wires 160, 162, 164, and 166, respectively. In particular embodiments, the electrode 157 and 158 are positioned proximal to the electrodes 150, 152, 154, and 156.

Electrodes 150, 152, 154, and 156 may form two anode/cathode pairs. For example, electrodes 150 and 152 may form a first or proximal anode/cathode pair 180 and electrodes 154 and 156 may form a second or distal anode/cathode pair 182. Optional electrodes 157 and 158 may form an optional third or reference anode/cathode pair 184. A pair of electrodes forming an anode/cathode pair may be attached to a pair of insulated wires housed within a single cable. In particular embodiments, a pair of bipolar lead wires are used. In this manner, the four electrodes of the proximal and distal anode/cathode pairs 180 and 182 may be attached to two lead wires. A third bipolar lead wire may be included for use with the reference anode/cathode pair 184. Alternatively, the proximal and distal anode/cathode pairs 180 and 182 may be attached to four insulated wires housed within a single cable such a dual bipolar lead wire.

The wires 160, 162, 164, and 166 and electrodes 150, 152, 154, and 156 may be permanently embedded into the body 130 of the CVC 100 or removably inserted into one or more channels or lumens 132 formed in the CVC 100 for potential future removal and/or replacement. The wires 167 and 168 and electrodes 157 and 158 may be incorporated into the CVC 100 in any manner described with respect to wires 160, 162, 164, and 166 and electrodes 150, 152, 154, and 156, respectively.

The electrodes 150, 152, 154, and 156 are in electrical communication with the environment outside the CVC 100. In particular embodiments, a portion of each of the electrodes 150, 152, 154, and 156 are exposed to the environment outside the CVC 100 by apertures 170, 172, 174, and 176 formed in the body 130 adjacent to the electrodes 150, 152, 154, and 156, respectively. In embodiments including optional electrodes 157 and 158, a portion of each of the electrodes 157 and 158 may be exposed to the environment outside the CVC 100 by apertures 177 and 178 formed in the body 130 adjacent to the electrodes 157 and 158, respectively. The apertures 177 and 178 may be constructed in any manner suitable for constructing apertures 170, 172, 174, and 176. The apertures 170, 172, 174, and 176 may be formed in the body 130 by any method known in the art and the invention is not limited by the method used to construct the apertures 170, 172, 174, and 176. While the electrodes 150, 152, 154, and 156 depicted in the drawings extend outwardly from the body 130 through the apertures 170, 172, 174, and 176, it is understood by those of ordinary skill in the art, that electrodes 150, 152, 154 and 156 may reside at the bottom of the apertures 170, 172, 174, and 176 which may provide a passageway for fluids in the outside environment to the electrodes 150, 152, 154, and 156. Alternatively, the portion of the electrodes 150, 152, 154, and 156 in electrical communication with the environment outside the CVC 100 may be flush with the outside surface of the CVC 100.

The electrode 156 may be located at or spaced from the tip 112. In particular embodiments, the electrode 156 is less than about 5 mm from the tip 112. The spacing between an anode and cathode of the anode/cathode pairs 180 and 182 may be about 1 mm to about 4 mm. In particular embodiments, the spacing between an anode and cathode of the anode/cathode pairs 180 and 182 is about 3 mm.

In particular embodiments, the distance between the electrodes 154 and 152 is less than the height of the right atrium. In an adult, the height of the right atrium may be approximately equal to or greater than about 4 cm. In one exemplary embodiment, the distance between the electrode 154 and 152 may be about 3 cm. In embodiments including optional electrodes 157 and 158, the distance between the electrodes 150 and 158 may be about 10 cm to about 18 cm.

Those of ordinary skill in the art appreciate that the size and spacing of the electrodes provided herein may require modification for use with patients that are larger or smaller than a typical adult and such embodiments are within the scope of the present invention. For example, smaller electrodes with a closer spacing may be required for use with a pediatric patient.

Referring to FIG. 7, the CVC 100 may gain venous access to the SVC by any method known in the art including inserting the CVC 100 in a standard sterile fashion through the subclavian, one of the jugular veins, or a peripheral vein and directing the tip 112 of the CVC 100 through that vein to the SVC.

Each of the anode/cathode pairs 180 and 182 may be used to generate an ECG trace. In this manner, the ECG waveforms detected by the proximal pair 180 may be compared to the ECG waveform detected by the distal pair 182. In particular embodiments, the P wave portion of each trace is compared to determine the position of the tip 112 of the CVC 100 within the SVC, right atrium, and right ventricle.

In embodiments including the reference anode/cathode pair 184, the reference anode/cathode pair 184 may be used to generate an ECG trace. Referring to FIG. 7, because the reference anode/cathode pairs 184 may be located substantially proximally from the proximal and distal anode/cathode pairs 180 and 182, the reference anode/cathode pair 184 may remain in the venous system proximal to or in the proximal SVC after the proximal and distal anode/cathode pairs 180 and 182 have entered the heart. In particular embodiments, the spacing between the anode/cathode pair 184 and the proximal pair 180 is large enough to insure the reference anode/cathode pair 184 remains proximal to or inside the proximal SVC when the distal anode/cathode pair 182 is inside the right ventricle. In this manner, the reference anode/cathode pair 184 may be used to detect the ECG waveform within venous system proximal to or in the proximal SVC while the catheter is being placed.

The ECG waveforms detected by the proximal anode/cathode pair 180 and/or distal anode/cathode pair 182 may be compared to the ECG waveform detected by the reference anode/cathode pair 184. In particular embodiments, the P wave portion of the ECG trace detected by the proximal anode/cathode pair 180 and/or distal anode/cathode pair 182 is compared to P wave portion of the ECG trace detected by the reference anode/cathode pair 184 to determine whether the tip 112 of the CVC 100 is located within the SVC, right atrium, or right ventricle.

Methods of Determining the Location of The TIP of the CVC Using Two or More Electrode Pairs As is apparent to those of ordinary skill in the art, the methods 140, 450, 190, and 600 described above may be performed using the CVC 100 with two or three pairs of electrodes. With respect to each of the methods 140, 450, 190, and 600, the electrode 156 of the distal anode/cathode pair 182 may be substituted for the first electrode 114A (see FIG. 3A) and the electrode 154 of the distal anode/cathode pair 182 may be substituted for the second electrode 114B (see FIG. 3A). By way of another non-limiting example, any one of the electrodes 156, 154, or 152 may be used as the cathode and any one of the electrodes 154, 152, or 150 proximal to the one used as the cathode may be used as the anode. Alternatively, with respect to each of the methods 140, 450, 190, and 600, one or both of the distal anode/cathode pair 182 may be substituted for the first electrode 114A (see FIG. 3A) and one or both of the proximal anode/cathode pair 180 may be substituted for the second electrode 114B (see FIG. 3A). However, as is appreciated by those of ordinary skill in the art, it may be desirable to use the distal most electrode as the cathode.

Referring to FIG. 10, an alternate method 500 of determining the location of the tip 112 of the CVC 100 using two or three pairs of electrodes will now be described. With respect to method 500, unless otherwise indicated, the deflection value is calculated as the sum of the absolute value of the maximum and minimum deflections when the maximum and minimum deflections have opposite polarities. The deflection value is calculated as the larger of the absolute value of the maximum deflection and the absolute value of the minimum deflection when the maximum and minimum deflections have the same polarity.

In first block 510, both the distal anode/cathode pair 182 and the proximal anode/cathode pair 180 are located in the venous system proximal to or in the proximal SVC. A D/P ratio of the deflection value of the distal anode/cathode pair 182 to the deflection value of the proximal anode/cathode pair 180 may be calculated and used to verify the locations of the distal anode/cathode pair 182 and the proximal anode/cathode pair 180 within the venous system proximal to or in the proximal SVC. When both of the anode/cathode pairs 180 and 182 are within the venous system proximal to or in the proximal SVC, the deflection value of the P wave detected by each of them is substantially identical and the D/P ratio of their P wave deflection values equals approximately one. Optionally, the deflection value of one or both of the P waves may be stored or otherwise recorded. For example, the deflection value of the P wave detected by the distal anode/cathode pair 182 or the proximal anode/cathode pair 180 may be stored as a reference deflection value.

In next block 518, the user advances the CVC 100. By way of a non-limiting example, the user may advance the CVC 100 about 0.5 cm to about 1.0 cm. Then, in block 520, the D/P ratio of the deflection value of the distal anode/cathode pair 182 to the deflection value of the proximal anode/cathode pair 180 is calculated. Optionally, the deflection value of one or both of the P waves may be stored or otherwise recorded. Then, the method 500 advances to decision block 524.

The user or operator may wish to continue advancing the CVC 100 until the SA node is detected. When an anode/cathode pair 180 or 182 is approximately 4 cm proximal to the SA node and therefore, by inference, approximately 4 cm proximal to the entrance of the right atrium (or "caval-atrial junction," which is the location of the SA node), the deflection value of the P wave detected by that anode/cathode pair may increase.

When the distal anode/cathode pair 182 enters the right atrium and the proximal anode/cathode pair 180 is still in the venous system proximal to or in the proximal SVC, the deflection value of the P wave detected by the distal anode/cathode pair 182 may be at least four times the deflection value of the P wave detected by the proximal anode/cathode pair 180. Therefore, when the D/P ratio of the P wave deflection values of the distal anode/cathode pair 182 to the proximal anode/cathode pair 180 is greater than or equal to about 4.0 to about 8.0, the user or operator should withdraw the CVC 100. By way of a non-limiting example, the user may withdraw the CVC 100 about 0.5 cm to about 1.0 cm.

In decision block 524, a predetermined maximum threshold value "TR1" may be used to determine whether the user or operator should withdraw the CVC 100. If the D/P ratio exceeds the maximum threshold value "TR1," the decision in decision block 524 is "YES," and in block 528, the CVC 100 is withdrawn. In particular embodiments, the maximum threshold value "TR1" may range from approximately 4.0 to approximately 8.0. By way of a non-limiting example, the maximum threshold value "TR1" may be about 8.0. If the D/P ratio does not exceed the maximum threshold value "TR1," the decision in decision block 524 is "NO," and the method 500 advances to decision block 532.

When the distal anode/cathode pair 182 enters the right ventricle, the proximal anode/cathode pair 180 may be in the right atrium. Because the deflection value of the P wave experienced in the right ventricle is approximately equal to the deflection value of the P wave experienced in the proximal SVC, the D/P ratio of the P wave deflection values of the distal anode/cathode pair 182 to the proximal anode/cathode pair 180 (which is now in the upper atrium) is less than or equal to about one half. Therefore, when the D/P ratio is less than about one half, the user or operator should withdraw the CVC 100.

In decision block 532, a predetermined minimum threshold value "TMIN" may be used to determine whether the user or operator should withdraw the CVC 100. If the D/P ratio is less than the predetermined minimum threshold value "TMIN," the decision in decision block 532 is "YES," and in block 528, the CVC 100 is withdrawn. In particular embodiments, the predetermined minimum threshold value "TMIN" may be approximately one half.

If the D/P ratio is not less than the minimum threshold value "TMIN," the decision in decision block 532 is "NO," and the distal anode/cathode pair 182 and the proximal anode/cathode pair 180 may both be in the right atrium at the same time. When this occurs, the deflection value of the P waves detected by each would be very similar if not identical making their D/P ratio approximately equal to one. Therefore, in block 536, a P/R ratio or D/R ratio (described below) may be calculated to determine the location of the tip 112 of the CVC 100.

The P/R ratio may include the ratio of the deflection value of the P wave detected by the proximal anode/cathode pair 180 to the stored reference deflection value of the P wave detected in the proximal SVC. In particular embodiments, the P/R ratio may include the ratio of the deflection value of the P wave detected by the proximal anode/cathode pair 180 to a reference deflection value of the P wave detected by the reference anode/cathode pair 184. In embodiments that include a reference anode/cathode pair 184, the reference anode/cathode pair 184 may be used to detect the P wave in the proximal SVC. Because the proximal anode/cathode pair 180 is inside the right atrium, the deflection value of its P wave is greater than or equal to about four times to about eight times the deflection value of the P wave observed in the proximal SVC. When the P/R ratio is equal to or greater than a threshold value "TR2" within a range of about 4.0 to about 8.0, the user or operator should withdraw the CVC 100. By way of a non-limiting example, the threshold value "TR2" may be about 4.0. By way of a non-limiting example, the threshold value "TR2" may be equal to the predetermined maximum threshold value "TR1." Alternatively, the threshold value "TR2" could be set equal the largest D/R ratio observed thus far.

After the P/R ratio is calculated, in decision block 540, the threshold value "TR2" may be used to determine whether the user or operator should withdraw the CVC 100. If the P/R ratio exceeds the threshold value "TR2," the decision in decision block 540 is "YES," and in block 528, the CVC 100 is withdrawn. Otherwise, if the P/R ratio does not exceed the threshold value "TR2," the user does not need to withdraw the CVC 100, and the decision in decision block 540 is "NO." Then, the method 500 ends.

Alternatively, in block 536, a D/R ratio may be calculated to determine the location of the tip 112 of the CVC 100. The D/R ratio may include the ratio of the deflection value of the P wave detected by the distal anode/cathode pair 182 to the stored reference deflection value of the P wave detected in the proximal SVC. In particular embodiments, the D/R ratio may include the ratio of the deflection value of the P wave detected by the distal anode/cathode pair 182 to the reference deflection value of the P wave detected by the reference anode/cathode pair 184. In embodiments that include a reference pair 184, the reference pair 184 may be used to detect the P wave in the proximal SVC. Because the distal anode/cathode pair 182 is inside the right atrium, the deflection value of its P wave is greater than or equal to about four times to about eight times the deflection value of the P wave observed in the proximal SVC.

When D/R ratio is equal to or greater than a threshold value "TR3" within a range of about 4.0 to about 8.0, the user or operator should withdraw the CVC 100. By way of a non-limiting example, the threshold value "TR3" may be about 4.0. By way of a non-limiting example, the threshold value "TR3" may be equal to the predetermined maximum threshold value "TR1." Alternatively, the threshold value "TR3" could be set equal the largest D/R ratio observed thus far. Under these circumstances, in decision block 540, the threshold value "TR3" may be used to determine whether the user or operator should withdraw the CVC 100, i.e., if the D/R ratio exceeds the threshold value "TR3," the decision in decision block 540 is "YES," and the CVC 100 is withdrawn in block 528. Otherwise, if the D/R ratio does not exceed the threshold value "TR3," the user does not need to withdraw the CVC 100, and the decision in decision block 540 is "NO." Then, the method 500 ends.

After the CVC 100 is withdrawn in block 528, the method 500 may return to block 520 to recalculate the D/P ratio.

In method 500, determining when to withdraw the CVC 100 is unaffected by wide anatomic variability between individual people because instead of using predetermined threshold deflection values, the D/P ratio, P/R ratio, and/or D/R ratio of deflection values obtained from each individual is used.

The following table summarizes the relationship between the location of the tip 112 of the CVC 100 and the deflection values of the P waves detected by the proximal and distal anode/cathode pairs 180 and 182:

TABLE 3

| | | | | |
|---|---|---|---|---|
| Location of the distal anode/cathode pair 182 | Proximal SVC | Right Atrium | Right Atrium | Right Ventricle |
| Location of the proximal anode/cathode pair 180 | Proximal SVC | Proximal SVC | Right Atrium | Right Atrium |
| D/P ratio: Ratio of the deflection value of the distal anode/cathode pair 182 to the deflection value of the proximal anode/cathode pair 180 | ≈1 | ≥TR1 | ≈1 | ≤TMIN |

TABLE 3-continued

| | | | | |
|---|---|---|---|---|
| P/R ratio: Ratio of the deflection value of the P wave detected by the proximal anode/cathode pair 180 and the deflection value of the P wave detected in the proximal SVC | ≈1 | ≈1 | ≥TR2 | ≥TR2 |
| D/R ratio: Ratio of the deflection value of the P wave detected by the distal anode/cathode pair 182 and the deflection value of the P wave detected in the proximal SVC | ≈1 | ≥TR3 | ≥TR3 | ≈1 |

As mentioned above, each of the threshold values "TR1," "TR2," and "TR3" in Table 3 may be within a range of about 4.0 to about 8.0 and the minimum threshold value "TMIN" may be about 0.5. Alternatively, the threshold values "TR1," "TR2," and "TR3" in Table 3 may be set equal the largest D/R ratio observed during the performance of the method 500. By way of another example, the threshold values "TR1," "TR2," and "TR3" in Table 3 may be set equal the largest D/R ratio observed for the patient during the performance of any of the methods described herein and recorded for use with the method 500. While exemplary threshold values "TR1," "TR2," "TR3," and "TMIN" have been provided for use as a general guideline, those of ordinary skill in the art appreciate that these values may benefit from adjustment as additional anatomic or electrophysiologic data is acquired and such modified values are within the scope of the present invention.

As is apparent from Table 3, either of the P/R ratio and the D/R ratio may be calculated first and used instead of the D/P ratio. For example, if the P/R ratio is calculated first, it may be compared to the threshold value "TR2." If the P/R ratio is greater than or equal to the threshold value "TR2," the tip 112 is in the right atrium or right ventricle and should be withdrawn. If the P/R ratio is less than the threshold value "TR2," the tip 112 is in the right atrium or proximal SVC. When this occurs, either the D/P ratio or the D/R ratio may be calculated. If the D/P ratio is calculated, it may be compared to the predetermined maximum threshold value "TR1." If the D/P ratio is greater than or equal to the predetermined maximum threshold value "TR1," the tip 112 should be withdrawn. If the D/R ratio is calculated, it may be compared to the threshold value "TR3." If the D/R ratio is greater than or equal to the threshold value "TR3," the tip 112 should be withdrawn.

Alternatively, if the D/R ratio is calculated first, it may be compared to the threshold value "TR3." If the D/R ratio is greater than or equal to the threshold value "TR3," the tip 112 is in the right atrium and should be withdrawn. If the D/R ratio is less than the threshold value "TR3," the tip 112 is in the right ventricle or proximal SVC. When this occurs, either the D/P ratio or the P/R ratio may be calculated. If the D/P ratio is calculated, it may be compared to the predetermined minimum threshold value "TMIN." If the D/P ratio is less than or equal to the predetermined minimum threshold value "TMIN," the tip 112 should be withdrawn. If the P/R ratio is calculated, it may be compared to the threshold value "TR2." If the P/R ratio is greater than or equal to the threshold value "TR2," the tip 112 should be withdrawn.

In addition to using the method 500 to determine when to withdraw the CVC 100, the QRS complex portion of the ECG waveforms detected by the distal anode/cathode pair 182 and/or the proximal anode/cathode pair 180 may be used to determine when the tip 112 of the CVC 100 is in the right atrium. Specifically, the tip 112 should be withdrawn because it is in the right atrium when the deflection value of the P wave detected by either the distal anode/cathode pair 182 or the proximal anode/cathode pair 180 is approximately equivalent to or greater than the voltage (or deflection value) of the QRS complex detected simultaneously by the same anode/cathode pair. The P wave and QRS complex typically look similar and deflect in the same direction. The CVC 100 may be advanced until the deflection value of the P wave is slightly less than or approximately equal to the deflection value of the QRS complex.

Further, a positive/total deflection ratio of the largest positive deflection value (of an initial positive or upwardly deflecting portion preceding a downwardly deflecting portion of a P wave detected by the distal anode/cathode pair 182 and/or the proximal anode/cathode pair 180) to the total deflection value (of the P wave detected by the distal anode/cathode pair 182 and/or the proximal anode/cathode pair 180) may be used to determine when the tip 112 of the CVC 100 is in the right atrium. As discussed above, the P wave voltage is almost entirely negative at the top of the right atrium (see trace 3 of FIG. 2B), biphasic in the mid right atrium (see trace 4 of FIG. 2B), and positive at the bottom of the right atrium (see trace 5 of FIG. 2B). Thus, advancement of the tip 112 may be halted when the positive/total deflection ratio is greater than a predetermined fraction (e.g., one quarter, one eighth, etc.). As mentioned above, with respect to the single electrode pair embodiments, when the positive/total deflection ratio exceeds the predetermined fraction, the tip 112 is in the right atrium.

As is apparent to those of ordinary skill, the proximal and distal anode/cathode pairs 180 and 182 may be used to detect the instantaneous location of the tip 112. Therefore, if the tip 112 migrates into the atrium or ventricle, this movement may be detected immediately. Following such an occurrence, a medical professional may be alerted via a signal, such as an alarm, and the like, to reposition the tip 112.

If the tip 112 is determined to be in the atrium, the method 190 described above may be used to determine the position of the tip 112 inside the atrium. Specifically, the electrode 114B (see FIG. 3A) may be attached to the skin of the patient. Then, the method 190 may be used to determine a positive/negative deflection ratio for the P wave detected by the electrode 114B and one of the electrodes 154 and 156 of the distal anode/cathode pair 182. The positive/negative deflection ratio may be compared to the first and second threshold values (see Table 2) and the location of the tip 112 within the atrium determined. Alternatively, instead of attaching the electrode 114B to the skin of the patient, one of the electrodes 157 and 158 of the reference anode/cathode pair 184 may be used. In such embodiments, the positive/negative deflection ratio is determined for the P wave detected by one of the electrodes 157 and 158 of the reference anode/cathode pair 184 and one of the electrodes 154 and 156 of the distal anode/cathode pair 182. As mentioned above, it may be desirable to use the most distal electrode 156 of the distal anode/cathode pair 182. The positive/negative deflection ratio may be compared to the first and second threshold values (see Table 2) and the location of the tip 112 within the atrium determined.

Because the voltage across each of the anode/cathode pairs 180 and 182 may vary depending over time, the voltage across wires 164 and 166 and wires 160 and 162 may each constitute a time-varying signal that can be analyzed using standard signal processing methods well known in the art. In a typical patient, the maximum of voltage across the anode/cathode pairs 180 and 182 may range from about 0.2 mV to about 3 mV. The signal from each anode/cathode pairs 180 and 182 may be amplified and/or filtered to improve the signal quality. A distal signal may be detected by the distal anode/cathode pair 182 and a proximal signal may be detected by the proximal anode/cathode pair 180. Similarly, an optional reference signal may be detected by the reference anode/cathode pair 184.

A separate ECG trace may be constructed for distal and proximal signals. In some embodiments, an ECG trace may also be constructed for the reference signal. The P wave portion of one or more of these ECG traces may be identified and analyzed. For example, the ECG trace of the distal signal may be visualized by connecting wires 164 and 166 of the distal anode/cathode pair 182 to a device such as a PACERVIEW® signal conditioner designed specifically to construct and display an ECG trace from a time varying low voltage signal. Similarly, the ECG trace of the proximal signal may be viewed by connecting the wires 160 and 162 of the proximal anode/cathode pair 180 to a PACERVIEW® signal conditioner. The ECG trace of the reference signal may be viewed by connecting the wires 167 and 168 of the proximal anode/cathode pair 184 to a PACERVIEW® signal conditioner.

In particular embodiments, each of the four wires 160, 162, 164, and 166 may be coupled to a signal analysis system for analysis of the voltage information detected by the electrodes 150, 152, 154, and 156, respectively. In embodiments including electrodes 157 and 158, the wires 167 and 168 may be coupled to the signal analysis system for analysis of the voltage information detected by the electrodes 157 and 158, respectively. An exemplary signal analysis system 200 for analyzing the signals carried by wires 160, 162, 164, and 166 and alerting the user or operator when to withdraw the tip 112 of the CVC 100 may be viewed in FIG. 7. In an alternate embodiment, the system 200 may also analyze the signals carried by wires 167 and 168.

System 200

FIG. 8 is a block diagram of the components of the exemplary system 200. The system 200 may include a programmable central processing unit (CPU) 210 which may be implemented by any known technology, such as a microprocessor, microcontroller, application-specific integrated circuit (ASIC), digital signal processor (DSP), or the like. The CPU 200 may be integrated into an electrical circuit, such as a conventional circuit board, that supplies power to the CPU 210. The CPU 210 may include internal memory or memory 220 may be coupled thereto. The memory 220 may be coupled to the CPU 210 by an internal bus 264.

The memory 220 may comprise random access memory (RAM) and read-only memory (ROM). The memory 220 contains instructions and data that control the operation of the CPU 210. The memory 220 may also include a basic input/output system (BIOS), which contains the basic routines that help transfer information between elements within the system 200. The present invention is not limited by the specific hardware component(s) used to implement the CPU 210 or memory 220 components of the system 200.

All or a portion of the deflection values and/or deflection ratios calculated by the methods 140, 190, 450, 500, and 600, including the reference deflection value, may be stored in the memory 220 for use by the methods.

Optionally, the memory 220 may include external or removable memory devices such as floppy disk drives and optical storage devices (e.g., CD-ROM, R/W CD-ROM, DVD, and the like). The system 200 may also include one or more I/O interfaces (not shown) such as a serial interface (e.g., RS-232, RS-432, and the like), an IEEE-488 interface, a universal serial bus (USB) interface, a parallel interface, and the like, for the communication with removable memory devices such as flash memory drives, external floppy disk drives, and the like.

The system 200 may also include a user interface 240 such as a standard computer monitor, LCD, colored lights 242 (see FIG. 7), PACERVIEW® signal conditioner, ECG trace display device 244 (see FIG. 7), or other visual display including a bedside display. In particular embodiments, a monitor or handheld LCD display may provide an image of a heart and a visual representation of the estimated location of the tip 112 of the CVC 100. The user interface 240 may also include an audio system capable of playing an audible signal. In particular embodiments, the user interface 240 includes a red light indicating the CVC 100 should be withdrawn and a green light indicating the CVC 100 may be advanced. In another embodiment, the user interface 240 includes an ECG trace display device 244 capable of displaying the ECG trace of the distal and proximal signals. In the embodiment depicted in FIG. 7, the user interface 240 includes a pair of lights 242, one red and the other green, connected in series with a ECG trace display device 244. In some embodiments, a display driver may provide an interface between the CPU 210 and the user interface 240. Because an ultrasound machine is typically used when placing peripherally inserted central catheters ("PICC" lines), the system 200 may be incorporated into an ultrasound unit (not shown).

The user interface 240 may permit the user to enter control commands into the system 200. For example, the user may command the system 200 to store information such as the deflection value of the P wave inside the SVC. The user may also use the user interface 240 to identify which portion of the ECG trace corresponds to the P wave. The user interface 240 may also allow the user or operator to enter patient information and/or annotate the data displayed by user interface 240 and/or stored in memory 220 by the CPU 210. The user interface 240 may include a standard keyboard, mouse, track ball, buttons, touch sensitive screen, wireless user input device and the like. The user interface 240 may be coupled to the CPU 210 by an internal bus 268.

Optionally, the system 200 may also include an antenna or other signal receiving device (not shown) such as an optical sensor for receiving a command signal such as a radio frequency (RF) or optical signal from a wireless user interface device such as a remote control. The system 200 may also include software components for interpreting the command signal and executing control commands included in the command signal. These software components may be stored in memory 220.

The system 200 includes an input signal interface 250 for receiving the distal and proximal signals. The input signal interface 250 may also be configured to receive the reference signal. The input signal interface 250 may include any standard electrical interface known in the art for connecting a double dipole lead wire to a conventional circuit board as well as any components capable of communicating a low voltage time varying signal from a pair of wires through an internal bus 262 to the CPU 210. The input signal interface 250 may include hardware components such as memory as well as standard signal processing components such as an analog to digital converter, amplifiers, filters, and the like.

The various components of the system 200 may be coupled together by the internal buses 262, 264, and 268. Each of the internal buses 262, 264, and 268 may be constructed using a data bus, control bus, power bus, I/O bus, and the like.

The system 200 may include instructions 300 executable by the CPU 210 for processing and/or analyzing the distal and/or proximal signals. These instructions may include computer readable software components or modules stored in the memory 220. In particular embodiments, the instructions 300 include instructions for performing the method 500 (see FIG. 10).

The instructions 300 may include an ECG Trace Generator Module 310 that generates a traditional ECG trace from the distal and/or proximal signals. In some embodiments, the ECG Trace Generator Module 310 may generate a traditional ECG trace from the reference signal. As is appreciated by those of ordinary skill in the art, generating an ECG trace from an analog signal, such as the distal and proximal signals, may require digital or analog hardware components, such as an analog to digital converter, amplifiers, filters, and the like and such embodiments are within the scope of the present invention. In particular embodiments, some or all of these components may be included in the input signal interface 250. In an alternate embodiment, some or all of these components may be implemented by software instructions included in the ECG Trace Generator Module 310. The ECG Trace Generator 310 may include any method known in the art for generating an ECG trace from a time varying voltage signal.

The ECG Trace Generator 310 may record one or more of the ECG traces generated. Presently, a chest x-ray is used to document the location of the tip 112. This documentation may be used to prove the tip 112 of the CVC was placed correctly. Using the present techniques, the recorded ECG trace(s) may be used in addition to or instead of the chest x-ray to document tip 112 location. For example, the recorded ECG trace(s) may demonstrate that the tip 112 has migrated from the proximal SVC into the right atrium. Further, the recorded ECG trace(s) could document the repositioning of the tip 112 back into proximal SVC. Additionally, the recorded ECG trace(s) could document that the tip 112 was initially placed correctly and did not migrate from its initial position. In this manner, the ECG trace(s) could be used to document the correct or incorrect placement of the tip 112 and could be included in the patient's medical record, replacing or supplementing the prior art chest x-ray. Further, if the tip 112 does migrate, the recorded ECG trace(s) could be used to determine whether the tip entered the atrium, how far into the atrium the tip migrated, and/or whether the tip entered the ventricle.

The instructions 300 may include a P Wave Detection Module 320 for detecting or identifying the P wave portion of the ECG trace. The P wave portion of the ECG trace may be detected using any method known in the art. In particular embodiments, the P Wave Detection Module 320 receives input from the user or operator via the user interface 240. The input received may identify the P wave portion of the ECG trace. Optionally, the P Wave Detection Module 320 may include instructions for identifying the QRS complex as well as the P wave portion of the ECG trace. Further, the P Wave Detection Module 320 may include instructions for determining a deflection value for an initial upwardly deflecting portion of a single P wave preceding a downwardly deflecting portion. The P Wave Detection Module 320 may also include instructions for determining a positive/total deflection ratio of the largest positive deflection value for the initial upwardly deflecting portion of the P wave to the deflection value for the entire P wave.

The instructions 300 may include an Interpretive Module 330 for comparing the P wave generated for the distal, proximal, and/or reference signals. In particular embodiments, the Interpretive Module 330 determines the deflection value of the P wave generated for the distal and/or proximal signals. In some embodiments, the Interpretive Module 330 determines the deflection value of the P wave generated for the reference signal. The Interpretive Module 330 may direct the CPU 210 to store the deflection value of the distal, proximal, and/or reference signals in memory 220. In particular, it may be desirable to store the deflection value of the P wave encountered in the proximal SVC. The Interpretive Module 330 may receive input from the user or operator via the user interface 240 instructing the Interpretive Module 330 to store the deflection value. This information could be stored under a unique patient identifier such as a medical record number so that tip location information could be accessed anytime during the life of the CVC 100, potentially avoiding the need for a chest x-ray to document current location.

With respect to performing the method 500 illustrated in FIG. 10, the Interpretive Module 330 may also determine the D/P ratio by calculating the ratio of the deflection value of the distal signal to the deflection value of the proximal signal. If the D/P ratio is approximately equal to or greater than the maximum threshold value "TR1," the tip 112 of the CVC 100 may be in the right atrium. The Interpretive Module 330 may alert the user or operator that the tip 112 is in the right atrium and the CVC 100 should be withdrawn from the right atrium. On the other hand, if the D/P ratio is approximately equal to or less than the minimum threshold value "TMIN," the tip 112 of the CVC 100 may be in the right ventricle. The Interpretive Module 330 may alert the user or operator that the tip 112 is in the right ventricle and the CVC 100 should be withdrawn therefrom.

If the D/P ratio is less than the maximum threshold value "TR1" and greater than the minimum threshold value "TMIN," the tip 112 may be in either the right atrium or the proximal SVC. When this happens, the Interpretive Module 330 may calculate the P/R ratio and/or the D/R ratio. For example, if the D/R ratio is approximately equal to or greater than the threshold value "TR3," the tip may be in the right atrium and should be withdrawn therefrom. When this occurs, the Interpretive Module 330 may alert the user or operator that the tip 112 is in the right atrium. If the D/R ratio is approximately less than the threshold value "TR3," the tip 112 is in the SVC and may be advanced if the operator so chooses. The Interpretive Module 330 may communicate to the user or operator that the tip 112 may be advanced.

On the other hand, if the P/R ratio is approximately equal to or greater than the threshold value "TR2," the tip may be in the right atrium or right ventricle and should be withdrawn therefrom. When this occurs, the Interpretive Module 330 may alert the user or operator to withdraw the tip 112. If the P/R ratio is approximately less than the threshold value "TR2," the tip 112 is in the SVC (because the D/P ratio is less than the maximum threshold value "TR1") and may be advanced if the operator so chooses. The Interpretive Module 330 may communicate to the user or operator that the tip 112 may be advanced.

In an alternate embodiment, the P/R ratio is used instead of the D/P ratio. Whenever the P/R ratio is approximately equal to or greater than the threshold value "TR2," the user or operator may be alerted to withdraw the CVC 100. If the P/R ratio is approximately less than the threshold value "TR2," the D/P ratio or D/R ratio may be calculated and used to determine the position of the tip 112 of the CVC 100.

In another alternate embodiment, the D/R ratio is used instead of the D/P ratio. Whenever the D/R ratio is approximately equal to or greater than the threshold value "TR3," the user or operator may be alerted to withdraw the CVC 100. If the D/R ratio is approximately less than the threshold value "TR3," the D/R ratio or P/R ratio may be calculated and used to determine the position of the tip 112 of the CVC 100.

In particular embodiments, the instructions in the Interpretive Module 330 direct the CPU 210 to use the user interface 240 to communicate whether the tip 112 should be withdrawn to the user. The CPU 210 may use the user interface 240 to communicate the tip 112 may be advanced. Because the Interpretive Module 330 may interpret the P wave to obtain the deflection values of the distal and proximal signals, compare the deflection values, and provide the operator with immediate real-time feedback, the operator need not interpret the actual ECG waveforms.

Monitor 127

The monitor 127 of the system 121 for use with single pair of electrode embodiments will now be described. Returning to FIG. 3A, for illustrative purposes, the monitor 127 is described as coupled to each of the electrodes 114A and 114B by wires 123 and 129, respectively. However, in alternate embodiments, the monitor 127 is coupled to the electrodes 176 and 174 of the distal anode/cathode pair 182 (see FIG. 3B) by wires 123 and 129, respectively. By way of another alternate embodiment, one or both of the distal anode/cathode pair 182 may be coupled to the monitor 127 by wire 123 and one or both of the proximal anode/cathode pair 180 may be coupled to the monitor 127 by wire 129.

Referring to FIG. 9, the monitor 127 includes a signal analysis system 400 that may be substantially similar to the signal analysis system 200 described above. Specifically, the system 400 may construct an ECG trace for the electrical signals detected by the pair of electrodes 114, and identify and analyze the P wave portion of the ECG trace using any method discussed above with respect to the system 200. Further, the system 400 is configured to display information to the user or operator communicating the current position of the tip 112 of the CVC 100.

Like reference numerals are used to identify substantially identical components in FIGS. 8 and 9. The system 400 includes the CPU 210, the memory 220, the input signal interface 250 for receiving the signals detected by the pair of electrodes 114, and a user interface 410. Like system 200, the various components of the system 400 may be coupled together by the internal buses 262, 264, and 268.

All or a portion of the deflection values and/or deflection ratios calculated by the methods 140, 190, 450, and 600, including the reference deflection value, may be stored in the memory 220 for use by the methods.

The system 400 differs from the system 200 with respect to the user interface 410 and at least a portion of the computer-executable instructions stored in memory 220. Returning to FIG. 3A, in some embodiments, the user interface 410 includes an array of lights 412, a first portion 412A of which corresponds to ratio values below or equal to the first predefined threshold value of the method 140 (see FIG. 4), a second portion 412B of which corresponds to the range of ratio values greater than the first predefined threshold value and less than or equal to the second threshold value of the method 140, and a third portion 412C of which indicates the second predefined threshold value has been exceeded.

By way of a non-limiting example, the first portion 412A may include an array of green lights. The number of green lights lit may indicate the magnitude of the ratio of the deflection value of the currently observed P wave to the reference deflection value. For example, the first portion may include eight lights. The first light may indicate the ratio is less than or equal to 0.8. For each 0.2 increase in the ratio, another green light may be lit until all eight green lights are lit and the ratio is approximately equal to 4.0. If the ratio decreases to less than 4.0, for each 0.2 decrease in the ratio, a green light may be turned off until only a single green light is lit.

By way of a non-limiting example, the second portion of lights may include an array of yellow lights. The number of yellow lights lit may indicate the magnitude of the ratio of the deflection value of the currently observed P wave to the reference deflection value. For example, the second portion may include eight yellow lights. The first yellow light may indicate the ratio is approximately equal to about 4.4 to about 4.5. For each 0.2 increase in the ratio above 4.4, another yellow light may be lit until all eight yellow lights are lit and the ratio is approximately equal to 6.0. If the ratio decreases to less than 6.0, for each 0.2 decrease in the ratio, a yellow light may be turned off until the ratio is less than 4.4 and none of the yellow lights are lit.

By way of a non-limiting example, the third portion may include a single red light indicating the magnitude of the ratio of the deflection value of the currently observed P wave to the reference deflection value has exceeded 6.0. If the ratio decreases to less than 6.0, the red light may be turned off. In this manner, the user interface 410 provides greater resolution for ratio values less than or equal to the first predefined threshold value than for ratio values between the first and second predefined threshold values.

While the above example has been described as including lights (such as LEDs, conventional light bulbs, and the like), those of ordinary skill in the art appreciate that any indicator may used and such embodiments are within the scope of the present teachings. For example, a monitor displaying a graphical representation of lights, a figure, such as a bar, that increases or decreases in size to reflect an increase or decrease in the ratio, and the like may be used in place of the array of lights. Optionally, the user interface 410 may include a screen 420 (see FIG. 3A) configured to display information to the user or operator. For example, the screen 420 may display an image of a heart and a visual representation of the estimated location of the tip 112 of the CVC 100. Alternatively, the screen 420 may display the words "ADVANCE," "HOLD," or "WITHDRAW" as appropriate.

The user interface 410 may also indicate when the tip 112 is located in the ventricle. By way of a non-limiting example, the user interface 410 may include a light, audio signal, or other indicator configured to indicate the tip 112 has entered the ventricle.

In some embodiments, a display driver may provide an interface between the CPU 210 and the user interface 410. Optionally, the user interface 410 includes an audio system capable of playing an audible signal. For example, the audio system may produce a tone that increases in pitch as the ratio increases and decreases in pitch as the ratio decreases may be used. Alternatively, the audio system may produce one tone when the ratio is greater than the first predefined threshold value, indicating the tip 112 should be withdrawn. In such embodiments, the audio system may produce another more urgent or annoying tone when the ratio is above the second predefined threshold value. Further, the audio system may be silent when the ratio is below the first predefined threshold value.

The user interface 410 may permit the user to enter control commands into the system 200. For example, the user may command the system 200 to store information such as the deflection value of the P wave inside the proximal SVC (e.g., the reference deflection value), atrium (e.g., the reference atrium deflection value), and the like. The user may also use the user interface 410 to identify manually which portion of the ECG trace corresponds to the P wave. The user interface 410 may also allow the user or operator to enter patient information (such as a patient identifier number) and/or annotate the data displayed by user interface 410 and/or stored in memory 220 by the CPU 210. The user interface 410 may include a standard keyboard, mouse, track ball, buttons 416, touch sensitive screen, wireless user input device and the like. The user interface 410 may be coupled to the CPU 210 by an internal bus 268.

By way of a non-limiting example, a patient's reference deflection value (detected when the tip 112 was located in the proximal SVC) and/or reference atrium deflection value (detected when the tip 112 was located in the atrium) could be stored in the memory 220 and associated with the patient's patient identifier number or some other identification number. In this manner, the patient's recorded reference deflection value could be used anytime during the life of the CVC 100 by recalling the reference deflection value from memory 220 using the patient's patient identifier number, which could be entered manually using the user interface 410.

Optionally, the system 400 may also include an antenna or other signal receiving device (not shown) such as an optical sensor for receiving a command signal such as a radio frequency (RF) or optical signal from a wireless user interface device such as a remote control. The system 400 may also include software components for interpreting the command signal and executing control commands included in the command signal. These software components may be stored in memory 220.

The system 400 includes instructions 300 executable by the CPU 210 for processing and/or analyzing the electrical signals detected by the pair of electrodes 114. The instructions 300 may include the ECG Trace Generator Module 310 that generates a traditional ECG trace from the signals detected by the pair of electrodes 114, the P Wave Detection Module 320 for detecting or identifying the P wave portion of the ECG trace, and the Interpretive Module 330. As discussed above with respect to the system 200, the ECG Trace Generator Module 310 may record the ECG trace generated thereby.

Optionally, the P Wave Detection Module 320 may include instructions for identifying the QRS complex as well as the P wave portion of the ECG trace. Further, the P Wave Detection Module 320 may include instructions for determining a deflection value for an initial upwardly deflecting portion of a single P wave preceding a downwardly deflecting portion. The P Wave Detection Module 320 may also include instructions for determining a positive/total deflection ratio of the largest positive deflection value for the initial upwardly deflecting portion of the P wave to the deflection value for the entire P wave.

Like the Interpretive Module 330 of the system 200, the Interpretive Module 330 of the system 400 determines the deflection value of the P wave detected by a pair of electrodes (i.e., the pair of electrodes 114). However, other functions performed by the Interpretive Module 330 may differ in system 400 from those performed by the Interpretive Module 330 in system 200. The Interpretive Module 330 directs the CPU 210 to store the deflection value of the P wave detected by the pair of electrodes 114 in the proximal SVC in memory 220. The Interpretive Module 330 may receive input from the user or operator via the user interface 410 instructing the Interpretive Module 330 to store the deflection value.

The Interpretive Module 330 also includes instructions for performing the method 140, 190, and/or the method 600. With respect to the method 140 (see FIG. 4), the Interpretive Module 330 may determine the ratio of the deflection value of the currently observed P wave to the reference deflection value. The Interpretive Module 330 may compare this ratio to the first predefined threshold (e.g., about 1.5). If the ratio is less than or equal to the first predefined threshold, the Interpretive Module 330 determines the tip 112 is in the SVC. Further, if the determination is made in block 143, the Interpretive Module 330 may signal the user or operator to advance the tip 112. If the determination is made in block 145, the Interpretive Module 330 may signal the user or operator to stop withdrawing the tip 112.

If the ratio is greater than the first predefined threshold, the Interpretive Module 330 determines the tip 112 is not in a desired location and instructs the user interface 410 to signal the user or operator to withdraw the tip.

The Interpretive Module 330 may compare the ratio to the second predefined threshold value (e.g., about 2.0). If the ratio is less than or equal to the second predefined threshold value, the Interpretive Module 330 determines the tip 112 is in the distal SVC near the SA node or in the atrium near the SA node. If the ratio is greater than the second predefined threshold value, the Interpretive Module 330 determines the tip 112 is in the atrium.

Optionally, the Interpretive Module 330 may determine the ratio of the deflection value of the current P wave detected by the pair of electrodes 114 to the reference atrium deflection value. The Interpretive Module 330 may compare this ratio to the third predefined threshold value (e.g., about 0.5) to determine whether the tip 112 is in the atrium or the ventricle.

With respect to the method 190 (see FIG. 6), the Interpretive Module 330 may determine the tip 112 is located within the right atrium using any method known in the art or disclosed herein. The Interpretive Module 330 then calculates the positive/negative deflection ratio and compares this ratio to the first predetermined threshold value (e.g., about 0.30). If the positive/negative deflection ratio is less than the first predetermined threshold value, the Interpretive Module 330 determines the tip 112 is in the upper right atrium. On the other hand, if the positive/negative deflection ratio is greater than or equal to the first predetermined threshold value, the Interpretive Module 330 compares positive/negative deflection ratio to the second predetermined threshold value (e.g., about 1.30). If the positive/negative deflection ratio is greater than the second predetermined threshold value, the Interpretive Module 330 determines the tip 112 is in the lower atrium. Otherwise, if the positive/negative deflection ratio is greater than or equal to the first predetermined threshold value and less than or equal to the second predetermined threshold value, the Interpretive Module 330 determines the tip 112 is in the mid atrium.

With respect to the method 600 (see FIGS. 11A and 11B), the Interpretive Module 330 may store a reference deflection value and determine the deflection ratio of the deflection value of the currently observed P wave to the reference deflection value. After the tip 112 is withdrawn or advanced, the Interpretive Module 330 may determine the current deflection ratio of the deflection value of the currently observed P wave to the reference deflection value. The deflection ratio determined before the tip 112 was withdrawn or advanced is stored by the Interpretive Module 330 as a previous deflection ratio.

Each time the tip 112 is moved (e.g., advanced or withdrawn), the Interpretive Module 330 determines whether the current deflection ratio is the largest observed since the CVC 100 was inserted into the venous system, and if the current deflection ratio is the largest deflection ratio observed, stores the current deflection ratio as the maximum deflection ratio.

The Interpretive Module 330 compares the current deflection ratio to the previous deflection ratio. If the current deflection ratio is less than or equal to the previous deflection ratio, the Interpretive Module 330 determines the tip 112 has been advanced too far and may signal the user to withdraw the CVC 100. Then, the Interpretive Module 330 determines whether the tip 112 has been withdrawn far enough. The Interpretive Module 330 may determine the tip 112 has been withdrawn far enough when the positive/total deflection ratio is less than a predetermined fraction (e.g., one quarter, one eighth, etc.). Otherwise, the tip 112 has not been withdrawn far enough. If the tip 112 has not been withdrawn far enough, the Interpretive Module 330 signals the user to withdraw the tip 112.

If the tip 112 has been withdrawn far enough, the Interpretive Module 330 determines whether the current deflection ratio is approximately equal to the maximum deflection ratio. If the current deflection ratio is not approximately equal to the maximum deflection ratio, the Interpretive Module 330 determines the tip 112 has been withdrawn too far and signals the user to advance the CVC 100.

As mentioned above, the Interpretive Module 330 may compare current deflection ratio to the previous deflection ratio. If the current deflection ratio is greater than the previous deflection ratio, the Interpretive Module 330 determines whether the current deflection ratio is less than a maximum threshold value (e.g., 8.0). If the current deflection ratio is less than the maximum threshold value, the Interpretive Module 330 determines the tip 112 has not been advanced far enough and signals the user to advance the CVC 100.

If instead the current deflection ratio is greater than or equal to the maximum threshold value, the Interpretive Module 330 determines whether the current deflection ratio is approximately equal to the maximum threshold value. If the current deflection ratio is not approximately equal to the maximum threshold value, the Interpretive Module 330 determines the tip 112 has been advanced too far and signals the user to withdraw the CVC 100. After the tip 112 is withdrawn, the Interpretive Module 330 determines whether the current deflection ratio is approximately equal to the maximum threshold value.

If the current deflection ratio is not approximately equal to the maximum threshold value, the Interpretive Module 330 determines whether the current deflection ratio is less than the maximum threshold value (indicating the tip 112 has been withdrawn too far). If the current deflection ratio is less than the maximum threshold value, the Interpretive Module 330 determines the tip 112 has been withdrawn too far and signals the user to advance the CVC 100. On the other hand, if the current deflection ratio is still greater than the maximum threshold value, the Interpretive Module 330 determines the tip 112 has not been withdrawn far enough and signals the user to withdraw the CVC 100.

Optionally, whenever the current deflection ratio is approximately equal to the maximum deflection ratio or the maximum threshold value, the Interpretive Module 330 may signal the user to stop moving (e.g., advancing or withdrawing) the CVC 100.

With respect to the methods 140, 190, and 600, the instructions in the Interpretive Module 330 direct the CPU 210 to use the user interface 410 to communicate whether the tip 112 should be withdrawn to the user. Further, the instructions in the Interpretive Module 330 direct the CPU 210 to use the user interface 410 to communicate the tip 112 may be advanced. Because the Interpretive Module 330 may interpret the P wave to obtain the deflection values, compare the deflection values, and provide the operator with immediate real-time feedback, the operator need not interpret the actual ECG waveforms.

Optionally, the system 400 could be coupled to a prior art navigational system, such as a VIASYS MedSystems NAVI-GATOR® BioNavigation® system, manufactured by VIASYS Healthcare Inc. of Conshohocken, Pa., which is principally used to guide peripherally placed lines, such as a peripherally inserted central catheter ("PICC"). Such systems determine the location of a PICC line using magnetic fields that are generated by a detector, and detected by a magnetically activated position sensor located in the tip of a stylet inserted inside the PICC near its tip. By way of a non-limiting example, the detector may include a NAVIGATOR® electronic locating instrument configured to emit low-level, high-frequency magnetic fields. Also by way of a non-limiting example, the stylet may include a MAPCath® Sensor Stylet also manufactured by VIASYS Healthcare Inc.

The sensor in the tip of the stylet is activated by the magnetic field emitted by the detector. The sensor is operable to output its location via a wire coupled to the sensor and extending longitudinally along the PICC to the detector, which is configured to interpret the signal and communicate the location of the tip to the user or operator. As mentioned above, because such navigational systems depend upon a relationship between surface landmarks and anatomic locations, they cannot be used to determine the location of the tip 112 of the CVC 100 with sufficient accuracy. However, the system 400 may be used, in conjunction with a navigational system to improve the accuracy of the navigational system.

By way of non-limiting examples, additional prior art navigational systems include the Sherlock Tip Location System used with the stylet provided in Bard Access Systems PICC kits both of which are manufactured by C. R. Bard, Inc. of Salt Lake City, Utah, the CathRite™ system manufactured by Micronix Pty. Ltd. of Australia, and the like. As is apparent to those of ordinary skill in the art, the present teaching may be combined with one or more of these additional exemplary navigational systems and used to improve the accuracy of those systems.

In further embodiments, the teachings provided herein may be expanded to use electrophysiology procedures for navigating other bodily channels. For example, in the prior art, ECG guidance techniques have been used to place feeding tubes. Because the QRS complex measured in the stomach is upright but in a post pyloric area (first part of the duodenum, beyond the stomach) the QRS complex is down-going, one or more threshold deflection values may be determined and used to determine the placement of the tip of the feeding tube.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method of determining a location of a tip of a central venous catheter having a lumen filled with an electrolytic material, a portion disposed inside the superior vena cava, a second electrode attached to the skin of a subject, and a first electrode in communication with the electrolytic material, the tip having an opening in communication with the lumen that exposes the electrolytic material inside the lumen to the electrical environment outside the tip, the method comprising:

obtaining a reference electrical signal comprising the voltage difference between the first electrode and the second electrode;

generating a reference P wave from the reference electrical signal;

determining a reference deflection value of the reference P wave;

after the tip of the central venous catheter has been moved to a new position, obtaining a new electrical signal comprising the voltage difference between the first electrode and the second electrode;

generating a new P wave from the new electrical signal;

determining a new deflection value of the new P wave;

calculating a ratio of the new deflection value to the reference deflection value;

comparing the ratio to a threshold value; and indicating the tip should be withdrawn based on the comparison of the ratio to the threshold value.

\* \* \* \* \*